United States Patent
McWhirter et al.

(10) Patent No.: US 9,334,334 B2
(45) Date of Patent: May 10, 2016

(54) HISTIDINE ENGINEERED LIGHT CHAIN ANTIBODIES AND GENETICALLY MODIFIED NON-HUMAN ANIMALS FOR GENERATING THE SAME

(71) Applicant: Regeneron Pharmaceuticals, Inc., Tarrytown, NY (US)

(72) Inventors: John McWhirter, Tarrytown, NY (US); Lynn MacDonald, White Plains, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/832,247

(22) Filed: Mar. 15, 2013

(65) Prior Publication Data

US 2013/0247234 A1 Sep. 19, 2013

Related U.S. Application Data

(60) Provisional application No. 61/736,930, filed on Dec. 13, 2012, provisional application No. 61/611,950, filed on Mar. 16, 2012.

(51) Int. Cl.

| | |
|---|---|
| *A01K 67/027* | (2006.01) |
| *C07K 16/00* | (2006.01) |
| *C07K 16/46* | (2006.01) |
| *C12N 15/85* | (2006.01) |

(52) U.S. Cl.
CPC ........... *C07K 16/468* (2013.01); *A01K 67/0275* (2013.01); *A01K 67/0278* (2013.01); *C07K 16/00* (2013.01); *C12N 15/8509* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/515* (2013.01); *C07K 2317/92* (2013.01); *C12N 2800/204* (2013.01)

(58) Field of Classification Search
CPC ........... A01K 67/0278; A01K 67/0275; C07K 16/00; C07K 16/462
See application file for complete search history.

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,603,931 | A | 2/1997 | Raso |
| 5,667,988 | A | 9/1997 | Barbas et al. |
| 5,999,908 | A | 12/1999 | Abelow |
| 6,096,551 | A | 8/2000 | Barbas et al. |
| 6,162,963 | A | 12/2000 | Kucherlapati et al. |
| 6,586,251 | B2 | 7/2003 | Economides et al. |
| 6,596,541 | B2 | 7/2003 | Murphy et al. |
| 6,673,986 | B1 | 1/2004 | Kucherlapati et al. |
| 6,774,279 | B2 | 8/2004 | Dymecki |
| 6,946,548 | B2 | 9/2005 | Sarkar et al. |
| 7,052,873 | B2 | 5/2006 | Tsuchiya |
| 7,067,284 | B1 | 6/2006 | Barbas et al. |
| 7,105,348 | B2 | 9/2006 | Murphy et al. |
| 7,183,076 | B2 | 2/2007 | Arathoon et al. |
| 7,262,028 | B2 | 8/2007 | Van Berkel et al. |
| 7,276,585 | B2 | 10/2007 | Lazar et al. |
| 7,294,754 | B2 | 11/2007 | Poueymirou et al. |
| 7,435,871 | B2 | 10/2008 | Green et al. |
| 7,501,552 | B2 | 3/2009 | Lonberg et al. |
| 7,576,259 | B2 | 8/2009 | Poueymirou et al. |
| 7,659,442 | B2 | 2/2010 | Poueymirou et al. |
| 7,910,798 | B2 | 3/2011 | Tanamachi et al. |
| 8,062,640 | B2 | 11/2011 | Sleeman et al. |
| 8,080,243 | B2 | 12/2011 | Liang et al. |
| 8,158,419 | B2 | 4/2012 | Lonberg et al. |
| 2002/0088016 | A1 | 7/2002 | Bruggemann |
| 2003/0078385 | A1 | 4/2003 | Arathoon et al. |
| 2003/0108925 | A1 | 6/2003 | Dix et al. |
| 2004/0018626 | A1 | 1/2004 | Murphy et al. |
| 2006/0015949 | A1 | 1/2006 | Lonberg et al. |
| 2006/0015957 | A1 | 1/2006 | Lonberg et al. |
| 2006/0099207 | A1 | 5/2006 | Wu et al. |

(Continued)

FOREIGN PATENT DOCUMENTS

| | | |
|---|---|---|
| CN | 1277632 A | 12/2000 |
| CN | 1484707 A | 3/2004 |

(Continued)

OTHER PUBLICATIONS

Paul, WE. Fundamental Immunology, 3$^{rd}$ ed. Raven Press, NY., 1993. Chapter 9. p. 292-295.*
Rudikoff et al., Single amino acid substitution altering antigen-binding specificity. Proc. NatL Acad. Sci. USA vol. 79, pp. 1979-1983, Mar. 1982.*
Panka et al., Variable region framework differences result in decreased or increased affinity of variant anti-digoxin antibodies. Proc. Natl. Acad. Sci. USA, vol. 85, pp. 3080-3084, May 1988.*

(Continued)

*Primary Examiner* — Scott Long
*Assistant Examiner* — Arthur S Leonard
(74) *Attorney, Agent, or Firm* — Brownstein Hyatt Farber Schreck, LLP; Rita S. Wu; Margarita Zippin

(57) ABSTRACT

A genetically modified non-human animal is provided, wherein the non-human animal expresses an antibody repertoire capable of pH dependent binding to antigens upon immunization. A genetically modified non-human animal is provided that expresses a single light chain variable domain derived from a single rearranged light chain variable region gene in the germline of the non-human animal, wherein the single rearranged light chain variable region gene comprises a substitution of at least one non-histidine encoding codon with a histidine encoding codon. Methods of making non-human animals that express antibodies comprising a histidine-containing universal light chain are provided.

44 Claims, 28 Drawing Sheets

(56) References Cited

U.S. PATENT DOCUMENTS

| | | |
|---|---|---|
| 2006/0141456 A1 | 6/2006 | Edwards et al. |
| 2006/0199204 A1 | 9/2006 | Dix et al. |
| 2007/0061900 A1 | 3/2007 | Murphy et al. |
| 2007/0280945 A1 | 12/2007 | Stevens et al. |
| 2008/0069822 A1 | 3/2008 | Jensen et al. |
| 2008/0078000 A1 | 3/2008 | Poueymirou et al. |
| 2009/0035836 A1 | 2/2009 | Datta et al. |
| 2009/0181855 A1 | 7/2009 | Vasquez et al. |
| 2010/0069614 A1 | 3/2010 | Houtzager et al. |
| 2010/0146647 A1 | 6/2010 | Logtenberg et al. |
| 2010/0310586 A1 | 12/2010 | Dolcetti et al. |
| 2010/0331527 A1 | 12/2010 | Davis et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0195454 A1 | 8/2011 | McWhirter et al. |
| 2011/0229489 A1 | 9/2011 | Pons et al. |
| 2012/0021409 A1 | 1/2012 | McWhirter et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2012/0322108 A1 | 12/2012 | Macdonald et al. |
| 2013/0011866 A1 | 1/2013 | Igawa et al. |
| 2013/0045492 A1 | 2/2013 | Babb et al. |
| 2013/0145484 A1 | 6/2013 | Logtenberg et al. |
| 2013/0185821 A1 | 7/2013 | Babb et al. |
| 2013/0247236 A1 | 9/2013 | McWhirter et al. |
| 2013/0302836 A1 | 11/2013 | McWhirter et al. |
| 2014/0013456 A1 | 1/2014 | McWhirter et al. |
| 2015/0059009 A1 | 2/2015 | McWhirter et al. |
| 2015/0119556 A1 | 4/2015 | McWhirter et al. |
| 2015/0250151 A1 | 9/2015 | McWhirter et al. |
| 2015/0313193 A1 | 11/2015 | McWhirter et al. |

FOREIGN PATENT DOCUMENTS

| | | |
|---|---|---|
| CN | 1560081 A | 1/2005 |
| EP | 1 317 537 A2 | 6/2003 |
| EP | 1 439 234 A1 | 7/2004 |
| EP | 1 605 058 B1 | 5/2009 |
| EP | 2 147 594 A1 | 1/2010 |
| EP | 2 275 443 A1 | 1/2011 |
| EP | 2 427 357 A | 3/2012 |
| EP | 2 501 817 A | 9/2012 |
| EP | 2 505 654 A1 | 10/2012 |
| EP | 2 517 556 A2 | 10/2012 |
| EP | 2 517 557 A2 | 10/2012 |
| EP | 2 556 747 A2 | 2/2013 |
| EP | 2 564 695 A1 | 3/2013 |
| EP | 2 582 230 A | 4/2013 |
| EP | 2762564 A1 | 8/2014 |
| WO | 92/03918 A1 | 3/1992 |
| WO | 94/02602 A1 | 2/1994 |
| WO | 96/34096 A1 | 10/1996 |
| WO | 98/46645 A1 | 10/1998 |
| WO | 98/50431 A2 | 11/1998 |
| WO | 02/20767 A2 | 3/2002 |
| WO | 02/36789 A2 | 5/2002 |
| WO | 2004/009618 A2 | 1/2004 |
| WO | 2004/106375 A1 | 12/2004 |
| WO | 2006/117699 A2 | 11/2006 |
| WO | 2007/117410 A2 | 10/2007 |
| WO | 2008/043822 A2 | 4/2008 |
| WO | 2008/054606 A2 | 5/2008 |
| WO | 2008/076379 A2 | 6/2008 |
| WO | 2008/112922 A2 | 9/2008 |
| WO | 2009/125825 A1 | 10/2009 |
| WO | 2009/157771 A2 | 12/2009 |
| WO | 2010/039900 A2 | 4/2010 |
| WO | 2010/070263 A1 | 6/2010 |
| WO | 2010/128897 A1 | 11/2010 |
| WO | 2011/004192 A1 | 1/2011 |
| WO | 2011/072204 A1 | 6/2011 |
| WO | 2011/097603 A1 | 8/2011 |
| WO | 2011097603 A1 | 8/2011 |
| WO | 2011/111007 A2 | 9/2011 |
| WO | 2011/122011 A2 | 10/2011 |
| WO | 2011/158009 A1 | 12/2011 |
| WO | 2011/163314 A1 | 12/2011 |
| WO | 2012/141798 A1 | 10/2012 |
| WO | 2012/148873 A2 | 11/2012 |
| WO | 2013022782 A1 | 2/2013 |
| WO | 2013/046722 A1 | 4/2013 |
| WO | 2013/079953 A1 | 6/2013 |
| WO | 2013/134263 A1 | 9/2013 |
| WO | 2013/184761 A1 | 12/2013 |
| WO | 2014/130690 A1 | 8/2014 |

OTHER PUBLICATIONS

International Search Report and Written Opinion mailed Sep. 4, 2013, from related International Patent Application No. PCT/US2013/044257 filed Jun. 5, 2013.

Arnold, L. et al., "Development of B-1 cells: Segregation of Phosphatidyl Choline-specific B Cells to the B-1 Population Occurs after Immunoglobulin Gene Expression," *J. Exp. Med.*, 179:1585-1595 (1994).

Aucouturier, P. et al., "Monoclonal Ig L chain and L chain V domain fragment crystallization in myeloma-associated Fanconi's syndrome," *J. Immunol.*, 150(8):3561-3568 (1993).

Auerbach, et al., "Establishment and Chimera Analysis of 129/SvEv- and C57BL/6-Derived Mouse Embryonic Stem Cell Lines", *BioTechniques*, 29:1024-1032 (2000).

Basu, S.K., "Receptor-mediated endocytosis: An overview of a dynamic process," *J. Biosci.*, 6(4):535-542 (Aug. 6, 1984).

Bauer, S. et al., "Structure and pre-B lymphocyte restricted expression of the VpreB gene in humans and conservation of its structure in other mammalian species," *The EMBO Journal*, 7(1):111-116 (1988).

Beguinot, L. et al. "Down-regulation of the epidermal growth factor receptor in KB cells is due to receptor internalization and subsequent degradation in lysosomes," *Proc. Natl. Acad. Sci. USA*, 81:2384-2388 (1984).

Brezinschek, H. et al., "Pairing of Variable Heavy and Variable κ Chains in Individual Naïve and Memory B Cells," *J. Immunol.*, 160(10):4762-4767 (1998).

Brown, M.S. et al., "Recycling Receptors: The Round-Trip Itinerary of Migrant Membrane Proteins," *Cell*, 22:663-667 (1983).

Carmack, C. et al., "Influence of a V kappa 8 L chain transgene on endogenous rearrangements and the immune response to the HA(Sb) determinant of influenza virus," *J. Immunol.*, 147(6):2024-2033 (1991).

Carter, P., "Bispecific human IgG by design," *Journal of Immunological Methods*, 248(1-2):7-15 (2001).

Cascalho, M. et al., "A Quasi-Monoclonal Mouse," *Science*, 272(5268):1649-1652 (1996).

Chaparro-Riggers, J. et al. "Increasing Serum Half-life and Extending Cholesterol Lowering in Vivo by Engineering Antibody with pH-sensitive Binding to PCSK9," *J. Biol. Chem.* 287(14):11090-11097 (2012).

Chinese Search Report for related Chinese Application No. 201180013714.0, mailed May 15, 2013.

Corbett, S.J. et al., "Sequence of the Human Immunoglobulin Diversity (D) Segment Locus: A Systematic Analysis Provides No Evidence for the Use of DIR Segments, Inverted D Segments, 'Minor' D Segments or D-D Recombination," *J. Mol. Biol.* 270:587-597 (1997).

Dall'Acqua W. F. et al., "Properties of Human IgG1s Engineered for Enhanced Binding to the Neonatal Fc Receptor (FcRn)," *J. Biol. Chem.*, 281:23514-23524 (2006).

Davies, et al., "Creation of Mice Expressing Human Antibody Light Chains by Introduction of a Yeast Artificial Chromosome Containing the Core Region of the Human Immunoglobulin κ Locus", *Nature Biotechnology*, 11:911-914, (1993).

de Kruif, J. et al., "Human Immunoglobulin Repertoires against Tetanus Toxoid Contain a Large and Diverse Fraction of High-Affinity Promiscuous VH Genes," *Journal of Molecular Biology*, 387:548-558 (2009).

(56) References Cited

OTHER PUBLICATIONS de Wildt, R. et al., "Analysis of heavy and light chain pairings indicates that receptor editing shapes the human antibody repertoire," *J. Mol. Biol.*, 285(3):895-901 (1999).
Deng, R. et al. "Pharmacokinetics of Humanized Monoclonal Anti-Tumor Necrosis Factor-α Antibody and Its Neonatal Fc Receptor Variants in Mice and Cynomolgus Monkeys," *Drug Metabolism and Disposition*, 38(4):600-605 (2010).
Desienhofer, J., "Crystallographic Refinement and Atomic Models of a Human Fc Fragment and Its Complex with Fragment B of Protein A from *Staphylococcus aureus* at 2.9- and 2.8-Å Resolution," *Biochemistry*, 20(9):2361-2370 (1981).
Donohoe, M. et al., "Transgenic Human λ5 Rescues the Murine Lambda5 Nullizygous Phenotype," *Journal of Immunology*, 164:5269-5276 (2000).
Dunn, K.W. et al., "Iterative Fractionation of Recycling Receptors from Lysosomally Destined Ligands in an Early Sorting Endosome," *J. Cell. Biol.*, 109(6/2):3303-3314 (1989).
Edwards, D.R., et al., "The ADAM Metalloproteinases", *Molecular Aspects of Medicine*, 29(5): 258-289 (2008).
European Examination for Application No. 11 703 799.4 mailed Oct. 9, 2012.
European Communication for Application No. 12 173 456.0 mailed Dec. 5, 2012.
European Search Report for Application No. 12 173 456.0 dated Aug. 10, 2012.
Fallon, E.M. et al., "Increased Endosomal Sorting of Ligand to Recycling Enhances Potency of an Interleukin-2 Analog," *J. Biol. Chem.* 275(10):6790-6797 (2000).
Featherstone, K., et al., "The Mouse Immunoglobulin Heavy Chain V—D Intergenic Sequence Contains Insulators That May Regulate Ordered V(D)J Recombination", *The Journal of Biological Chemistry*, 285(13):9327-9338 (2010).
Festing, et al., "Revised nomenclature for strain 129 mice," *Mammalian Genome*, 10:836 (1999).
Fraenkel, S. et al., "Allelic 'choice' governs somatic hypermutation in vivo at the immunoglobulin kappa-chain locus," *Nat. Immunol.*, 8(7):715-722 (2007).
Gan, Z. et al.,"Analyses of the recycling receptor, FcRn, in live cells reveal novel pathways for lysosomal delivery," *Traffic*, 10(5):600. (2009).
Gay, D. et al., "Receptor editing: an approach by autoreactive B cells to escape tolerance," *J. Exp. Med.*, 177(4):999-1008 (1993).
Giallourakis, C.C., et al., "Elements between the IgH variable (V) and diversity (D) clusters influence antisense transcription and lineage-specific V(D)K recombination," *PNAS*, 107(51):22207-22212 (2010).
Goldstein, J.L. et al., "The LDL Receptor," *Arterioscler. Thromb. Vasc. Biol.*, 29:431-438 (2009).
Goletz et al., "Selection of Large Diversities of Antiidiotypic Antibody Fragments by Phage Display", *J. Mol. Biol.*, 315:1087-97, (2002).
Gonnet, et al., "Exhaustive Matching of the Entire Protein Sequence Database," *Science*, 256:1443-1445 (1992).
Gonzalez-Fernandez, A. et al., "Analysis of somatic hypermutation in mouse Peyer's patches using immunoglobulin κ light-chain transgenes," *PNAS USA*, 90:9862-9866 (1993).
Goyenechea, B. et al., "Modifying the sequence of an immunoglobulin V-gene alters the resulting pattern of hypermutation," *PNAS USA*, 93:13979-13984 (1996).
Green, L. et al., "Antigen-specific human monoclonal antibodies from mice engineered with human Ig heavy and light chain YACs," *Nat. Genetics.*, 7(1):13-21 (1994).
Green, L. et al., "Regulation of B cell development by variable gene complexity in mice reconstituted with human immunoglobulin yeast artificial chromosomes," *J. Exp. Med.*, 188(3):483-495 (1998).
Han, C., et al., "Comprehensive Analysis of Reproductive ADAMs: Relationship of ADAM4 and ADAM6; with an ADAM Complex Required for Fertilization in Mice", *Biology of Reproduction*, 80(5): 1001-1008 (2009).

Hengstschlager, M. et al., "A λ1 transgene under the control of a heavy chain promoter and enhancer does not undergo somatic hypermutation," *Eur. J. Immunol.*, 24:1649-1656 (1994).
Hendricks, J., et al., "Organization of the variable region of the immunoglobin heavy-chain gene locus of the rat," *Immunogenetics*, 62:479-486 (2010).
Hochedlinger, et al., "Monoclonal Mice Generated by Nuclear Transfer from Mature B and T Donor Cells", *Nature* 415(6875):1035-1038, (2002).
Igawa, T. et al., "Reduced elimination of IgG antibodies by engineering the variable region," *Protein Engineering, Design & Selection*, 23(5):385-392 (2010).
Igawa, T. et al., "Antibody recycling by engineered pH-dependent antigen binding improves the duration of antigen neutralization," *Nature Biotechnology*, 28(11):1203-1208 and supplement (2010).
Igawa T. et al, "Engineering the variable region of therapeutic IgG antibodies," *mAbs*, 3(3):243-52. (2011).
International Search Report and Written Opinion for International Patent Application Serial No. PCT/US2011/023971 dated Apr. 11, 2011.
International Search Report and Written Opinion for International Patent Application Serial No. PCT/US2012/034737 mailed Dec. 6, 2012.
International Search Report and Written Opinion for International Patent Application Serial No. PCT/US2012/049600 mailed Nov. 23, 2012.
International Search Report and Written Opinion for International Patent Application Serial No. PCT/US2013/029125 mailed Jun. 20, 2013.
International Search Report and Written Opinion for International Patent Application Serial No. PCT/US2013/031834 mailed Jul. 2, 2013.
International Search Report and Written Opinion for International Patent Application Serial No. PCT/US2013/032036 mailed Jul. 1, 2013.
International Search Report and Written Opinion for International Patent Application Serial No. PCT/US2013/031823 mailed Jul. 8, 2013.
Ippolito, G.C., "Forced usage of positively charged amino acids in immunoglobulin CDR-H3 impairs B cell development and antibody production," *J. Exp. Med.*, 203(6):1567-1578 (2006).
Ito, W. et al., The His-probe method: effects of histidine residues introduced into the complementary-determining regions of antibodies on antigen-antibody interactions at different pH values, *FEBS Lett.*, 309(1):85-88. (1992).
Jakobovits, A. et al., "From XenoMouse technology to panitumumab, the first fully human antibody product from transgenic mice," *Nature Biotechnology*, vol. 25, No. 10, pp. 1134-1143 (2007).
Jolly, C. et al., "Rapid methods for the analysis of immunoglobulin gene hypermutation: application to transgenic and gene targeted mice," *Nucleic Acids Research*, 25(10):1913-1919 (1997).
Kim, T., et al., "Expression and relationship of mail reproductive ADAMs in mouse," *Biology of Reproduction*, 74:744-750 (2006).
Klotz, E. et al., "Somatic Hypermutation of a $\lambda_2$ Transgene Under the Control of the λ Enhancer or the Heavy Chain Intron Enhancer," *J. Immunol.*, 157:4458-4463 (1996).
Klotz, E. et al., "Somatic Hypermutation of an Artificial Test Substrate Within an IDκ Transgene," *J. Immunol.*, 161:782-790 (1998).
Kong, Q. et al., "A λ 3' enhancer drives active and untemplated somatic hypermutation of a $\lambda_1$ transgene," *J. Immunol.*, 161:294-301 (1998).
Kufer, P. et al., "A revival of bispecific antibodies," *Trends Biotechnol.*, 22(5):238-244 (May 2004).
Lee, E-C., et al., "The application of transgenic mice for therapeutic antibody discovery," *Methods in Molecular Biology*, 901:137-148 (2012).
Lencer, W. I. et al., "A passionate kiss, then run: exocytosis and recycling of IgG by FcRn," *Trends in Cell Biol.*, 15(1):5-9 (2005).
Lefranc, M., "Nomenclature of the Human Immunoglobulin Genes," *Current Protocols in Immunology*, Supplement 40, pp. A.1P.1-A.1P.37 (2001).

(56) References Cited

OTHER PUBLICATIONS

Lefranc, et al. "IMGT unique numbering for immunoglobulin and T cell receptor variable domains and Ig superfamily V-like domains," *Dev. Comp. Immunol.*, 27:55-77 (2003).
Leitzgen, K. et al., "Assembly of immunoglobulin Light Chains as a Prerequisite for Secretion," *Journal of Biological Chemistry*, 272(5): 3117-3123 (1997).
Lindhofer, H. et al., "Preferential Species-Restricted Heavy/Light Chain Pairing in Rat/Mouse Quadromas," *The Journal of Immunology*, 155:219-225 (1995).
Lonberg et al., "Antigen-specific Human Antibodies from Mice Comprising Four Distinct Genetic Modifications", *Nature*, 368:856-859, (1994).
Lonberg, N., "Human antibodies from transgenic animals," *Nature Biotechnology*, 23(9):1117-1125 (2005).
Maeda, K. et al., "pH-dependent receptor/ligand dissociation as a determining factor for intracellular sorting of ligands for epidermal growth factor receptors in rat hepatocytes," *J. Controlled Release*, 82:71-82. (2002).
Marvin, J. et al., "Recombinant approaches to IgG-like bispecific antibodies," *Acta Pharmacologica Sinica*, 26(6):649-658 (2005).
Mellman, I., "The Importance of Being Acidic: The Role of Acidification in Intracellular Membrane Traffic," *J. Exp. Biol.*, 172:39-45 (1992).
Mendez, M. J. et al., "Functional Transplant of Megabase Human Immunoglobulin Loci Recapitulates Human Antibody Response in Mice," *Nat. Genetics*, 15(2):146-156 (1997).
Merchant, A. et al., "An efficient route to human bispecific IgG," *Nature Biotechnology*, 16(7):677-681 (1998).
Moran, Nuala "Mouse Platforms Jostle for Slice of Humanized Antibody Market", *Nature Biotech*, 3:267-268, (2013).
Murtaugh, M.L. et al., "A combinatorial histidine scanning library approach to engineer highly pH-dependent protein switches," *Protein Sci.*, 20(9):1619-1631 (2011).
Nakasako, M. et al., "The pH-dependent Structural Variation of Complementarity-determining Region H3 in the Crystal Structures of the Fv Fragment from an Anti-dansyl Monoclonal Antibody," *J. Mol. Biol.*, 291:117-134 (1999).
Nicholson, I. et al., "Antibody Repertoires of Four- and Five-Feature Translocus Mice Carrying Human Immunoglobulin Heavy Chain and κ and λ Light Chain Yeast Artificial Chromosomes," *Journal of Immunology*, 163:6898-6906 (1999).
O'Brien, R. et al., "Somatic hypermutation of an immunoglobulin transgene in κ mice," *Nature*, 326(6111):405-409 (1987).
Pelanda, R. et al., "A prematurely Expressed Igκ Transgene, but Not VκJκ Gene Aegment Targeted into the Igκ Locus, Can Rescue B Cell Development in λ5-Deficient Mice," *Immunity*, 5(3):229-239 (1996).
Petkova, S.B. et al., "Enhanced half-life of genetically engineered human IgG1 antibodies in a humanized FcRn mouse model: potential application in humorally mediated autoimmune disease," *Intl. Immunol.*, 18(12):1759-1769 (2006).
Poueymirou, W. et al. F0 generation mice that are essentially fully derived from the donor gene-targeted ES cells allowing immediate phenotypic analyses, *Nature Biotech.*, 25(1):91-99 (2007).
Prak, E. et al., "Light chain replacement: a new model for antibody gene rearrangement," *J. Exp. Med.*, 182(2):541-548 (1995).
Presta, L.G., "Molecular engineering and design of therapeutic antibodies," *Curr. Opin. Immunol.*, 20(4):460-470 (2008).
Raso, V. et al., "Intracellular Targeting with Low pH-triggered Bispecific Antibodies," *J. Biol. Chem.*, 272(44):27623-27628 (1997).
Roberts, D.M. et al., "Isolation and Characterization of the Fc Receptor from Fetal Yolk Sac of the Rat," *J. Cell. Biol.*, 111:1867-1876 (1990).
Rojas, G. et al., "Phage antibody fragments library combining a single human light chain variable region with immune mouse heavy chain variable regions," *Journal of Biotechnology*, 94:287-298 (2002).
Roopenian, D.C, et al., "FcRn: the neonatal Fc receptor comes of age," *Nature Rev. Immunol.*, 7:715-725 (Sep. 2007).

Roopenian, D.C., et al., "Clinical Ramifications of the MHC Family Fc Receptor FcRn," *J. Clin. Immunol.*, 30(6):790-797 (2010).
Sarkar, C.A. et al. "Rational cytokine design for increased lifetime and enhanced potency using pH-activated 'histidine switching'," *Nature Biotech.*, 20:908-913 (2002).
Schroeder, H.W., et al., "Similarity and divergence in the development and expression of the mouse and human antibody repertoires," *Developmental and Comparative Immunol.*, 30(1-2):119-135 (2006).
Seals, D.F., et al., "The ADAMs family of metalloproteases: multidomain; proteins with multiple functions," *Genes and Development*, 17(1):7-30 (2003).
Simister, Neil E., et al. An Fc receptor structurally related to MHC class I antigens, *Nature* 337:184-187 (Jan. 12, 1989).
Sirac, C. et al., "Role of the monoclonal kappa chain V domain and reversibility of renal damage in a transgenic model of acquired Fanconi syndrome," *Blood*, 108(2):536-543 (2006).
Smith, B. et al., "The unique and immunoglobulin-like regions of surrogate light chain component lambda5 differentially interrogate immunoglobulin heavy-chain structure," *Molecular Immunology*, 47:1195-1206 (2010).
Storb, et al., "Transgenic Mice with μ and κ Genes Encoding Antiphosphorycholine Antibodies", *J. Exp Med*, 164:627-641 (1986).
Suzuki, T. et al., "Importance of Neonatal FcR in REgulation the Serum Half-Life of Therapeutic Proteins Containing the Fc Domain of Human IgG1: A Comparative Study of the Affinity of Monoclonal Antibodies and Fc-Fusion Proteins to Human Neonatal FcR," *J. Immunol.*, 184:1968-1976 (2010).
Reply to Third Party Observations on European patent application 11 703 799.04 (Publication No. EP 2 501 817) filed in EPO on May 20, 2013.
Request to provoke an interference U.S. Appl. No. 13/750,753 Jan. 25, 2013.
Summons to attend oral proceedings arranged in connection with European patent application 09075279.1 (Publication No. EP 2 147 594 A1) mailed Mar. 6, 2013.
Tabrizi, M. A. et al. "Elimination mechanisms of therapeutic monoclonal antibodies," *Drugs Discovery Today*, 11(1/2):81-88 (2006).
Taylor et al., "A Transgenic Mouse that Expresses a Diversity of Human Sequence Heavy and Light Chain Immunoglobulins," *Nucleic Acid Research*, 20(23):6287-6295 (1992).
Taylor et al., "Human immunoglobulin transgenes undergo rearrangement, somatic mutation and class switching in mice that lack endogenous IgM", *Int. Immunol.*, 6:579-591 (1994).
Third Party Observations Under Article 115 EPC against European Parent Application No. 09075279.1 filed in EPO on Oct. 25, 2012.
Third Party Observations on European patent application 11 703 799.4-2405 (Publication No. EP 2 501 817) mailed on Feb. 28, 2013.
Tsubata, T. et al., "The Products of the Pre-B Cell-specific Genes(Lambda5 and VpreB) and the Immunoglobulin mu Chain Form a Complex that is Transported onto the Cell Surface," *Journal of Experimental Medicine*, 172:973-976 (1990).
Tuaillon, et al., "Analysis of direct and inverted DJH rearrangements in a human Ig heavy chain transgenic minilocus," *Journal of Immunology*., 154(12):6453-6465 (1995).
Tutt, A. et al., "Trispecific F(ab')3 Derivatives That Use Cooperative Signaling Via the TCR/CD3 Complex and CD2 to Activate and Redirect Resting Cytotoxic T Cells," *Journal of Immunology*, 147(1):60-69 (Jul. 1, 1991).
Tzaban, S. et al., "The recycling and transcytotic pathways for IgG transport by FcRn are distinct and display an inherent polarity," *J. Cell Biol.*, 185(4):673-684 (2009).
Valenzuela, D. M. et al., "High-throughput engineering of the mouse genome coupled with high-resolution expression analysis," *Nature Biotech.*, 21(6):652-659 (2003).
Vaughn, D.E., et al., "Structural basis of pH-dependent antibody binding by the neonatal receptor," *Structure*, 6:63-73(1997).
Wang, W. et al. "Monoclonal Antibody Pharmacokinetics and Pharmacodynamics," *Clinical Pharmacology & Therapeutics*, 84(5):548-558 (2008).

(56) References Cited

OTHER PUBLICATIONS

Watanabe, H. et al. "Optimizing pH Response of Affinity between Protein G and IgG Fc: How Electrostatic Modulations Affect Protein-Protein Interactions," *J. Biol. Chem.*, 284(18):12373-12383 (2009).
Xu, L. et al., "Combinatorial surrobody libraries," *Proceedings of the National Academy of Sciences (USA)*, 105(31):10756-10761 (2008).
Yeung, Y.A. et al. "Engineering Human IgG1 Affinity to Human Neonatal Fc Receptor: Impact of Affinity Improvement on Pharmacokinetics in Primates," *J. Immunol.*, 182(12):7663-7671 (2009).
U.S. Non-Final Office Action for U.S. Appl. No. 13/022,759 mailed Sep. 7, 2012.
U.S. Non-Final Office Action for U.S. Appl. No. 13/093,156 mailed Sep. 6, 2012.
U.S. Non-Final Office Action for U.S. Appl. No. 13/412,936 mailed Sep. 6, 2012.
Aucouturier et al., (1992) "Human rearranged IgK mRNA VJC region," GenBank Accession No. M87478 1 page, first referenced Mar. 3, 1992, first seen at NCBI Apr. 27, 1993.
Choi et al., (2004) "Characterization and comparative genomic analysis of intronless Adams with testicular gene expression," Genomics 83(4):636-646.
Dechiara et al., (2009) Chapter 16: VelociMouse: Fully ES Cell-Derived FO Generation Mice Obtained from the Injection of ES Cells into 8-Cell Stage Embryos, Gene Knockout Protocols: Second Edition, vol. 530, Humana Press.
Fishwild et al., (1996) "High-avidity human IgGk monoclonal antibodies from a novel train of mililocus transgenic mice," Nature Biotechnology, 14(7):845-851.
Goodhardt et al., (1987), "Rearrangement and Expression of rabbit immunoglobulin K light chain gene in transgenic mice," PNAS, 84:4229-4233.
Goyenechea et al., (1997) "Cells strongly expressing Ig(kappa) transgenes show clonal recruitment of hypermutation: a role for both MAR and the enhancers," EMBO J., 16(13):3987-3994.
Hardy and Hayakawa, (2001) "B cell development pathways," Annu. Rev. Immunol., 19:595-621.
Hömig-Hölzel et al., (2008) "Constitutive CD40 signaling in B cells selectively activates the noncanonical NF-kappaB pathway and promotes lymphomagenesis," J. Exp. Med., 205(6):1317-1329.
Inlay et al., (2002) "Essential roles of the kappa light chain intronic enhancer and 3' enhancer in kappa rearrangement and demethylation," Nat. Immunol., 3(5):463-468.
Jakobovits, (1995) "Production of fully human antibodies by transgenic mice," Curr. Opin. Biotechnol., 6(5):561-566.
Janeway's Immunobiology, (2008) Seventh Edition, Murphy, Travers and Walport, eds., Garland Science, New York and London, Ch. 4, pp. 145-155.
Kabat and Wu, (1991) "Identical V region amino acid sequences and segments of sequences in antibodies of different specificities. Relative contributions of VH and VL genes, minigenes, and complementarity-determining regions to binding of antibody-combining sites," J. Immunol., 147(5):1709-1719.
Kaushik, (1990) "Stochastic pairing of heavy-chain and x light-chain variable gene families occurs in polyclonally activated B cells," Proc. Natl. Acad. Sci. USA, 87:4932-4936.
Klöhn et al., (2013) "IBC's 23rd Annual Antibody Engineering, 10th Annual Antibody Therapeutics international conferences and the 2012 Annual Meeting of the Antibody Society: Dec. 3-6, 2012," San Diego, CA, Mabs, 5(2):178-201.
Logtenberg, (2007) "Antibody cocktails: next-generation biopharmaceuticals with improved potency," Trends Biotechnol., 25(9):390-394.
Nagle, (2007) "Regeneron helps make Sanofi VelocImmune to its "weak pipeline,""http://www.outsourcing-pharma.com>—Published Dec. 3, 2007.
Nemazee, (2006) "Receptor editing in lymphocyte development and central tolerance," Nat. Rev. Immunol., 6(10):728-740.
News in Brief Article (2007) "Big Pharma vies for mice," Nature Biotechnology, 25(6):613—Published Jun. 2007.
No Author Listed, Additional post-filing data and letter filed by the Applicant/Patentee for corresponding European application 09075279.1, now opposed patent EP 2147594 B1, 4 pages (Jun. 13, 2013).
No Author Listed, "Next generation transgenic mice for therapeutic human antibodies, Description of MeMoTM," filed by the Applicant/Patentee in prosecution for corresponding European application 09075279.1, now opposed patent EP 2147594 B1, 2 pages (Dec. 22, 2011).
No Author Listed, (2011) Chapter 8: The Development and Survival of Lymphocytes, Janeway's Immunobiology, 8th Edition, Eds. Kenneth Murphy et al, Garland Science (ISBN: 9780815342434), whole document, in particular p. 279 and Figure 8.4.
Orban et al., (1992) "Tissue- and site-specific DNA recombination in transgenic mice," Proc. Natl. Acad. Sci. U S A., 89(15):6861-6865.
Popov et al., (1999) "A human immunoglobulin lambda locus is similarly well expressed in mice and humans," J. Exp. Med., 189(10):1611-1620.
Rabquer et al., (2005) "Immunoglobulin light chain variable region, partial [*Homo sapiens*]," GenBank Accession No. ABA26122, 2 pages, first reference Dec. 31, 1995.
Rickert et al., (1997) "B lymphocyte-specific, Cre-mediated mutagenesis in mice," Nucleic Acids Res., 25(6):1317-1318.
Sasaki et al., (2006) "Canonical NF-x13 Activity, Dispensable for B Cell Development, Replaces BAFF-Receptor Signals and Promotes B Cell Proliferation upon Activation," Immunity, 24:729-739.
Scott, (2007) "Mice with a human touch," Nature Biotechnology, 25(10):1075-1077.
Sharpe et al., (1991) "Somatic hypermutation of immunoglobulin kappa may depend on sequences 3' of C kappa and occurs on passenger transgenes," EMBO J., 10(8):2139-2145.
Simon and Rajewsky, (1990), "Antibody domain mutants demonstrate autonomy of the antigen binding site," EMBO J., 9(4):1051-1056.
Soriano, (1999) "Generalized lacZ expression with the ROSA26 Cre reporter strain," Nat. Genet., 21(1):70-71.
Stevens et al., (2008) "Human Antibody Discovery, VelocImmune—A novel platform, Pharma Focus Asia," Issue 8:72-74.
Torres and Kuhn, (1997) "Laboratory Protocols for Conditional Gene Targeting," Oxford University Press, 978-0-19-963677-8, 42-53.
Vaughan et al., (1996) "Human antibodies with sub-nanomolar affinities isolated from a large non-immunized phage display library," Nat. Biotechnol., 14(3):309-314.
Winter et al., (1997) "Insertion of 2 kb of bacteriophage DNA between an immunoglobulin promoter and leader exon stops somatic hypermutation in a kappa transgene," Mol. Immunol., 34(5):359-366.
International Search Report and Written Opinion for PCT Application No. PCT/US2013/044257 mailed Sep. 4, 2013 (9 pages).
International Search Report and Written Opinion for PCT Application No. PCT/US2014/025982 mailed Jul. 22, 2014 (13 pages).
International Search Report and Written Opinion for PCT Application No. PCT/US2014/026040 mailed Jul. 29, 2014 (14 pages).
International Search Report and Written Opinion for PCT Application No. PCT/US2014/056285 mailed Feb. 2, 2015 (12 pages).
Sirac et al. (2011) "Toward Understanding Renal Fanconi Syndrome: Step by Step Advances through Experimental ModeLs," Exp. Models for Renal Diseases: Pathogenesis and Diagnosis, Contrib. Nephrol. Basel, Karger, 169:247-261.
Statement of Relatedness under MPEP 2001.06 dated Sep. 4, 2015.
Bot et al., (1996) "Vλ-Light Chain Genes Reconstitute Immune Responses to Defined Carbohydrate Antigens or Haptens by Utilizing Different VH Genes," Molecular Immunology, 33(17/18):1359-1368.
Bruggemann (1997) "The Preparation of Human Antibodies from Mice Harbouring Human Immunoglobulin Loci," (Edited by L. M. Houdebine) Transgenic Animals: Generation and Use, Amsterdam: Harwood Acedemic Publishers, pp. 397-403.

(56) References Cited

OTHER PUBLICATIONS

Chen et al., (1994) "Deletion and Editing of B Cells that Express Antibodies to DNA," Journal of Immunology, 152:1970-1982.

Hartley and Goodnow (1993) "Censoring of self-reactive B cells with a range of receptor affinities in transgenic mice expressing heavy chains for a lysozyme-specific antibody," International Immunology, 6(9):1417-1425.

Phan et al. (2003) "B Cell Receptor-independent Stimuli Trigger Immunoglobulin (Ig) Class Switch Recombination and Production of IgG Autoantibodies by Anergic Self-Reactive B Cells," J. Exp. Med., 197(7):845-860.

Phan et al. (2005) "Altered Migration, Recruitment, and Somatic Hypermutation in the Early Response of Marginal Zone B Cells to T Cell-Dependent Antigen," J. Immunology, 174:4567-4578.

Phan et al. (2006) "High affinity germinal center B cells are actively selected into the plasma cell compartment," JEM, 203(11):2419-2424.

Ritchie et al. (1984) "Allelic exclusion and control of endogenous immunologlobulin gene rearrangement in κ transgenic mice," Nature, 312:517-520.

Tiegs et al. (1993) "Receptor Editing in Self-reactive Bone Marrow B Cells," J. Exp. Med., 177:1009-1020.

Xu and Davis (2000) "Diversity in the CDR3 Region of VH is Sufficient for Most Antibody Specificities," Immunity, 13:37-45.

* cited by examiner

```
            |-------FR1-IMGT--------||--CDR1||----FR2-IMGT----||C||----
            DIQMTQSPSSLSASVGDRVTITCRASQSISSYLNWYQQKPGKAPKLLIYAASSLQSGVPS
IGKV1-39*01
         A   .A..................F..T.H...........I......V..YT.....
         B   ....................................I.NF........G.YN....
         C   ..........................HN.NN....H.......N.............
         D   .........................................................
         E   ..................A........A....T.N.......................
         F   .........................................................
         G   .A..L.....................................N.....D........
         H   .A..L.....................................N.....D........
         I   .A..L..................N.N..H............................
         J   .A..L..............................................D..F..
         K   .A.................................................M.....

------FR3-IMGT----------||CDR3-|
            RFSGSGSGTDFTLTISSLQPEDFATYYCQQSYST-P----------
         A  ...A........................T...NI..FTFGPGTKVDIKR-----        SEQ ID NO:1
         B  .............................I....H-----LTFGGGTKVEIKR         SEQ ID NO:82
         C  ..........Y........T.H...GN..........SMYTFGQGTQLEIKR           SEQ ID NO:83
         D  ..............................I...ITFGQGTRLEIKR               SEQ ID NO:84
         E  .............................H....H.ITFGQGTRLEIKR             SEQ ID NO:85
         F  .....................T.H...........H.ITFGQGTRLEIKR            SEQ ID NO:86
         G  .....................T.............H.ITFGQGTRLEIKR            SEQ ID NO:87
         H  ....................................H.ITFGQGTRVEIKR           SEQ ID NO:88
         I  ..........K........................P.ITFGQGTRVEIKR             SEQ ID NO:89
         J  ....................................IH.ITFGQGTKLEIKR          SEQ ID NO:90
         K  ...................................H.IP.ITFGQGTRLEIK.         SEQ ID NO:91
         L  ..........T......R.................H..P.ITFGQGTKVEIKR         SEQ ID NO:92
```

FIG. 1

|  | 105 | 106 |  | 108 |  |  | 111 |  |
|---|---|---|---|---|---|---|---|---|
|  | Q | Q | S | Y | S | T | P |  |
| WT | CAG | CAG | AGC | TAC | AGC | ACC | CCC | SEQ ID NO:3<br>SEQ ID NO:2 |
|  | H |  |  | H |  |  | H |  |
| H105/106/108/111 | CAC | CAT | AGC | CAC | AGC | ACC | CAC | SEQ ID NO:5<br>SEQ ID NO:4 |
| H105 | CAC | CAG | AGC | TAC | AGC | ACC | CCC | SEQ ID NO:6 |
| H106 | CAG | CAT | AGC | TAC | AGC | ACC | CCC | SEQ ID NO:8 |
| H108 | CAG | CAG | AGC | CAC | AGC | ACC | CCC | SEQ ID NO:10 |
| H111 | CAG | CAG | AGC | TAC | AGC | ACC | CAC | SEQ ID NO:12 |
| H105/106 | CAC | CAT | AGC | TAC | AGC | ACC | CCC | SEQ ID NO:14 |
| H105/108 | CAC | CAG | AGC | CAC | AGC | ACC | CCC | SEQ ID NO:16 |
| H105/111 | CAC | CAG | AGC | TAC | AGC | ACC | CAC | SEQ ID NO:18 |
| H106/108 | CAG | CAT | AGC | CAC | AGC | ACC | CCC | SEQ ID NO:20 |
| H106/111 | CAG | CAT | AGC | TAC | AGC | ACC | CAC | SEQ ID NO:22 |
| H108/111 | CAG | CAG | AGC | CAC | AGC | ACC | CAC | SEQ ID NO:24 |
| H105/106/108 | CAC | CAT | AGC | CAC | AGC | ACC | CCC | SEQ ID NO:26 |
| H105/106/111 | CAC | CAT | AGC | TAC | AGC | ACC | CAC | SEQ ID NO:28 |
| H105/108/111 | CAC | CAG | AGC | CAC | AGC | ACC | CAC | SEQ ID NO:30 |
| H106/108/111 | CAG | CAT | AGC | CAC | AGC | ACC | CAC | SEQ ID NO:32 |

FIG. 2

| Heavy Chain | Light Chain Mutant | Kinetics at pH 7.4 | | | | | | Kinetics at pH 5.75 | | | | | | Ratio of low pH / neutral pH | | |
|---|---|---|---|---|---|---|---|---|---|---|---|---|---|---|---|---|
| | | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 1 | H105 | 488 | 47.2 | 3.52E+05 | 9.30E-03 | 2.64E-08 | 1.2 | 378 | 37.8 | 4.24E+05 | 1.38E-02 | 3.24E-08 | 0.8 | 1.2 | 1.5 | 1.2 |
| | H106 | 620 | 73.7 | 3.22E+05 | 3.67E-03 | 1.14E-08 | 3.1 | 505 | 65.4 | 3.66E+05 | 4.86E-03 | 1.33E-08 | 2.4 | 1.1 | 1.3 | 1.2 |
| | H108 | 648 | 99.0 | 3.17E+05 | 2.07E-03 | 6.54E-09 | 5.6 | 496 | 80.7 | 3.59E+05 | 3.02E-03 | 8.41E-09 | 3.8 | 1.1 | 1.5 | 1.3 |
| | H111 | 669 | 81.0 | 3.01E+05 | 3.81E-03 | 1.27E-08 | 3.0 | 536 | 62.8 | 3.32E+05 | 5.41E-03 | 1.63E-08 | 2.1 | 1.1 | 1.4 | 1.3 |
| | H105/106 | 492 | 55.6 | 3.74E+05 | 6.44E-03 | 1.72E-08 | 1.8 | 404 | 45.7 | 4.30E+05 | 1.01E-02 | 2.34E-08 | 1.1 | 1.2 | 1.6 | 1.4 |
| | H105/108 | 538 | 75.2 | 3.28E+05 | 4.17E-03 | 1.27E-08 | 2.8 | 416 | 56.3 | 3.87E+05 | 7.43E-03 | 1.92E-08 | 1.6 | 1.2 | 1.8 | 1.5 |
| | H105/111 | 501 | 44.6 | 3.44E+05 | 9.77E-03 | 2.84E-08 | 1.2 | 402 | 31.9 | 4.06E+05 | 1.70E-02 | 4.19E-08 | 0.7 | 1.2 | 1.7 | 1.5 |
| | H106/108 | 494 | 64.9 | 3.36E+05 | 4.14E-03 | 1.23E-08 | 2.8 | 407 | 43.0 | 4.07E+05 | 1.17E-02 | 2.86E-08 | 1.0 | 1.2 | 2.8 | 2.3 |
| | H106/111 | 536 | 78.2 | 3.09E+05 | 3.10E-03 | 1.00E-08 | 3.7 | 423 | 61.4 | 3.62E+05 | 4.68E-03 | 1.29E-08 | 2.5 | 1.2 | 1.5 | 1.3 |
| | H108/111 | 584 | 78.5 | 3.11E+05 | 3.80E-03 | 1.22E-08 | 3.0 | 473 | 59.0 | 3.50E+05 | 6.13E-03 | 1.75E-08 | 1.9 | 1.1 | 1.6 | 1.4 |
| | H105/106/108 | 442 | 51.2 | 3.72E+05 | 6.38E-03 | 1.71E-08 | 1.8 | 370 | 28.4 | 4.26E+05 | 2.13E-02 | 5.00E-08 | 0.5 | 1.1 | 3.3 | 2.9 |
| | H105/106/111 | 473 | 62.8 | 3.40E+05 | 4.55E-03 | 1.34E-08 | 2.5 | 378 | 47.6 | 4.07E+05 | 7.42E-03 | 1.82E-08 | 1.6 | 1.2 | 1.6 | 1.4 |
| | H105/108/111 | 433 | 49.5 | 3.57E+05 | 7.42E-03 | 2.08E-08 | 1.6 | 354 | 31.3 | 4.09E+05 | 1.73E-02 | 4.23E-08 | 0.7 | 1.1 | 2.3 | 2.0 |
| | H106/108/111 | 491 | 66.6 | 3.44E+05 | 3.82E-03 | 1.11E-08 | 3.0 | 415 | 43.3 | 3.91E+05 | 1.06E-02 | 2.72E-08 | 1.1 | 1.1 | 2.8 | 2.5 |
| | H105/106/108/111 | 454 | 57.9 | 3.51E+05 | 5.77E-03 | 1.64E-08 | 2.0 | 368 | 36.8 | 4.06E+05 | 1.35E-02 | 3.32E-08 | 0.9 | 1.2 | 2.3 | 2.0 |
| | ULC + Heavy | 586 | 76.0 | 3.16E+05 | 3.85E-03 | 1.22E-08 | 3.0 | 483 | 66.5 | 3.45E+05 | 4.58E-03 | 1.33E-08 | 2.5 | 1.1 | 1.2 | 1.1 |
| | Heavy only | 141 | -1.3 | NB | NB | NB | NB | 107 | -6.7 | NB | NB | NB | NB | Negative Control | | |
| | No DNA | 60 | -1.5 | NB | NB | NB | NB | 26 | -7.2 | NB | NB | NB | NB | | | |

FIG. 5A

| Heavy Chain | Light Chain Mutant | Kinetics at pH 7.4 | | | | | | Kinetics at pH 5.75 | | | | | | Ratio of low pH / neutral pH | | |
|---|---|---|---|---|---|---|---|---|---|---|---|---|---|---|---|---|
| | | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 2 | H105 | 720 | 33.7 | 1.02E+05 | 9.10E-04 | 8.89E-09 | 12.7 | 595 | 0.3 | NB | NB | NB | NB | No binding at Low pH | | |
| | H106 | 735 | 32.9 | 9.11E+04 | 4.47E-04 | 4.91E-09 | 25.8 | 623 | 4.3 | 2.27E+04 | 6.41E-03 | 2.82E-07 | 1.8 | 0.2 | 14.3 | 57.4 |
| | H108 | 728 | 32.2 | 8.48E+04 | 2.67E-04 | 3.14E-09 | 43.3 | 598 | 3.6 | 1.16E+03 | 3.41E-03 | 2.93E-06 | 3.4 | 0.0 | 12.8 | 933.1 |
| | H111 | 802 | 42.4 | 1.17E+05 | 1.15E-04 | 9.88E-10 | 100.3 | 670 | 14.1 | 3.01E+04 | 7.08E-04 | 2.35E-08 | 16.3 | 0.3 | 6.1 | 23.8 |
| | H105/106 | 570 | 24.9 | 8.51E+04 | 2.92E-04 | 3.43E-09 | 39.5 | 484 | 2.4 | 1.14E+04 | 6.47E-03 | 5.69E-07 | 1.8 | 0.1 | 22.1 | 165.9 |
| | H105/108 | 723 | 28.4 | 8.73E+04 | 1.30E-03 | 1.49E-08 | 8.9 | 603 | -2.6 | NB | NB | NB | NB | No binding at Low pH | | |
| | H105/111 | 627 | 28.5 | 8.82E+04 | 3.60E-04 | 4.08E-09 | 32.1 | 519 | 2.3 | 1.02E+04 | 1.30E-02 | 1.27E-06 | 0.9 | 0.1 | 36.2 | 311.3 |
| | H106/108 | 550 | 21.1 | 6.75E+04 | 9.12E-04 | 1.35E-08 | 12.7 | 470 | -1.9 | NB | NB | NB | NB | No binding at Low pH | | |
| | H106/111 | 808 | 32.7 | 9.01E+04 | 6.78E-04 | 7.52E-09 | 17.0 | 678 | 0.9 | NB | NB | NB | NB | No binding at Low pH | | |
| | H108/111 | 801 | 40.5 | 1.17E+05 | 9.80E-05 | 8.40E-10 | 117.8 | 676 | 10.6 | 1.87E+04 | 5.84E-04 | 3.12E-08 | 19.8 | 0.2 | 6.0 | 37.1 |
| | H105/106/108 | 409 | 13.0 | 8.21E+04 | 4.29E-04 | 5.22E-09 | 26.9 | 345 | -4.4 | NB | NB | NB | NB | No binding at Low pH | | |
| | H105/106/111 | 767 | 9.3 | 4.84E+04 | 1.25E-03 | 2.58E-08 | 9.3 | 645 | -6.1 | NB | NB | NB | NB | No binding at Low pH | | |
| | H105/108/111 | 578 | 24.5 | 8.99E+04 | 2.87E-04 | 3.19E-09 | 40.2 | 479 | -0.7 | NB | NB | NB | NB | No binding at Low pH | | |
| | H106/108/111 | 765 | 15.1 | 5.04E+04 | 1.65E-03 | 3.27E-08 | 7.0 | 661 | -5.9 | NB | NB | NB | NB | No binding at Low pH | | |
| | H105/106/108/111 | 723 | 0.3 | NB | NB | NB | NB | 611 | -7.0 | NB | NB | NB | NB | No binding at either pH tested | | |
| | ULC + Heavy | 781 | 39.8 | 1.13E+05 | 1.78E-04 | 1.57E-09 | 64.9 | 665 | 11.7 | 2.04E+04 | 1.22E-03 | 6.00E-08 | 9.4 | 0.2 | 6.9 | 38.2 |
| | Heavy only | 143 | -1.8 | NB | NB | NB | NB | 115 | -6.1 | NB | NB | NB | NB | Negative Control | | |
| | No DNA | 63 | -2.1 | NB | NB | NB | NB | 35 | -6.4 | NB | NB | NB | NB | | | |

FIG. 5B

| Heavy Chain | Light Chain Mutant | Kinetics at pH 7.4 | | | | | | Kinetics at pH 5.75 | | | | | | Ratio of low pH / neutral pH | | |
|---|---|---|---|---|---|---|---|---|---|---|---|---|---|---|---|---|
| | | mAb captured (RU) | 50nM Antigen Bindng (RU) | ka (1/Ms) | kd (1/s) | KD (M) | t½ (min) | mAb captured (RU) | 50nM Antigen Binding (RU) | ka (1/Ms) | kd (1/s) | KD (M) | t½ (min) | ka | kd | KD |
| 3 | H105 | 574 | 12.4 | 5.64E+04 | 1.21E-03 | 2.15E-08 | 9.5 | 496 | 0.1 | NB | NB | NB | NB | No binding at Low pH | | |
| | H106 | 662 | 16.1 | 7.37E+04 | 5.36E-04 | 7.27E-09 | 21.5 | 584 | 3.0 | 3.00E+04 | 4.79E-03 | 1.58E-07 | 2.4 | 0.4 | 8.9 | 21.7 |
| | H108 | 518 | 12.3 | 4.82E+04 | 2.15E-04 | 4.46E-09 | 53.7 | 440 | 2.2 | 3.70E+04 | 1.25E-03 | 3.40E-08 | 9.3 | 0.8 | 5.8 | 7.6 |
| | H111 | 480 | 9.1 | 1.82E+04 | 4.16E-04 | 2.28E-08 | 27.7 | 406 | 0.4 | NB | NB | NB | NB | No binding at Low pH | | |
| | H105/106 | 487 | 7.4 | 1.82E+04 | 7.45E-04 | 4.10E-07 | 1.6 | 423 | -4.1 | NB | NB | NB | NB | Poor binding at Neutral, No binding at Low pH | | |
| | H105/108 | 548 | 11.8 | 3.25E+04 | 5.25E-04 | 1.62E-08 | 22.0 | 468 | 0.0 | NB | NB | NB | NB | No binding at Low pH | | |
| | H105/111 | 504 | 7.9 | 1.06E+04 | 1.66E-03 | 1.57E-07 | 7.0 | 430 | -1.6 | NB | NB | NB | NB | Poor binding at Neutral, No binding at Low pH | | |
| | H106/108 | 487 | 10.7 | 6.64E+04 | 2.91E-04 | 4.38E-09 | 39.7 | 424 | -4.2 | NB | NB | NB | NB | No binding at Low pH | | |
| | H106/111 | 563 | 10.5 | 2.75E+04 | 3.71E-04 | 1.35E-08 | 31.2 | 482 | -1.9 | NB | NB | NB | NB | No binding at Low pH | | |
| | H108/111 | 528 | 10.1 | 1.10E+04 | 8.01E-05 | 7.27E-09 | 144.2 | 449 | -0.5 | NB | NB | NB | NB | No binding at Low pH | | |
| | H105/106/108 | 470 | 6.4 | 2.64E+04 | 5.40E-04 | 2.04E-07 | 2.1 | 412 | -5.3 | NB | NB | NB | NB | Poor binding at Neutral, No binding at Low pH | | |
| | H105/106/111 | 539 | 0.8 | NB | NB | NB | NB | 462 | -5.6 | NB | NB | NB | NB | No binding at either pH tested | | |
| | H105/108/111 | 419 | 6.5 | 1.76E+04 | 1.01E-04 | 2.27E-08 | 28.8 | 354 | -3.8 | NB | NB | NB | NB | No binding at Low pH | | |
| | H106/108/111 | 509 | 3.3 | 5.47E+04 | 9.07E-04 | 1.66E-08 | 12.7 | 443 | -5.9 | NB | NB | NB | NB | Poor binding at Neutral, No binding at Low pH | | |
| | H105/106/108/111 | 450 | -1.1 | NB | NB | NB | NB | 382 | -6.4 | NB | NB | NB | NB | No binding at either pH tested | | |
| | ULC + Heavy | 688 | 16.9 | 3.54E+04 | 3.57E-04 | 1.01E-08 | 32.3 | 598 | 5.0 | 1.16E+04 | 1.76E-03 | 1.52E-07 | 6.6 | 0.3 | 4.9 | 15.0 |
| | Heavy only | 152 | -1.6 | NB | NB | NB | NB | 127 | -5.4 | NB | NB | NB | NB | Negative Control | | |
| | No DNA | 54 | -1.7 | NB | NB | NB | NB | 30 | -5.6 | NB | NB | NB | NB | | | |

FIG. 5C

| Heavy Chain | Light Chain Mutant | Kinetics at pH 7.4 ||||||| Kinetics at pH 5.75 ||||| Ratio of low pH / neutral pH |||
|---|---|---|---|---|---|---|---|---|---|---|---|---|---|---|---|---|
| | | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 4 | H105 | 598 | 4.9 | 2.80E+04 | 1.38E-03 | 4.91E-08 | 8.4 | 512 | -0.2 | NB | NB | NB | NB | Poor binding at Neutral, No binding at Low pH | | |
| | H106 | 569 | 7.1 | 1.49E+04 | 9.67E-04 | 6.49E-08 | 11.9 | 494 | 1.2 | NB | NB | NB | NB | Poor binding at Neutral, No binding at Low pH | | |
| | H108 | 587 | 6.3 | 2.25E+04 | 2.02E-03 | 8.96E-08 | 5.7 | 500 | -0.9 | NB | NB | NB | NB | Poor binding at Neutral, No binding at Low pH | | |
| | H111 | 606 | 5.6 | 3.46E+04 | 2.19E-03 | 6.33E-08 | 5.3 | 521 | -0.9 | NB | NB | NB | NB | Poor binding at Neutral, No binding at Low pH | | |
| | H105/106 | 517 | 3.1 | 2.00E+04 | 2.05E-03 | 1.03E-07 | 5.6 | 460 | -1.1 | NB | NB | NB | NB | Poor binding at Neutral, No binding at Low pH | | |
| | H105/108 | 581 | 2.5 | 1.61E+05 | 2.30E-03 | 1.43E-08 | 5.0 | 506 | -2.7 | NB | NB | NB | NB | Poor binding at Neutral, No binding at Low pH | | |
| | H105/111 | 575 | 3.8 | 1.01E+04 | 1.70E-04 | 1.68E-07 | 6.8 | 504 | -2.0 | NB | NB | NB | NB | Poor binding at Neutral, No binding at Low pH | | |
| | H106/108 | 498 | 2.5 | 4.01E+04 | 6.07E-04 | 1.51E-08 | 19.0 | 447 | -3.9 | NB | NB | NB | NB | Poor binding at Neutral, No binding at Low pH | | |
| | H106/111 | 587 | 3.0 | 7.85E+04 | 9.20E-04 | 1.17E-08 | 12.6 | 509 | -2.6 | NB | NB | NB | NB | Poor binding at Neutral, No binding at Low pH | | |
| | H108/111 | 599 | 4.0 | 9.68E+04 | 2.02E-03 | 2.09E-08 | 5.7 | 528 | -2.6 | NB | NB | NB | NB | Poor binding at Neutral, No binding at Low pH | | |
| | H105/106/108 | 64 | -1.7 | NB | NB | NB | NB | 46 | -5.4 | NB | NB | NB | NB | No binding at either pH tested | | |
| | H105/106/111 | 561 | 1.1 | NB | NB | NB | NB | 493 | -2.8 | NB | NB | NB | NB | No binding at either pH tested | | |
| | H105/108/111 | 521 | 2.7 | 7.66E+04 | 1.29E-03 | 1.68E-08 | 9.0 | 461 | -3.2 | NB | NB | NB | NB | Poor binding at Neutral, No binding at Low pH | | |
| | H106/108/111 | 577 | 1.3 | NB | NB | NB | NB | 514 | -4.2 | NB | NB | NB | NB | No binding at either pH tested | | |
| | H105/106/108/111 | 554 | 0.6 | NB | NB | NB | NB | 495 | -4.8 | NB | NB | NB | NB | No binding at either pH tested | | |
| | ULC + Heavy | 585 | 7.4 | 5.69E+04 | 2.01E-03 | 3.53E-08 | 5.7 | 527 | 1.9 | NB | NB | NB | NB | No binding at Low pH | | |
| | Heavy only | 187 | -2.4 | NB | NB | NB | NB | 161 | -5.4 | NB | NB | NB | NB | | | |
| | No DNA | 49 | -2.6 | NB | NB | NB | NB | 25 | -5.6 | NB | NB | NB | NB | Negative Control | | |

FIG. 5D

| Heavy Chain | Light Chain Mutant | Kinetics at pH 7.4 ||||| Kinetics at pH 5.75 ||||| Ratio of low pH / neutral pH |||
|---|---|---|---|---|---|---|---|---|---|---|---|---|---|---|
| | | mAb captured (RU) | 50nM Antigen Bindng (RU) | ka (1/Ms) | kd (1/s) | KD (M) | t½ (min) | mAb captured (RU) | 50nM Antigen Bindng (RU) | ka (1/Ms) | kd (1/s) | KD (M) | t½ (min) | ka | kd | KD |
| 5 | H105 | 522 | 3.2 | 5.05E+04 | 9.48E-03 | 1.88E-07 | 1.2 | 463 | -4.3 | NB | NB | NB | NB | Poor binding at Neutral, No binding at Low pH |||
| | H106 | 496 | 0.3 | NB | NB | NB | NB | 437 | -5.2 | NB | NB | NB | NB | No binding at either pH tested |||
| | H108 | 475 | -0.1 | NB | NB | NB | NB | 415 | -5.7 | NB | NB | NB | NB | No binding at either pH tested |||
| | H111 | 523 | 1.6 | NB | NB | NB | NB | 463 | -4.7 | NB | NB | NB | NB | No binding at either pH tested |||
| | H105/106 | 534 | -0.6 | NB | NB | NB | NB | 472 | -5.5 | NB | NB | NB | NB | No binding at either pH tested |||
| | H105/108 | 499 | 2.0 | 5.80E+04 | 1.16E-02 | 1.99E-07 | 1.0 | 433 | -5.5 | NB | NB | NB | NB | Poor binding at Neutral, No binding at Low pH |||
| | H105/111 | 489 | 0.1 | NB | NB | NB | NB | 426 | -4.7 | NB | NB | NB | NB | No binding at either pH tested |||
| | H106/108 | 441 | -0.5 | NB | NB | NB | NB | 386 | -4.2 | NB | NB | NB | NB | No binding at either pH tested |||
| | H106/111 | 529 | -0.8 | NB | NB | NB | NB | 461 | -6.3 | NB | NB | NB | NB | No binding at either pH tested |||
| | H108/111 | 495 | 4.1 | 1.73E+05 | 1.06E-02 | 6.11E-08 | 1.1 | 435 | -4.0 | NB | NB | NB | NB | Poor binding at Neutral, No binding at Low pH |||
| | H105/106/108 | 505 | -1.1 | NB | NB | NB | NB | 444 | -5.5 | NB | NB | NB | NB | No binding at either pH tested |||
| | H105/106/111 | 499 | -1.7 | NB | NB | NB | NB | 438 | -5.8 | NB | NB | NB | NB | No binding at either pH tested |||
| | H105/108/111 | 436 | 0.8 | NB | NB | NB | NB | 388 | -3.7 | NB | NB | NB | NB | No binding at either pH tested |||
| | H106/108/111 | 539 | -1.4 | NB | NB | NB | NB | 477 | -4.0 | NB | NB | NB | NB | No binding at either pH tested |||
| | H105/106/108/111 | 556 | -1.6 | NB | NB | NB | NB | 490 | -4.4 | NB | NB | NB | NB | No binding at either pH tested |||
| | ULC + Heavy | 516 | 0.6 | NB | NB | NB | NB | 451 | -5.0 | NB | NB | NB | NB | No binding at either pH tested |||
| | Heavy only | 144 | -1.3 | NB | NB | NB | NB | 122 | -5.7 | NB | NB | NB | NB | No binding at either pH tested |||
| | No DNA | 47 | -1.4 | NB | NB | NB | NB | 25 | -5.8 | NB | NB | NB | NB | Negative Control |||

FIG. 5E

| $V_H$ | $V_K$ | $K_D$ at pH7.4 (nM) | $K_D$ at pH5.75 (nM) | $T_{1/2}$ at pH7.4 (min) | $T_{1/2}$ at pH5.75 (min) |
|---|---|---|---|---|---|
| 2 | Parental ULC | 1.6 | 60 | 65 | 9.4 |
| 2 | ULC (His105,106) | 3.4 | 570 | 39 | 1.8 |
| 2 | ULC (His105,111) | 4.1 | 1270 | 32 | 0.9 |
| 2 | ULC (His105,108,111) | 3.2 | NB | 40 | NB |
| 2 | ULC (His105,106,108) | 5.2 | 152 | 27 | NB |
| 3 | Parental ULC | 10.1 | NB | 32 | 6.6 |
| 3 | ULC (His106,108) | 4.4 | NB | 40 | NB |
| 3 | ULC (His108,111) | 7.3 | NB | 144 | NB |
| 6 | Parental ULC | 3.0 | 2.4 | 10 | 6 |
| 6 | ULC (His105,111) | 3.5 | NB | 9 | NB |
| 6 | ULC (His106,108,111) | 2.0 | NB | 16 | NB |

FIG. 6

Site-directed mutagenesis primers for Histidine substitutions in CDR3 of Universal Light Chain of hVK1-39JK5

| Primer name | Sequence | %GC | N | %mismatch | Tm |
|---|---|---|---|---|---|
| GERMLINE hVK1-39/JK5 | CAACTTACTACTGTCAACAGAGTTACAGTACCCCTCGATCACCTTCGGC | | | | |
| 1633-H106/108/111 F | CTTACTACTGTCAACACATAGTCACAGTACCCATCCGATCACCTTCG | 47.0 | 45 | 6.7 | 79.0 |
| 1633-H105/106/108/111 F | CAACTTACTACTGTCACCATAGTCACAGTACCCATCCGATCACCTTCGGC | 50.0 | 50 | 8.0 | 80.5 |
| 1633-H106/108/111 R | CGAAGGTGATCGGATGGGTACTGTGACTATGTTGACAGTAGTAAG | 47.0 | 45 | 6.7 | 79.0 |
| 1633-H105/106/108/111 R | GCCGAAGGTGATCGGATGGGTACTGTGACTATGGTGACAGTAGTAAGTTG | 50.0 | 50 | 8.0 | 80.5 |

| Primer | SEQ ID NO |
|---|---|
| GERMLINE hVK1-39/JK5 | 81 |
| 1633-H106/108/111 F | 34 |
| 1633-H105/106/108/111 F | 35 |
| 1633-H106/108/111 R | 36 |
| 1633-H105/106/108/111 R | 37 |

FIG. 7

|     |     |     |     |     |     |     |     |
|-----|-----|-----|-----|-----|-----|-----|-----|
| 105 | 106 | 107 | 108 | 109 | 110 | 111 |     |

WT
Q   Q   Y   G   S   S   P   SEQ ID NO:75
CAG CAG TAT GGT AGC TCA CCT  SEQ ID NO:74

H105/106/107/109
H   H   H   G   H   S   P   SEQ ID NO:77
CAT CAC CAT GGT CAC TCA CCT  SEQ ID NO:76

H105/106/109
H   H   Y   G   H   S   P   SEQ ID NO:79
CAT CAC TAT GGT CAC TCA CCT  SEQ ID NO:78

FIG. 12

Site-directed mutagenesis primers for Histidine substitutions in CDR3 of VK3-20JK1 ULC plasmid

| Primer name | Sequence | %GC | N | mismatches | Tm |
|---|---|---|---|---|---|
| GERMLINE hVK3-20 | GATTTTGCAGTGTATTACTGTCAGCAGTATGGTAGCTCACCTTGGACGTTCGGC | | | | |
| hVK3-20 (H105/106/107/109) F | GATTTTGCAGTGTATTACTGTCATCACCATGGTCACTCACCTTGGACGTTCGGC | 48 | 54 | 5 | 79.5 |
| hVK3-20 (H105/106/107/109) R | GCCGAACGTCCAAGGTGAGTGACCATGGTGATGACAGTAATACACTGCAAAATC | 48 | 54 | 5 | 79.5 |
| hVK3-20 (H105/106/109) F | GCAGTGTATTACTGTCATCACTATGGTCACTCACCTTGGACGTTCGG | 49 | 47 | 4 | 78.7 |
| hVK3-20 (H105/106/109) R | CCGAACGTCCAAGGTGAGTGACCATAGTGATGACAGTAATACACTGC | 49 | 47 | 4 | 79.7 |

| Primer | SEQ ID NO |
|---|---|
| GERMLINE hVK3-20/JK1 | 60 |
| hVK3-20 H105/106/107/109 F | 61 |
| hVK3-20 H105/106/107/109 R | 62 |
| hVK3-20 H105/106/109 F | 63 |
| hVK3-20 H105/106/109 R | 64 |

FIG. 13

HISTIDINE ENGINEERED LIGHT CHAIN ANTIBODIES AND GENETICALLY MODIFIED NON-HUMAN ANIMALS FOR GENERATING THE SAME

CROSS-REFERENCE TO RELATED APPLICATIONS

This application claims benefit under 35 U.S.C. §119(e) of U.S. Provisional Application No. 61/611,950, filed Mar. 16, 2012, and U.S. Provisional Application No. 61/736,930, filed Dec. 13, 2012, both incorporated by reference herein in their entireties.

FIELD OF INVENTION

A genetically modified non-human animal (e.g., rodent, e.g., mouse or rat) is provided that expresses antibodies capable of binding to an antigen in a pH dependent manner. A method for making modifications to immunoglobulin light chain variable region sequence of a non-human animal is provided, wherein the modifications include the mutagenesis of residues within the light chain variable region gene, e.g., nucleotides that encode one or more amino acids within a complementary determining region (CDR), to facilitate in vivo expression of antibodies comprising light chain domains that exhibit pH dependent binding to antigens. Methods for making antibodies with pH-dependent antigen binding are also provided.

BACKGROUND OF THE INVENTION

Antibodies typically comprise a homodimeric heavy chain component, wherein each heavy chain monomer is associated with an identical light chain. Antibodies having a heterodimeric heavy chain component (e.g., bispecific antibodies) are desirable as therapeutic antibodies. But making bispecific antibodies having a suitable light chain component that can satisfactorily associate with each of the heavy chains of a bispecific antibody has proved problematic.

In one approach, a light chain might be selected by surveying usage statistics for all light chain variable domains, identifying the most frequently employed light chain in human antibodies, and pairing that light chain in vitro with the two heavy chains of differing specificity.

In another approach, a light chain might be selected by observing light chain sequences in a phage display library (e.g., a phage display library comprising human light chain variable region sequences, e.g., a human scFv library) and selecting the most commonly used light chain variable region from the library. The light chain can then be tested on the two different heavy chains of interest.

In another approach, a light chain might be selected by assaying a phage display library of light chain variable sequences using the heavy chain variable sequences of both heavy chains of interest as probes. A light chain that associates with both heavy chain variable sequences might be selected as a light chain for the heavy chains.

In another approach, a candidate light chain might be aligned with the heavy chains' cognate light chains, and modifications are made in the light chain to more closely match sequence characteristics common to the cognate light chains of both heavy chains. If the chances of immunogenicity need to be minimized, the modifications preferably result in sequences that are present in known human light chain sequences, such that proteolytic processing is unlikely to generate a T cell epitope based on parameters and methods known in the art for assessing the likelihood of immunogenicity (i.e., in silico as well as wet assays).

All of the above approaches rely on in vitro methods that subsume a number of a priori restraints, e.g., sequence identity, ability to associate with specific pre-selected heavy chains, etc. There is a need in the art for compositions and methods that do not rely on manipulating in vitro conditions, but that instead employ more biologically sensible approaches to making human epitope-binding proteins that include a common light chain.

In addition, therapeutic antibodies, e.g., bispecific therapeutic antibodies, have some limitations in that they often require high doses to achieve desired efficacy. This is partly due to the fact that antibody-antigen complexes are internalized into the endosome, and are targeted for lysosomal degradation in a process called target-mediated clearance. Thus, there is a need in the art for methods and compositions that lead to more efficient antibody recycling, e.g., bispecific antibody recycling, and prevent degradation of the antibody by promoting dissociation of antibody-antigen complexes in the endosomal compartment without compromising the specificity and affinity of the antibody toward the antigen.

SUMMARY OF THE INVENTION

In one aspect, a biological system is provided for generating an antibody or an antibody variable domain that binds a target antigen at a neutral pH but exhibits reduced binding of the same antigen at an acidic pH (e.g., pH 5.0-6.0). The biological system comprises a non-human animal, e.g., a rodent (e.g, a mouse or rat) that has a rearranged light chain sequence (e.g., a rearranged V-J) that comprises one or more histidine modifications. In various aspects, the one or more histidine modifications are in the light chain CDR3 codon. In various aspects, the non-human animal comprises a human or humanized heavy chain immunoglobulin locus. In various aspects, the non-human animal comprises a replacement of endogenous non-human heavy chain variable gene segments with one or more human heavy chain $V_H$, $D_H$, and $J_H$ segments, wherein the human segments are operably linked to a non-human immunoglobulin constant region. In various aspects, non-human animals with universal light chains comprising light chain variable domains with substitutions of non-histidine residues for histidine residues are provided. In various aspects these histidine-modified universal light chain non-human animals (e.g., rodents, e.g., mice) are referred to as histidine-universal light chain mice, histidine-ULC mice, or HULC mice.

Thus, in one aspect, provided herein is a genetically modified non-human animal that comprises in its germline an immunoglobulin light chain locus that comprises a single rearranged human immunoglobulin light chain variable region gene sequence comprising human $V_L$ and $J_L$ segment sequences, wherein the single rearranged human immunoglobulin light chain variable region sequence comprises a substitution of at least one non-histidine codon with a histidine codon. In one embodiment, the single rearranged human immunoglobulin variable region sequence is operably linked to an immunoglobulin light chain constant region gene sequence. In one embodiment, the immunoglobulin light chain constant region gene sequence is a non-human immunoglobulin light chain constant region gene sequence. In one embodiment, the non-human immunoglobulin light chain constant region gene sequence is an endogenous immunoglobulin light chain constant region gene sequence. In one embodiment, the non-human animal lacks a functional unrearranged immunoglobulin light chain variable region. In one embodiment, the immunoglobulin light chain locus is at an endogenous non-human immunoglobulin light chain locus.

In one embodiment, the animal further comprises in its germline an immunoglobulin heavy chain locus that comprises an unrearranged immunoglobulin heavy chain variable region gene sequence comprising human $V_H$, $D_H$, and $J_H$ segments operably linked to an immunoglobulin heavy chain constant region gene sequence. In one embodiment, the immunoglobulin heavy chain constant region gene sequence is a non-human heavy chain constant region gene sequence. In one embodiment, the non-human heavy chain constant region gene sequence is an endogenous immunoglobulin heavy chain constant region gene sequence. In one embodiment, the immunoglobulin heavy chain locus is at an endogenous immunoglobulin heavy chain locus.

In one embodiment, the substitution of at least one non-histidine codon with a histidine codon is in the nucleotide sequence encoding a complementary determining region (CDR). In one embodiment, the substitution of at least one non-histidine codon with a histidine codon is in the nucleotide sequence encoding a CDR3. In one embodiment, the substitution is of one, two, three, four, or more CDR3 codons. In one aspect, the single rearranged human immunoglobulin light chain variable region sequence comprised at the immunoglobulin light chain locus is derived from a human Vκ1-39 or Vκ3-20 gene segment. In one embodiment, the single rearranged human immunoglobulin light chain variable region is derived from a rearranged Vκ1-39/Jκ5 or Vκ3-20/Jκ1 gene sequence. In one embodiment, the single rearranged human immunoglobulin light chain variable region is derived from a rearranged Vκ1-39/Jκ5 gene sequence, and the Vκ1-39/Jκ5 gene sequence comprises a replacement of at least one non-histidine codon with a histidine codon designed to express a histidine at a position selected from 105, 106, 108, 111, and a combination thereof. In another embodiment, the single rearranged human immunoglobulin light chain variable region is derived from a rearranged Vκ3-20/Jκ1 gene sequence, and the Vκ3-20/Jκ1 gene sequence comprises a replacement of at least one non-histidine codon with a histidine codon designed to express a histidine at a position selected from 105, 106, 107, 109, and a combination thereof.

In one aspect, the non-human animal described herein comprises a population of B cells in response to an antigen of interest that is enriched for antibodies that exhibit a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, the decrease in $t_{1/2}$ at an acidic pH as compared to a neutral pH is about 30 fold or more.

In one embodiment, the animal expresses an antibody comprising a human immunoglobulin light chain variable domain with a substitution of at least one non-histidine residue with a histidine residue at an amino acid position encoded by the at least one codon substituted in the immunoglobulin light chain variable region gene sequence. In one embodiment, the animal expresses an antibody that retains a substitution of at least one non-histidine residue with a histidine residue in an expressed human immunoglobulin light chain variable domain, despite somatic hypermutations.

In one embodiment, the non-human animal is a mammal. In one embodiment, the mammal is a rodent, e.g., a rat or a mouse. In one embodiment, the non-human animal is a mouse. Thus, in one aspect, also provided herein is a genetically modified mouse comprising in its germline an immunoglobulin light chain locus that comprises a single rearranged human immunoglobulin light chain variable region gene sequence comprising human $V_L$ and $J_L$ segment sequences, wherein the single rearranged human immunoglobulin light chain variable region sequence comprises a substitution of at least one non-histidine codon with a histidine codon. In one embodiment, the mouse lacks a functional unrearranged immunoglobulin light chain variable region.

In one embodiment, the single rearranged immunoglobulin light chain variable region gene sequence in the germline of the mouse is operably linked to an immunoglobulin light chain constant region gene sequence. In one embodiment, the immunoglobulin light chain constant region gene sequence is selected from a rat or a mouse immunoglobulin light chain constant region gene sequence. In one embodiment, the immunoglobulin light chain constant region gene sequence is a mouse sequence. In one embodiment, the immunoglobulin light chain locus is at an endogenous mouse immunoglobulin light chain locus.

In a further embodiment, the mouse also comprises in its germline an immunoglobulin heavy chain locus that comprises an unrearranged immunoglobulin heavy chain variable region sequence comprising human $V_H$, $D_H$, and $J_H$ segments operably linked to an immunoglobulin heavy chain constant region gene sequence. In one aspect, the immunoglobulin heavy chain constant region gene sequence is a rat or a mouse heavy chain constant region gene sequence. In one embodiment, the immunoglobulin heavy chain constant region gene sequence is a mouse sequence. In one embodiment, the immunoglobulin heavy chain locus is at an endogenous mouse immunoglobulin heavy chain locus.

In one aspect, the mouse comprises a substitution of at least one non-histidine codon with a histidine codon wherein the substitution is in the nucleotide sequence encoding a CDR. In one embodiment, the substitution is in a CDR3 codon, e.g., in one, two, three, four, or more CDR3 codons. In one embodiment, the immunoglobulin light chain locus of the mouse comprises the single rearranged human immunoglobulin light chain variable region sequence derived from a human Vκ1-39 or Vκ3-20 gene segment, e.g., the single rearranged immunoglobulin light chain variable region sequence is derived from a rearranged Vκ1-39/Jκ5 or Vκ3-20/Jκ1 gene sequence. In one embodiment, the single rearranged immunoglobulin light chain variable region sequence is derived from a rearranged Vκ1-39/Jκ5 gene sequence and the Vκ1-39/Jκ5 sequence comprises a replacement of at least one non-histidine codon with a histidine codon designed to express a histidine at a position selected from 105, 106, 108, 111, and a combination thereof. In one embodiment, such replacement is designed to replace histidines at positions 105, 106, 108, and 111. In another embodiment, such replacement is designed to replace histidines at positions 106, 108, and 111.

In another embodiment, the single rearranged immunoglobulin light chain variable region sequence is derived from a rearranged Vκ3-20/Jκ1 gene sequence and the Vκ3-20/Jκ1 sequence comprises a replacement of at least one non-histidine codon with a histidine codon designed to express a histidine at a position selected from 105, 106, 107, 109, and a combination thereof. In one embodiment, such replacement is designed to replace histidines at positions 105, 106, 107, and 109. In another embodiment, such replacement is designed to replace histidines at positions 105, 106, and 109.

In one embodiment, the mouse described herein comprises a population of B cells in response to an antigen of interest that is enriched for antibodies that exhibit a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, the decrease in $t_{1/2}$ at an acidic pH as compared to a neutral pH is about 30 fold or more.

In one embodiment, the mouse described herein expresses a population of antigen-specific antibodies in response to an antigen of interest wherein all antibodies comprise (a) immunoglobulin light chain variable domains derived from the same single rearranged human light chain variable region gene sequence which comprises a substitution of at least one non-histidine codon with a histidine codon, and (b) immunoglobulin heavy chains comprising heavy chain variable domains derived from a repertoire of human heavy chain V, D, and J segments.

Also provided herein is a non-human locus, e.g., mouse locus, comprising a single rearranged human immunoglobulin light chain variable region gene sequence comprising human $V_L$ and $J_L$ segment sequences, wherein the single rearranged human immunoglobulin light chain variable region gene sequence comprises a substitution of at least one non-histidine codon with a histidine codon. In one embodiment, the locus is comprised in the germline of a non-human animal. In one embodiment, the locus comprises the single rearranged human immunoglobulin light chain variable region gene sequence derived from a human Vκ1-39 or Vκ3-20 gene segment, e.g., derived from a rearranged Vκ1-39/Jκ5 or Vκ3-20/Jκ1 gene sequence. In one embodiment, wherein the single rearranged human immunoglobulin light chain variable region gene sequence present in the locus is derived from the rearranged Vκ1-39/Jκ5 sequence, the substitution of at least one non-histidine codon with a histidine codon is designed to express a histidine at a position selected from 105, 106, 108, 111, and a combination thereof. In another embodiment, wherein the single rearranged human immunoglobulin light chain variable region gene sequence present in the locus is derived from the rearranged Vκ3-20/Jκ1 sequence, the substitution of at least one non-histidine codon with a histidine codon is designed to express a histidine at a position selected from 105, 106, 107, 109, and a combination thereof. In various embodiments, the non-human loci described herein may be generated using methods described below for making a genetically modified non-human animal.

In yet another aspect, provided herein is a method for making a non-human animal that comprises a genetically modified immunoglobulin light chain locus in its germline, wherein the method comprises modifying a genome of a non-human animal to delete or render nonfunctional endogenous immunoglobulin light chain V and J segments in an immunoglobulin light chain locus, and placing in the genome a single rearranged human light chain variable region gene sequence comprising a substitution of at least one non-histidine codon with a histidine codon. In one embodiment, such method results in a genetically modified non-human animal that comprises a population of B cells enriched for antibodies exhibiting pH-dependent binding to the antigen of interest. In one embodiment, the single rearranged human immunoglobulin light chain variable region sequence placed in the genome is derived from a human Vκ1-39 or Vκ3-20, e.g., a rearranged Vκ1-39/Jκ5 or Vκ3-20/Jκ1 gene sequence. Thus, in the embodiment wherein the single rearranged human immunoglobulin light chain variable region sequence is derived from a rearranged Vκ1-39/Jκ5, the substitution of at least one non-histidine codon with a histidine codon is designed to express a histidine at a position selected from 105, 106, 108, 111, and a combination thereof. In an embodiment wherein the single rearranged human immunoglobulin light chain variable region sequence is derived from a rearranged Vκ3-20/Jκ1, the substitution of at least one non-histidine codon with a histidine codon is designed to express a histidine at a position selected from 105, 106, 107, 109, and a combination thereof.

In another aspect, provided herein is a method of generating an antibody that exhibits pH-dependent binding to an antigen of interest comprising (a) generating a mouse described herein (e.g., a mouse that comprises in its germline an immunoglobulin light chain locus that comprises a single rearranged human immunoglobulin light chain variable region sequence comprising human $V_L$ and $J_L$ segment sequences and a substitution of at least one non-histidine codon with a histidine codon in its rearranged light chain variable region sequence), (b) immunizing the mouse with an antigen of interest, and (c) selecting an antibody that binds to the antigen of interest with a desired affinity at a neutral pH while displaying reduced binding to the antigen at an acidic pH. In one embodiment, the method results in a generation of an antibody that exhibits $t_{1/2}$ at acidic pH and 37° C. of about 2 minutes or less. In one embodiment, the method results in a generation of an antibody that displays a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold.

In other aspects, provided herein are additional methods of generating an antibody that exhibits pH-dependent binding to an antigen of interest. One such method comprises (a) selecting a first antibody that binds to an antigen of interest with a desired affinity, (b) modifying an immunoglobulin light chain nucleotide sequence of the first antibody to comprise a substitution of at least one non-histidine codon with a histidine codon, (c) expressing an immunoglobulin heavy chain of the first antibody and the modified immunoglobulin light chain in a cell, and (d) selecting a second antibody expressed in the cell that retains a desired affinity for the antigen of interest at neutral pH and displays reduced binding to the antigen of interest at an acidic pH. In one embodiment, the immunoglobulin light chain nucleotide sequence of the first antibody comprises a single rearranged human immunoglobulin light chain variable region sequence. In one embodiment, the first antibody is generated in a non-human animal, e.g., a mouse, comprising an immunoglobulin light chain sequence derived from a single rearranged human immunoglobulin light chain variable region sequence, and the modification of the immunoglobulin light chain is made in the single rearranged human immunoglobulin variable region sequence. In one embodiment, the first antibody is generated in a non-human animal, e.g., a mouse, further comprising an immunoglobulin heavy chain sequence derived from a repertoire of human $V_H$, $D_H$, and $J_H$ segments. In one embodiment, the single rearranged human immunoglobulin light chain variable region sequence is selected from Vκ1-39/Jκ5 and Vκ3-20/Jκ1 gene sequence. In an embodiment, wherein the single rearranged human immunoglobulin light chain variable region sequence is Vκ1-39/Jκ5, the modification in the immunoglobulin light chain nucleotide sequence of the first antibody is made in the CDR3 codon at a position selected from 105, 106, 108, 111, and a combination thereof. In an embodiment wherein the single rearranged human immunoglobulin light chain variable region sequence is Vκ3-20/Jκ1, the modification in the immunoglobulin light chain nucleotide sequence of the first antibody is made in the CDR3 codon at a position selected from 105, 106, 107, 109, and a combination thereof.

In one embodiment, the method of generating an antibody that exhibits pH-dependent binding to an antigen of interest described herein results in an antibody that displays a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, the method of generating the antibody results in an antibody that exhibits a $t_{1/2}$ at acidic pH and 37° C. of about 2 minutes or less.

Any of the embodiments and aspects described herein can be used in conjunction with one another, unless otherwise indicated or apparent from the context. Other embodiments will become apparent to those skilled in the art from a review of the ensuing description.

BRIEF DESCRIPTION OF THE DRAWINGS

FIG. 1 illustrates an amino acid alignment of human Vκ1-39-derived light chains from various antigen-specific antibodies (A-K antibodies, corresponding to SEQ ID NOs: 82-92, respectively). Histidine (H) residues located within each light chain sequence are in bold. Various light chain regions (Framework and CDR) are indicated above the alignment.

FIG. 2 illustrates the combinations and locations of histidine residues engineered in the CDR3 region of human Vκ1-39-derived light chains by mutagenesis. Corresponding nucleic acid sequences are included. Histidine residues introduced through mutagenesis and corresponding nucleic acid residues are shown in bold. Amino acid positions (105, 106, etc.) are based on a unique numbering described in Lefranc et al. (2003) Dev. Comp. Immunol. 27:55-77, and can also be viewed on the website of the International Immunogenetics Information System (IMGT).

FIGS. 5A-5E show the binding kinetics for selected heavy chains (1-5) from antigen-specific antibodies paired with various histidine engineered light chains at a neutral (7.4) and acidic (5.75) pH. Various kinetic parameters including $k_a$, $k_d$, $K_D$, and $t_{1/2}$ are shown. NB=no binding.

FIG. 6 shows kinetic parameters ($K_D$ and $t_{1/2}$) for antibodies comprising parental universal light chain or histidine-modified universal light chain paired with indicated heavy chains (2, 3, and 6). Histidine substitutions lead to strong pH dependence in several antibodies. Histidine substitutions were made in CDR3 to convert the sequence $_{105}$QQSYSTP$_{111}$ (SEQ ID NO:3) to $_{105}$HHSYSTH$_{111}$ (SEQ ID NO:5). Note that NB=no binding detected (KD>10 micromolar).

FIG. 7 shows the sequence and properties (% GC content, N, % mismatch, Tm) of selected mutagenesis primers used to engineer histidine residues into CDR3 of a rearranged human Vκ1-39/Jκ5 light chain sequence. SEQ ID NOs for these primers used in the Sequence Listing are included in the Table below. F=forward primer, R=reverse primer.

FIGS. 8C-8D show introduction of the targeting vector for ULC-H, 105/106/108/111 substitutions into ES cells and generation of heterozygous mice from the same; while

FIG. 12 shows positions of histidine residues engineered in the CDR3 region of human Vκ3-20-derived light chains by mutagenesis. Histidine residues introduced through mutagenesis and corresponding nucleic acid residues are shown in bold. Amino acid positions (105, 106, etc.) are based on a unique numbering described in Lefranc et al. (2003) Dev. Comp. Immunol. 27:55-77, and can also be viewed on the website of the International Immunogenetics Information System (IMGT).

FIG. 13 shows the sequence and properties (% GC content, N, % mismatch, Tm) of selected mutagenesis primers used to engineer histidine residues into CDR3 of a rearranged human Vκ3-20/Jκ1 light chain sequence. SEQ ID NOs for these primers used in the Sequence Listing are included in the Table below. F=forward primer, R=reverse primer.

FIG. 14C shows introduction of the targeting vector for ULC-Q105H/Q106H/Y107H/S109H substitutions into ES cells and generation of heterozygous mice from the same; while

DETAILED DESCRIPTION OF INVENTION

Definitions

Figure 3:
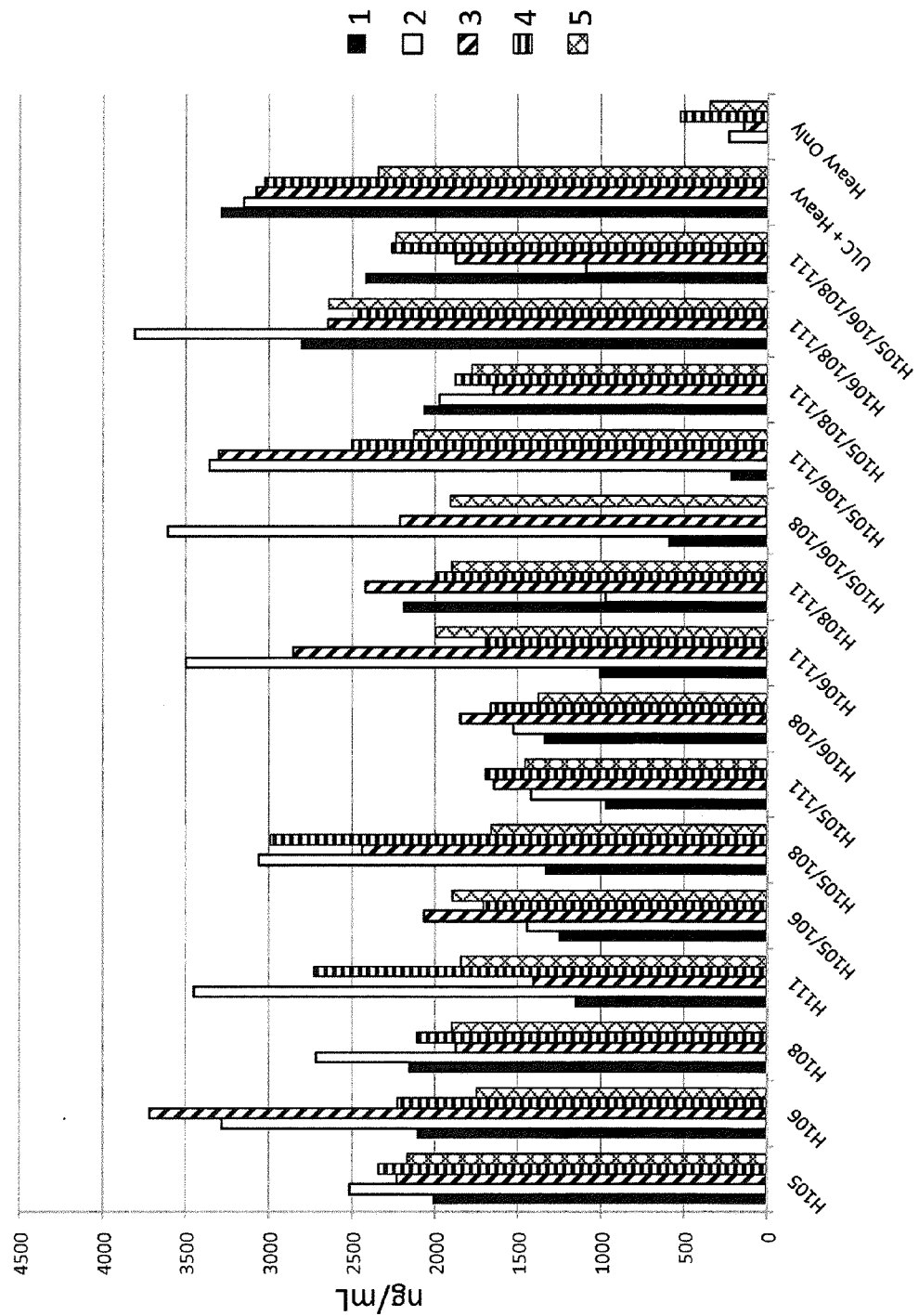
FIG. 3 illustrates the level of antibody expression in ng/mL detected in the supernatants of CHO cells transfected with nucleic acids encoding five (1-5) different heavy chains and Vκ1-39-derived light chains having histidine residues engineered at indicated locations (see Y axis) in the CDR3.

The present invention provides genetically modified non-human animals (e.g., mice, rats, rabbits, hamsters, etc.) that comprise in their genome, e.g., in their germline, nucleotide sequence(s) encoding human antibody molecules that exhibit pH-dependent antigen binding, e.g., a nucleotide sequence of immunoglobulin light chain comprising rearranged human immunoglobulin light chain variable region sequence encoding antibodies that exhibits pH-dependent antigen binding; embryos, cells, and tissues comprising the same; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "antibody", as used herein, includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains, $C_H1$, $C_H2$ and $C_H3$. Each light chain comprises a light chain variable domain and a light chain constant region ($C_L$). The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-9}$ M or lower (e.g., about $1\times10^{-9}$ M, $1\times10^{-10}$ M, $1\times10^{-11}$ M, or about $1\times10^{-12}$ M). In one embodiment, $K_D$ is measured by surface plasmon resonance, e.g., BIACORE™; in another embodiment, $K_D$ is measured by ELISA.

The phrase "bispecific antibody" includes an antibody capable of selectively binding two or more epitopes. Bispecific antibodies generally comprise two nonidentical heavy chains, with each heavy chain specifically binding a different epitope—either on two different molecules (e.g., different epitopes on two different immunogens) or on the same molecule (e.g., different epitopes on the same immunogen). If a bispecific antibody is capable of selectively binding two different epitopes (a first epitope and a second epitope), the affinity of the first heavy chain for the first epitope will generally be at least one to two or three or four or more orders of magnitude lower than the affinity of the first heavy chain for the second epitope, and vice versa. Epitopes specifically bound by the bispecific antibody can be on the same or a different target (e.g., on the same or a different protein). Exemplary bispecific antibodies include those with a first heavy chain specific for a tumor antigen and a second heavy chain specific for a cytotoxic marker, e.g., an Fc receptor (e.g., FcγRI, FcγRII, FcγRIII, etc.) or a T cell marker (e.g., CD3, CD28, etc.). Further, the second heavy chain variable domain can be substituted with a heavy chain variable domain having a different desired specificity. For example, a bispecific antibody with a first heavy chain specific for a tumor antigen and a second heavy chain specific for a toxin can be paired so as to deliver a toxin (e.g., saporin, vinca alkaloid, etc.) to a tumor cell. Other exemplary bispecific antibodies include those with a first heavy chain specific for an activating receptor (e.g., B cell receptor, FcγRI, FcγRIIA, FcγRIIIA, FcαRI, T cell receptor, etc.) and a second heavy chain specific for an inhibitory receptor (e.g., FcγRIIB, CD5, CD22, CD72, CD300a, etc.). Such bispecific antibodies can be constructed for therapeutic conditions associated with cell activation (e.g. allergy and asthma). Bispecific antibodies can be made, for example, by combining heavy chains that recognize different epitopes of the same immunogen. For example, nucleic acid sequences encoding heavy chain variable sequences that recognize different epitopes of the same immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding of one or both of the heavy chains to one or both epitopes.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The phrase "epitope-binding protein" includes a protein having at least one CDR and that is capable of selectively recognizing an epitope, e.g., is capable of binding an epitope with a $K_D$ that is at about one micromolar or lower (e.g., a $K_D$ that is about $1 \times 10^{-6}$ M, $1 \times 10^{-7}$ M, $1 \times 10^{-9}$ M, $1 \times 10^{-9}$ M, $1 \times 10^{-10}$ M, $1 \times 10^{-11}$ M, or about $1 \times 10^{-12}$ M). Therapeutic epitope-binding proteins (e.g., therapeutic antibodies) frequently require a $K_D$ that is in the nanomolar or the picomolar range.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "germline" in reference to an immunoglobulin nucleic acid sequence includes a nucleic acid sequence that can be passed to progeny.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an epitope (e.g., recognizing the epitope with a KD in the micromolar, nanomolar, or picomolar range), that is capable of expressing and secreting from a cell, and that comprises at least one CDR. A heavy chain variable domain is encoded by a variable region gene sequence, which generally comprises VH, DH, and JH segments derived from a repertoire of VH, DH, and JH segments present in the germline. Sequences, locations and nomenclature for V, D, and J heavy chain segments for various organisms can be found in IMGT database, on the website of the International Immunogenetics Information System.

The term "identity" when used in connection with sequence, includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). The length of the sequences compared with respect to identity of sequences will depend upon the particular sequences, but in the case of a light chain constant domain, the length should contain sequence of sufficient length to fold into a light chain constant domain that is capable of self-association to form a canonical light chain constant domain, e.g., capable of forming two beta sheets comprising beta strands and capable of interacting with at least one $C_H1$ domain of a human or a mouse. In the case of a $C_H1$ domain, the length of sequence should contain sequence of sufficient length to fold into a $C_H1$ domain that is capable of forming two beta sheets comprising beta strands and capable of interacting with at least one light chain constant domain of a mouse or a human.

The phrase "immunoglobulin molecule" includes two immunoglobulin heavy chains and two immunoglobulin light chains. The heavy chains may be identical or different, and the light chains may be identical or different.

The phrase "light chain" includes an immunoglobulin light chain sequence from any organism, and unless otherwise specified includes human kappa and lambda light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region. A light chain variable domain is encoded by a light chain variable region gene sequence, which generally comprises $V_L$ and $J_L$ segments, derived from a repertoire of V and J segments present in the germline. Sequences, locations and nomenclature for V and J light chain segments for various organisms can be found in IMGT database, www.imgt.org. Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear. Common or universal light chains include those derived from a human Vκ1-39Jκ5 gene or a human Vκ3-

20Jκ1 gene, and include somatically mutated (e.g., affinity matured) versions of the same.

The phrase "micromolar range" is intended to mean 1-999 micromolar; the phrase "nanomolar range" is intended to mean 1-999 nanomolar; the phrase "picomolar range" is intended to mean 1-999 picomolar.

The phrase "somatically mutated" includes reference to a nucleic acid sequence from a B cell that has undergone class-switching, wherein the nucleic acid sequence of an immunoglobulin variable region (e.g., nucleotide sequence encoding a heavy chain variable domain or including a heavy chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" includes reference to nucleic acid sequences from affinity-matured B cells that are not identical to corresponding immunoglobulin variable region sequences in B cells that are not affinity-matured (i.e., sequences in the genome of germline cells). The phrase "somatically mutated" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The phrase "somatically mutated" refers to sequences from antibodies that have been generated in an animal, e.g., a mouse having human immunoglobulin variable region nucleic acid sequences, in response to an immunogen challenge, and that result from the selection processes inherently operative in such an animal.

The term "unrearranged," with reference to a nucleic acid sequence, includes nucleic acid sequences that exist in the germline of an animal cell.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

The term "operably linked" refers to a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The term "replacement" in reference to gene replacement refers to placing exogenous genetic material at an endogenous genetic locus, thereby replacing all or a portion of the endogenous gene with an orthologous or homologous nucleic acid sequence.

"Functional" as used herein, e.g., in reference to a functional polypeptide, includes a polypeptide that retains at least one biological activity normally associated with the native protein. In another instance, a functional immunoglobulin gene segment may include a variable gene segment that is capable of productive rearrangement to generate a rearranged immunoglobulin gene sequence.

"Neutral pH" includes pH between about 7.0 and about 8.0, e.g., pH between about 7.0 and about 7.4, e.g., between about 7.2 and about 7.4, e.g., physiological pH. "Acidic pH" includes pH of 6.0 or lower, e.g., pH between about 5.0 and about 6.0, pH between about 5.75 and about 6.0, e.g., pH of endosomal or lysosomal compartments.

Engineered Histidine Residues in Immunoglobulin Light Chain Genes

The inventors have discovered that non-human animals that express antibodies that are capable of binding to an antigen in a pH dependent manner can be made by making modifications of an immunoglobulin light chain variable region at one or more positions along the sequence of the light chain. Methods of making modifications in the germline of a non-human animal so that the animal would express histidines in CDRs of antibodies are described. In particular, methods for making modifications in an immunoglobulin light chain variable sequence in the germline of the mouse are described. Variable region sequence, e.g., of light chains, typically show somatic hypermutation along the variable region sequence, and, in some cases, such mutations can result in a substitution of histidine residues (see, e.g., FIG. 1). Such mutations can even occur in complementary determining regions (CDRs), which are the regions of variable domains responsible for antigen binding. In some cases, such mutations can result in antibodies that display pH-dependent antigen binding, e.g., reduced antigen binding at an acidic pH as compared to antigen binding at a neutral pH. Such pH-dependent antigen binding is desired because it may enable the antibody to bind to the antigen outside the cell, and, when internalized into an endosome, release the antigen and recycle back to the surface to bind another antigen, avoiding target-mediated clearance. Approaches for introducing histidine residues to achieve this effect by using a random his-scanning mutagenesis to engineer pH-dependent binding properties in anti-IL-6R antibodies have been reported (US 2011/0111406 A1). However, random mutagenesis of antibody residues may result in decreased affinity of antibody to the antigen. A non-human animal genetically modified to express a histidine substitution in antibody sequence enables generation of high-affinity antibodies in response to an antigen of interest that, due to histidine modification(s), would also display pH-dependent antigen binding.

Thus, in various embodiments, provided herein is a genetically modified non-human animal (e.g., rodent, e.g., a mouse or a rat) that comprises in its genome, e.g., in its germline, a human immunoglobulin light chain variable region sequence comprising modifications that result in the animal expressing antibodies capable of binding to antigens in a pH-dependent manner. In one embodiment, the non-human animal comprises modifications in the human immunoglobulin light chain variable region sequence (e.g., $V_L$ and/or $J_L$ segment sequence) that comprise substitutions in at least one non-histidine codon with a histidine codon (in some cases, also may be referred to as "histidine substitution," "histidine codon substitution," or the like). In one embodiment, the animal comprises at least one substitution of a non-histidine codon with a histidine codon in a nucleotide sequence of a complementary determining region (CDR; e.g., CDR1, CDR2, and/or CDR3) of a human immunoglobulin light chain. In one embodiment, the substitution is in a CDR3 codon. In one embodiment, the light chain is a κ light chain. In one embodiment, the animal expresses an immunoglobulin light chain, e.g., a light chain CDR, e.g., a light chain CDR3, comprising a substitution of at least one amino acid with a histidine. In another embodiment, the light chain is a λ light chain. In yet another embodiment, the mouse comprises a substitution of at least one non-histidine codon with a histidine codon in both κ and λ light chains.

Histidine residue is encoded by two different codons, CAT and CAC (deoxyribonucleic acid residues). Thus, a non-histidine codon may be substituted with a CAT or a CAC. The substitution is engineered in a codon that in its germline configuration (i.e., non-somatically mutated state) does not encode a histidine residue.

In one embodiment a light chain is a universal light chain (also termed a common light chain). As described in U.S. patent application Ser. Nos. 13/022,759, 13/093,156, 13/412, 936 and 13/488,628 (U.S. Application Publication Nos. 2011/0195454, 2012/0021409, 2012/0192300 and 2013/0045492, all incorporated herein by reference), a non-human animal (e.g., a mouse) that selects a common light chain for a plurality of heavy chains has a practical utility. In various embodiments, antibodies expressed in a non-human animal comprising only a common light chain will have heavy chains that can associate and express with an identical or substantially identical light chain. This is particularly useful in making bispecific antibodies. For example, such an animal can be immunized with a first immunogen to generate a B cell that expresses an antibody that specifically binds a first epitope. The animal (or an animal genetically the same) can be immunized with a second immunogen to generate a B cell that expresses an antibody that specifically binds the second epitope. Variable heavy chain regions can be cloned from the B cells and expressed with the same heavy chain constant region and the same light chain (e.g., a common light chain) in a cell to make a bispecific antibody, wherein the heavy chain component of the bispecific antibody has been selected by an animal to associate and express with the same light chain component. In various embodiments described, the variable regions of the genetically engineered mice are human variable regions.

Thus, a mouse was engineered that is capable of generating immunoglobulin light chains that will suitably pair with a rather diverse family of heavy chains, including heavy chains whose human variable regions depart from germline sequences, e.g., affinity matured or somatically mutated variable regions. In various embodiments, the mouse is devised to pair human light chain variable domains with human heavy chain variable domains that comprise somatic mutations, thus enabling a route to high affinity binding proteins suitable for use as human therapeutics.

The genetically engineered mouse, through the long and complex process of antibody selection within an organism, makes biologically appropriate choices in pairing a diverse collection of human heavy chain variable domains with a limited number of human light chain options. In order to achieve this, the mouse is engineered to present a limited number of human light chain variable domain options in conjunction with a wide diversity of human heavy chain variable domain options. Upon challenge with an immunogen, the mouse maximizes the number of solutions in its repertoire to develop an antibody to the immunogen, limited largely or solely by the number or light chain options in its repertoire. In various embodiments, this includes allowing the mouse to achieve suitable and compatible somatic mutations of the light chain variable domain that will nonetheless be compatible with a relatively large variety of human heavy chain variable domains, including in particular somatically mutated human heavy chain variable domains.

The engineered common light chain mouse described in U.S. Application Publication Nos. 2011/0195454, 2012/0021409, 2012/0192300 and 2013/0045492 comprised nucleic acid sequence encoding a limited repertoire of light chain options, e.g., common or universal light chain "ULC" that comprised no more than two $V_L$ segments or a single rearranged human immunoglobulin light chain variable region sequence. To achieve such limited repertoire, a mouse was engineered to render nonfunctional or substantially nonfunctional its ability to make, or rearrange, a native mouse light chain variable domain. In one aspect, this was achieved, e.g., by deleting the mouse's light chain variable region gene segments. As previously described, the endogenous mouse locus can then be modified by exogenous suitable human light chain variable region gene segments of choice, operably linked to the endogenous mouse light chain constant domain, in a manner such that the exogenous human variable region gene segments can combine with the endogenous mouse light chain constant region gene and form a rearranged reverse chimeric light chain gene (human variable, mouse constant). In various embodiments, the light chain variable region is capable of being somatically mutated. In various embodiments, to maximize ability of the light chain variable region to acquire somatic mutations, the appropriate enhancer(s) is retained in the mouse. In one aspect, in modifying a mouse κ light chain locus to replace endogenous mouse κ light chain gene segments with human κ light chain gene segments, the mouse κ intronic enhancer and mouse κ3' enhancer are functionally maintained, or undisrupted.

Thus, provided was a genetically engineered mouse that expresses a limited repertoire of reverse chimeric (human variable, mouse constant) light chains associated with a diversity of reverse chimeric (human variable, mouse constant) heavy chains. In various embodiments, the endogenous mouse κ light chain gene segments are deleted and replaced with a single (or two) rearranged human light chain region, operably linked to the endogenous mouse Cκ gene. In embodiments for maximizing somatic hypermutation of the rearranged human light chain region, the mouse κ intronic enhancer and the mouse κ3' enhancer are maintained. In various embodiments, the mouse also comprises a nonfunctional λ light chain locus, or a deletion thereof or a deletion that renders the locus unable to make a λ light chain.

The universal light chain mouse generated antibodies in response to various antigens that were capable of utilizing a diverse repertoire of heavy chain variable region sequences, comprising a diverse repertoire of $V_H$, $D_H$, and $J_H$ segments. Antibodies generated in such genetically engineered ULC mouse are useful for designing bispecific therapeutic antibodies; however, as with any other antibody, each bispecific antibody may only bind to one target during its lifetime in the plasma; the antibody is internalized into an endosome and targeted for lysosomal degradation. Studies have shown that MHC-class-1-like Fcγ receptor FcRn is capable of rescuing immunoglobulins from lysosomal degradation by recycling it back to the cell surface from the sorting endosome. Simister and Mostov (1989) An Fc receptor structurally related to MHC class I antigens. Nature 337: 184-87. As explained above, to improve efficiency of antibody recycling, further modifications to antibody sequences, e.g., modifications that result in decreased antigen binding at acidic pH (e.g., pH of the endosome), while retaining antibody-antigen affinity and specificity at neutral pH (e.g., physiological pH) are beneficial. The non-human animals described herein, wherein histidine residues are substituted for non-histidine residues in the a universal light chain sequence are beneficial because they are capable of producing high-affinity antibodies based on universal light chain format that also display pH-dependent binding, e.g., display reduced binding to the antigen at acidic versus neutral pH.

Thus, in one embodiment, provided herein is a non-human animal (e.g., a rodent, e.g., a mouse or a rat) that comprises in its genome, e.g., in its germline, a limited repertoire of human light chain variable regions, or a single human light chain variable region, from a limited repertoire of human light chain variable gene segments, wherein the human light chain variable region(s) comprise at least one substitution of a non-histidine codon for a histidine codon. In some embodiments, provided non-human animals are genetically engineered to include a single unrearranged human light chain variable region gene segment (or two human light chain variable region gene segments) that rearranges to form a rearranged human light chain variable region gene (or two rearranged light chain variable region genes) that expresses a single light chain (or that express either or both of two light chains), wherein the light chain variable region gene(s) comprise a substitution of at least one non-histidine codon with a histidine codon. The rearranged human light chain variable domains encoded by these histidine-substituted light chain variable region gene(s) are capable of pairing with a plurality of affinity-matured human heavy chains selected by the animals, wherein the heavy chain variable regions specifically bind different epitopes. In various embodiments, the at least one substitution of a non-histidine residue with a histidine residue results in a rearranged human light chain that, when expressed with a cognate heavy chain, binds to its antigen in a pH-dependent manner.

Genetically engineered animals are provided that express a limited repertoire of human light chain variable domains, or a single human light chain variable domain, from a limited repertoire of human light chain variable region gene sequences, wherein the variable region gene sequences comprise at least one substitution of a non-histidine codon with a histidine codon. In some embodiments, provided animals are genetically engineered to include a single V/J human light chain sequence (or two V/J sequences) that comprises a substitution of at least one non-histidine codon with a histidine codon and expresses a variable region of a single light chain (or that express either or both of two variable regions). In one aspect, a light chain comprising the variable sequence is capable of pairing with a plurality of affinity-matured human heavy chains clonally selected by the animal, wherein the heavy chain variable regions specifically bind different epitopes. In one embodiment, the antibody binds to its antigen(s) in a pH-dependent manner. In one embodiment, the single V/J human light chain sequence is selected from Vκ1-39Jκ5 and Vκ3-20Jκ1. In one embodiment, the two V/J sequences are Vκ1-39Jκ5 and Vκ1-20Jκ1. In one embodiment, the Vκ3-39Jκ5 and Vκ3-20Jκ1 sequences are rearranged V/J sequences.

In one aspect, a genetically modified non-human animal is provided that comprises a single human immunoglobulin light chain $V_L$ gene segment that is capable of rearranging with a human $J_L$ gene segment (selected from one or a plurality of $J_L$ segments) and encoding a human variable domain of an immunoglobulin light chain, wherein the single human immunoglobulin light chain $V_L$ gene segment and/or human $J_L$ gene segment comprise a substitution of at least one non-histidine codon with a histidine codon. In another aspect, a genetically modified mouse is provided that comprises no more than two human $V_L$ gene segments, each of which is capable of rearranging with a human $J_L$ gene segment (selected from one or a plurality of $J_L$ segments) and encoding a human variable domain of an immunoglobulin light chain, wherein each of the no more than two $V_L$ gene segments and/or the $J_L$ gene segment comprise a substitution of at least one non-histidine residue with a histidine residue.

Also provided herein is a genetically modified non-human animal that comprises in its genome, e.g., in its germline, a single rearranged human immunoglobulin light chain variable region sequence comprising human $V_L$ and $J_L$ sequences wherein the single rearranged human immunoglobulin light chain variable region comprises a substitution of at least one non-histidine codon with a histidine codon. In one aspect, the single rearranged human immunoglobulin light chain variable region sequence is derived from human germline $V_L$ and $J_L$ gene sequences, but for the histidine substitution(s). In one embodiment, the human immunoglobulin light chain is a human immunoglobulin κ chain. Thus, in one embodiment, the human $V_L$ gene sequence is selected from Vκ1-39 and Vκ3-20. In one embodiment, the single rearranged human immunoglobulin light chain variable region sequence comprises rearranged Vκ1-39/J or Vκ3-20/J sequence. In one embodiment, the human $J_L$ gene sequence is selected from Jκ1, Jκ2, Jκ3, Jκ4, and Jκ5. In one embodiment the human $J_L$ sequence is selected from Jκ1 and Jκ5. In one embodiment, the single rearranged human immunoglobulin light chain variable region sequence is selected from Vκ1-39Jκ5 and Vκ3-20Jκ1 (e.g., but for the histidine substitution(s)). In an alternative embodiment, the human immunoglobulin light chain is a human λ chain.

In one embodiment, the substitution of at least one non-histidine codon for a histidine codon is in the nucleotide sequence encoding a complementary determining region (CDR) of the light chain variable domain. In one embodiment, the substitution of at least one non-histidine codon for a histidine codon is in the nucleotide sequence encoding CDR1, CDR2 or CDR3 of the light chain variable domain. In one specific embodiment, the substitution is in the nucleotide sequence encoding CDR3.

In one aspect, the substitution is of at least one non-histidine codon for a histidine codon in the CDR3 codon of the human light chain variable region gene sequence. In one embodiment, the substitution is of one, two, three, four, or more CDR3 codons. In the embodiment wherein the single rearranged human immunoglobulin light chain variable region is a Vκ1-39Jκ5 variable region, the replacement of at least one non-histidine codon with a histidine codon comprises a replacement at a position in the immunoglobulin light chain gene sequence encoding CDR3 designed to express a histidine at position selected from 105, 106, 108, 111, and a combination thereof. In one embodiment, the replacement is designed to express histidines at positions 105 and 106. In one embodiment, the replacement is designed to express histidines at positions 105 and 111. In one embodiment, the replacement is designed to express histidines at positions 105 and 108. In one embodiment, the replacement is designed to express histidines at positions 105, 108 and 111. In one embodiment, the replacement is designed to express histidines at positions 105, 106, and 108. In one embodiment, the replacement is designed to express histidines at positions 106 and 108. In one embodiment, the replacement is designed to express histidines at positions 106 and 111. In one embodiment, the replacement is designed to express histidines at positions 108 and 111. In one embodiment, the replacement is designed to express histidines at positions 106, 108, and 111. In yet another embodiment, the replacement is designed to express histidines at positions 106, 108 and 111. In one embodiment, the replacement is designed to express histidines at positions 105, 106, and 111. In one embodiment, the replacement is designed to express histidines at positions 105, 106, 108, and 111. The nucleic acid and amino acid sequences of the histidine-substituted CDR3 regions are depicted in sequence alignment of FIG. 2 and set forth in SEQ ID NOs: 4-33. Wild type CDR3 nucleic acid and amino acid sequences (depicted in FIG. 2) are set forth in SEQ ID NOs:2 and 3, respectively.

In the embodiment wherein the single rearranged human immunoglobulin light chain variable region is a Vκ3-20Jκ1 variable region, the replacement of at least one non-histidine codon with a histidine codon comprises a replacement at a position in the immunoglobulin light chain gene sequence encoding CDR3 region that is designed to express a histidine at position selected from 105, 106, 107, 109, and a combination thereof. In one embodiment, the replacement is designed to express histidines at positions 105 and 106. In one embodiment, the replacement is designed to express histidines at positions 105 and 107. In one embodiment, the replacement is designed to express histidines at positions 105 and 109. In one embodiment, the replacement is designed to express histidines at positions 106 and 107. In one embodiment, the replacement is designed to express histidines at positions 106 and 109. In one embodiment, the replacement is designed to express histidines at positions 107 and 109. In one embodiment, the replacement is designed to express histidines at positions 105, 106, and 107. In one embodiment, the replacement is designed to express histidines at positions 105, 107, and 109. In one embodiment, the replacement is designed to express histidines at positions 106, 108, and 111. In one embodiment, the replacement is designed to express histidines at positions 105, 106 and 109. In another embodiment, the replacement is designed to express histidines at positions 105, 106, 107, and 109. The nucleic acid and amino acid sequences of exemplary histidine-substituted CDR3 regions are depicted in sequence alignment of FIG. 12 and set forth in SEQ ID NOs: 76-79. Wild type CDR3 nucleic acid and amino acid sequences (depicted in FIG. 12) are set forth in SEQ ID NOs:74 and 75, respectively.

Amino acid positions (105, 106, etc.) are based on a unique numbering described in Lefranc et al. (2003) Dev. Comp. Immunol. 27:55-77, and can also be viewed on www.imgt.org.

In one embodiment, the human $V_L$ gene segment is operably linked to a human or non-human leader sequence. In one embodiment, the leader sequence is a non-human leader sequence. In a specific embodiment, the non-human leader sequence is a mouse Vκ3-7 leader sequence. In a specific embodiment, the leader sequence is operably linked to an unrearranged human $V_L$ gene segment. In a specific embodiment, the leader sequence is operably linked to a rearranged human $V_L/J_L$ sequence. Thus, in one specific embodiment, the single rearranged Vκ1-39/Jκ5 or Vκ3-20/Jκ1 variable region gene sequence comprising at least one histidine substitution is operably linked to a mouse Vκ3-7 leader sequence.

In one embodiment, the $V_L$ gene segment is operably linked to an immunoglobulin promoter sequence. In one embodiment, the promoter sequence is a human promoter sequence. In a specific embodiment, the human immunoglobulin promoter is a human Vκ3-15 promoter. In a specific embodiment, the promoter is operably linked to an unrearranged human $V_L$ gene segment. In a specific embodiment, the promoter is operably linked to a rearranged human $V_L/J_L$ sequence. Thus, in one specific embodiment, the single rearranged Vκ1-39/Jκ5 or Vκ3-20/Jκ1 variable region gene sequence comprising at least one histidine substitution is operably linked to the human Vκ3-15 promoter.

In one embodiment, the light chain locus comprises a leader sequence flanked 5' (with respect to transcriptional direction of a $V_L$ gene segment) with a human immunoglobulin promoter and flanked 3' with a human $V_L$ gene segment that rearranges with a human $J_L$ segment and encodes a variable domain of a reverse chimeric light chain comprising an endogenous non-human light chain constant region ($C_L$). In a specific embodiment, the $V_L$ and $J_L$ gene segments are at the non-human Vκ locus, and the non-human $C_L$ is a non-human Cκ (e.g., mouse Cκ). In one specific embodiment, the variable region sequence is operably linked to the non-human constant region sequence, e.g., the non-human Cκ gene sequence.

In one embodiment, the light chain locus comprises a leader sequence flanked 5' (with respect to transcriptional direction of a $V_L$ gene segment) with a human immunoglobulin promoter and flanked 3' with a rearranged human variable region sequence ($V_L/J_L$ sequence) and encodes a variable domain of a reverse chimeric light chain comprising an endogenous non-human light chain constant region ($C_L$). In a specific embodiment, the rearranged human $V_L/J_L$ sequence is at the non-human kappa (κ) locus, and the non-human $C_L$ is a non-human Cκ. In one specific embodiment, the rearranged human variable region sequence is operably linked to the non-human immunoglobulin light chain constant region sequence, e.g., the non-human Cκ gene sequence. In one embodiment, the non-human immunoglobulin light chain constant region sequence is an endogenous non-human sequence. In one embodiment, the non-human animal is a mouse and the Cκ gene sequence is a mouse Cκ gene sequence. In one embodiment, the rearranged human immunoglobulin light chain variable region sequence comprising a substitution of at least one non-histidine codon with a histidine codon is at the endogenous non-human (e.g., mouse) immunoglobulin light chain locus (κ locus). Exemplary embodiments of the locus are presented in FIGS. 8C, 8E, 14C, and 14D.

In one embodiment, the genetically modified non-human animal is a mouse, and the variable region locus of the mouse is a κ light chain locus, and the κ light chain locus comprises a mouse κ intronic enhancer, a mouse κ3' enhancer, or both an intronic enhancer and a 3' enhancer.

In one embodiment, the non-human animal (e.g., a rodent, e.g., a rat or a mouse) comprises a nonfunctional immunoglobulin lambda (λ) light chain locus. In a specific embodiment, the light chain locus comprises a deletion of one or more sequences of the locus, wherein the one or more deletions renders the λ light chain locus incapable of rearranging to form a light chain gene. In another embodiment, all or substantially all of the $V_L$ gene segments of the λ light chain locus are deleted. In one embodiment, the non-human animal (e.g., rodent, e.g. mouse or rat) comprises a rearranged human immunoglobulin light chain variable region sequence comprising a substitution of at least one non-histidine codon with a histidine codon, and lacks a functional unrearranged immunoglobulin light chain variable region, e.g., endogenous unrearranged light chain variable region. In one embodiment, the rearranged, histidine-substituted human immunoglobulin light chain variable region gene sequence replaces endogenous unrearranged immunoglobulin light chain variable region gene sequence.

In one embodiment, the animal makes a light chain that comprises a somatically mutated variable domain derived from a human variable region sequence that comprises a substitution of at least one non-histidine codon with a histidine codon. In one embodiment, the light chain comprises a somatically mutated variable domain derived from a human variable region sequence that comprises a substitution of at least one non-histidine codon with a histidine codon, and a non-human Cκ region. In one embodiment, the non-human animal does not express a λ light chain.

One skilled in the art would appreciate that although substitution(s) of at least one non-histidine residue with a histidine residue is genetically engineered into the human immunoglobulin light chain variable region, due to somatic hypermutations, not all antibodies that are generated in the genetically modified non-human animal will harbor that histidine residue(s) at engineered position(s). However, generation of a wide repertoire of antibodies in the non-human animal will allow to select for in vivo generated antigen-specific antibodies that display high affinity for an antigen of interest while retaining histidine modifications introduced into the germline and, preferably, exhibiting pH-dependent antigen binding.

Thus, in one embodiment, the animal retains at least one histidine amino acid introduced by substitution of at least one non-histidine codon with a histidine codon in its variable region gene. In one embodiment, the animal retains all or substantially all histidine substitutions in its somatically mutated light chain variable domain that were introduced into its variable region gene.

In one embodiment, the genetically modified non-human animal described herein also comprises in its genome, e.g., in its germline, an unrearranged immunoglobulin heavy chain variable region comprising $V_H$, $D_H$, and $J_H$ gene segment sequences. In one embodiment, the $V_H$, $D_H$, and $J_H$ gene segment sequences are human $V_H$, $D_H$, and $J_H$ gene segment sequences, and the unrearranged immunoglobulin heavy chain variable region is a human heavy chain variable region. In one embodiment, the human $V_H$, $D_H$, and $J_H$ gene segment sequences are operably linked to non-human heavy chain constant region sequence. In one embodiment, the non-human heavy chain constant region sequence is an endogenous non-human heavy chain constant region sequence. In one embodiment, the human heavy chain gene segment sequences are at the endogenous non-human immunoglobulin heavy chain locus. In one embodiment, the human immunoglobulin heavy chain variable region sequence comprised in a non-human animal also comprises a substitution of at least one non-histidine codon for a histidine codon.

In one embodiment, the non-human animal described herein expresses an immunoglobulin light chain that comprises a non-human light chain constant region sequence. In one embodiment, the non-human animal expresses an immunoglobulin light chain that comprises a human light chain constant region sequence.

In one embodiment, the non-human animal described herein expresses an immunoglobulin heavy chain that comprises a non-human sequence selected from a $C_H1$ sequence, a hinge sequence, a $C_H2$ sequence, a $C_H3$ sequence, and a combination thereof.

In one embodiment, the non-human animal expresses an immunoglobulin heavy chain that comprises a human sequence selected from a $C_H1$ sequence, a hinge sequence, a $C_H2$ sequence, a $C_H3$ sequence, and a combination thereof.

In the embodiment where the animal comprises a single rearranged immunoglobulin light chain variable region comprising a substitution of at least one non-histidine codon with a histidine codon, the rearranged immunoglobulin light chain sequence in the germline of the animal is at an endogenous non-human immunoglobulin light chain locus. In a specific embodiment, the rearranged immunoglobulin light chain sequence comprising a substitution of at least one non-histidine codon with a histidine codon in the germline of the animal replaces all or substantially all endogenous non-human light chain V and J segment sequences at the endogenous non-human immunoglobulin light chain locus.

In one embodiment, the non-human animal comprises a replacement of endogenous $V_H$ gene segments with one or more human $V_H$ gene segments, wherein the human $V_H$ gene segments are operably linked to a non-human $C_H$ region gene, such that the non-human animal rearranges the human $V_H$ gene segments and expresses a reverse chimeric immunoglobulin heavy chain that comprises a human $V_H$ domain and a non-human $C_H$. In one embodiment, 90-100% of unrearranged non-human $V_H$ gene segments are replaced with at least one unrearranged human $V_H$ gene segment. In a specific embodiment, all or substantially all (e.g., 90-100%) of the endogenous non-human $V_H$ gene segments are replaced with at least one unrearranged human $V_H$ gene segment. In one embodiment, the replacement is with at least 19, at least 39, or at least 80 or 81 unrearranged human $V_H$ gene segments. In one embodiment, the replacement is with at least 12 functional unrearranged human $V_H$ gene segments, at least 25 functional unrearranged human $V_H$ gene segments, or at least 43 functional unrearranged human $V_H$ gene segments. In one embodiment, the non-human animal comprises a replacement of all non-human $D_H$ and $J_H$ segments with at least one unrearranged human $D_H$ segment and at least one unrearranged human $J_H$ segment. In one embodiment, the non-human animal comprises a replacement of all non-human $D_H$ and $J_H$ segments with all unrearranged human $D_H$ segments and all unrearranged human $J_H$ segments.

A non-human animal, e.g., a mouse, comprising in its genome, e.g., in its germline, a limited repertoire of human immunoglobulin light chain variable regions, e.g., a single rearranged human immunoglobulin light chain variable region (e.g., Vκ1-39/Jκ5 or Vκ3-20/Jκ1), with a substitution of at least one non-histidine codon with a histidine codon and a diverse repertoire of unrearranged human $V_H$, $D_H$, and $J_H$ segments is capable of generating antigen binding proteins encoded by heavy chain variable region sequences derived from various permutations of unrearranged human $V_H$, $D_H$, and $J_H$ segments, wherein the $V_H$, $D_H$, and $J_H$ segments present in the heavy chain variable sequences are derived from all or substantially all functional human $V_H$, $D_H$, and $J_H$ segments present in the genome of the animal. Various available possibilities for heavy chain variable domain sequences expressed in the cells, e.g., B cells, of the genetically modified animals described herein (i.e., derived from combinations of various functional human V, D, and J segments) are described in U.S. Application Publication Nos. 2011/0195454, 2012/0021409, 2012/0192300 and 2013/0045492, all incorporated herein by reference. In various embodiments, the rearranged human immunoglobulin light chain variable region sequence comprising substitution(s) of at least one non-histidine codon with a histidine codon and the unrearranged human immunoglobulin heavy chain variable region sequence are comprised in the germline of the non-human animal.

In one embodiment, the non-human animal comprises one copy of one or both of the rearranged human immunoglobulin light chain variable region sequence comprising substitution(s) of at least one non-histidine codon with a histidine codon and the unrearranged human immunoglobulin heavy chain variable region sequence. In another embodiment, the non-human animal comprises two copies of one or both of the rearranged human immunoglobulin light chain variable region sequence comprising substitution(s) of at least one non-histidine codon with a histidine codon and the unrearranged human immunoglobulin heavy chain variable region sequence. Thus, the non-human animal may be homozygous or heterozygous for one or both the rearranged human immunoglobulin light chain variable region sequence comprising substitution(s) of at least one non-histidine codon with a histidine codon and the unrearranged human immunoglobulin heavy chain variable region sequence.

In addition to genetically modified non-human animals comprising in their genome an immunoglobulin light chain variable region gene sequence (e.g., a single rearranged immunoglobulin light chain variable region gene sequence)

comprising substitution of at least one non-histidine codon with a histidine codon (e.g., in CDR3 of the light chain), also provided herein are genetically modified non-human animals comprising an immunoglobulin light chain variable region gene sequence with one or more additions/insertions of histidine codon(s), such that the expressed variable domain comprises an additional amino acid(s) which, if not subject to somatic hypermutation, is a histidine.

The genetically modified non-human animal comprising a human immunoglobulin light chain variable region gene sequence with a substitution of at least one non-histidine codon with a histidine codon described herein may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, methods distinct from those described herein are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the genetically modified non-human animal is a rodent. In one embodiment, the genetically modified non-human animal is a rat or a mouse. In one embodiment, the animal is a mouse. Thus, in one embodiment, provided herein is a genetically modified mouse comprising in its genome, e.g., in its germline, a single rearranged human immunoglobulin light chain variable region comprising human $V_L$ and $J_L$ gene sequences, wherein the single rearranged human immunoglobulin light chain variable region comprises a substitution of at least non-histidine codon with a histidine codon. In one embodiment, the mouse lacks a functional unrearranged immunoglobulin light chain variable region (e.g., lacks functional unrearranged V and J gene segment sequences). In one embodiment, the rearranged human immunoglobulin light chain variable region with histidine codon substitution(s) is Vκ1-39/Jκ or Vκ3-20/Jκ variable region. In one embodiment the J segment sequence is selected from Jκ1, Jκ2, Jκ3, Jκ4, and Jκ5. In one embodiment the J segment sequence is Jκ1 or Jκ5. In one embodiment, the substitution of at least one non-histidine codon with a histidine codon is in the nucleotide sequence encoding a CDR3 region. In one embodiment, wherein the rearranged variable region sequence is Vκ1-39/Jκ5 sequence, the histidine substitution(s) is designed to express at a position selected from 105, 106, 108, 111, and a combination thereof. In another embodiment, wherein the rearranged variable region sequence is Vκ3-20/Jκ1 sequence, the histidine substitution(s) is designed to express at a position selected from 105, 106, 107, 109, and a combination thereof. In one embodiment, the rearranged immunoglobulin light chain variable region with substituted histidine codon(s) is operably linked to an endogenous mouse immunoglobulin constant region gene sequence (e.g., Cκ gene sequence). In one embodiment, the mouse further comprises in its genome, e.g., in its germline, an unrearranged immunoglobulin heavy chain variable region comprising human $V_H$, $D_H$, and $J_H$ segments. In one embodiment, human $V_H$, $D_H$, and $J_H$ segments are operably linked to an endogenous mouse immunoglobulin heavy chain constant region gene sequence. In various embodiments, the rearranged human immunoglobulin light chain variable region sequence comprising substitution(s) of at least one non-histidine codon with a histidine codon and the unrearranged human immunoglobulin heavy chain variable region sequence are comprised in the germline of the mouse.

Also provided herein are targeting vectors for generating genetically modified non-human animals, e.g., mice, described herein. In one aspect, provided is a targeting vector comprising, from 5' to 3' in transcriptional direction with reference to the sequences of the 5' and 3' mouse homology arms of the vector, a 5' mouse homology arm, a human or mouse immunoglobulin promoter, a human or mouse leader sequence, a human variable region selected from a rearranged human Vκ1-39Jκ5 or a rearranged human Vκ3-20Jκ1 and comprising a substitution of at least one non-histidine codon with a histidine codon, and a 3' mouse homology arm. In one embodiment, the 5' and 3' homology arms target the vector to a sequence 5' with respect to an enhancer sequence that is present 5' and proximal to the mouse Cκ gene. In another embodiment, the targeting vector comprises a 5' mouse homology arm followed by a selection cassette flanked by recombination sites, human or mouse immunoglobulin promoter, human or mouse leader sequence, a human variable region selected from a rearranged human Vκ1-39Jκ5 or a rearranged human Vκ3-20Jκ1 and comprising a substitution of at least one non-histidine codon with a histidine codon, followed by the 3' mouse homology arm that comprises mouse enhancers and constant region (Cκ) sequences.

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, Spec, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art.

In one embodiment, the promoter is a human immunoglobulin variable region gene segment promoter. In a specific embodiment, the promoter is a human Vκ3-15 promoter. In one embodiment, the leader sequence is a mouse leader sequence. In a specific embodiment, the mouse leader sequence is a mouse Vκ3-7 leader sequence. Exemplary embodiments of the targeting vectors are presented in FIGS. 8B and 14B.

In one aspect, a targeting vector is provided as described above, but in place of the 5' mouse homology arm the human or mouse promoter is flanked 5' with a site-specific recombinase recognition site (SRRS), and in place of the 3' mouse homology arm the human $V_L$ region is flanked 3' with an SRRS.

Also provided herein are methods of making genetically modified non-human animals (e.g., rodents, e.g., mice or rats) described herein. In one aspect, the method for making a genetically modified non-human animal described herein utilizes a targeting vector, made using VELOCIGENE® technology, introducing the construct into ES cells, and introducing targeted ES cell clones into a mouse embryo using VELOCIMOUSE® technology, as described in the Examples. Histidine modifications may be introduced into the targeting vector using a variety of molecular biology techniques, e.g., site directed mutagenesis or de novo DNA synthesis. Upon completion of gene targeting, ES cells of genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCT (e.g., real-time PCR using TAQ-MAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

Thus, in one embodiment, the method of generating genetically modified non-human animals comprises replacing an immunoglobulin light chain variable region gene sequence in the animal with a human immunoglobulin light chain variable region gene sequence (comprising human $V_L$ and $J_L$ gene segments) wherein the human immunoglobulin variable region gene sequence comprises a substitution of at least one non-histidine codon with a histidine codon. In one embodiment, the substitution of at least one non-histidine codon with a histidine codon is in the nucleotide sequence encoding a CDR region, e.g., a CDR3 region.

In one embodiment, the method of generating genetically modified non-human animals described herein comprises replacing an immunoglobulin light chain variable region gene sequence in the animal with a single rearranged human immunoglobulin light chain variable region gene sequence comprising human $V_L$ and $J_L$ gene segment sequences, wherein the single rearranged human immunoglobulin variable region gene sequence comprises a substitution of at least one non-histidine codon with a histidine codon. In one embodiment, the substitution is in a CDR codon. In one embodiment, the substitution is of one, two, three, four, or more CDR3 codon(s). In one embodiment, the single rearranged human immunoglobulin light chain variable region gene sequence is based on the human germline rearranged light chain variable region sequence selected from Vκ1-39Jκ5 and Vκ3-20Jκ1. Thus, in one embodiment, where the single rearranged human immunoglobulin light chain variable region gene sequence is derived from Vκ1-39Jκ5, replacement of at least one non-histidine codon with histidine codon is designed to express a histidine at positions selected from 105, 106, 108, 111, and a combination thereof. In one embodiment, where the single rearranged human immunoglobulin light chain variable region gene sequence is derived from Vκ3-20κ1, replacement of at least one non-histidine codon with a histidine codon is designed to express a histidine at position selected from 105, 106, 107, 109, and a combination thereof.

In another embodiment, the method of generating a non-human animal described herein (i.e., comprising a genetically modified immunoglobulin light chain locus described herein) comprises modifying a genome of a non-human animal to delete or render nonfunctional endogenous immunoglobulin light chain V and J segments in an immunoglobulin light chain locus, and placing in the genome a single rearranged human light chain variable region gene sequence comprising a substitution of at least one non-histidine codon with a histidine codon. In one embodiment, the method results in a genetically modified non-human animal that comprises a population of B cells enriched for antibodies exhibiting pH dependent binding to an antigen of interest.

In some embodiments, the methods of generating genetically modified non-human animals described herein comprise replacing an immunoglobulin light chain variable region gene sequence with human immunoglobulin light chain variable gene region sequence comprising substitution(s) of at least one non-histidine codon with a histidine codon in the animal that also comprises a replacement of endogenous non-human immunoglobulin heavy chain variable region gene sequence with a human immunoglobulin heavy chain variable region gene sequence comprising at least one of each or a repertoire of human $V_H$, $D_H$, and $J_H$ sequences, as described above. In one embodiment, in order to generate a non-human animal comprising a replacement of endogenous immunoglobulin light chain variable region gene sequence human light chain variable region gene sequence comprising a substitution of at least one non-histidine codon with a histidine codon and a replacement of endogenous non-human immunoglobulin heavy chain variable region gene sequence with a human immunoglobulin heavy chain variable region gene sequence, the animal with replacement of light chain variable region gene sequence is bred to an animal with replacement of heavy chain variable region gene sequence.

Inventors presently provide genetically engineered non-human animals (e.g., rodents, e.g., rats or mice) that express antigen-binding proteins, e.g., antibodies, that comprise a universal light chain, e.g., a human universal light chain (e.g., a light chain derived from a single rearranged human immunoglobulin light chain variable region) that comprises one or more histidine modifications, wherein the antigen-binding proteins exhibit a pH-dependent antigen binding of a target antigen. The animals are genetically engineered to include a light chain CDR3 that comprises one or more histidine modifications. In various embodiments, the light chain CDR3 comprises two, three, or four or more histidine residues in a cluster.

In one embodiment, provided herein is a genetically engineered non-human animal (e.g., a mouse or a rat) that comprises a population of B cells characterized by enhanced presence of histidines in immunoglobulin light chains, e.g., immunoglobulin variable domains, e.g., immunoglobulin CDRs, compared to a wild type animal. In one embodiment, enhancement of histidine presence is about 2 to 4 fold. In one embodiment, enhancement of histidines is about 2 to 10 fold.

In one embodiment, provided herein is a genetically engineered non-human animal that comprises a population of antigen-specific antibodies that express histidine residue(s) as a result of codon modifications in the light chain variable region gene sequence, and display pH-dependent binding of target antigen. In one embodiment, these animals comprise a population of B cells that are enriched for antibodies, e.g., antigen-specific antibodies, that display pH-dependent binding properties (e.g., decreased dissociative half-life ($t_{1/2}$), at acidic pH vs neutral pH) as compared to a population of antigen-specific antibodies generated in animals that do not comprise a substitution of at least one non-histidine codon with a histidine codon in immunoglobulin light chain variable region described herein. In one embodiment, the enrichment of antigen-specific antibodies displaying pH-dependent antigen binding properties generated in the genetically engineered animals described herein as compared to similar animals that do comprise histidine substitutions in light chain variable region is greater than about 2 fold, e.g., greater than about 5 fold, e.g., greater than about 10 fold. Thus, the genetically modified animals of the invention are enriched for antibodies with improved antibody recycling properties, which is desired in order to reduce target-mediated clearance as well as to reduce the dose and/or dosing frequency of a therapeutic antigen-binding protein developed based on such in vivo generated antibody format.

Thus, provided herein is an antigen-binding protein, generated in genetically modified non-human animals described herein, wherein the antigen-binding protein displays pH-dependent antigen binding. In one embodiment, the antigen-binding protein is an antibody, e.g., antigen-specific antibody. In one embodiment, the antibody comprises a light chain which comprises a human light chain variable domain derived from a rearrangement of human immunoglobulin light chain variable gene segments where at least one non-histidine codon was substituted for a histidine codon in the germline gene sequence, and wherein the antibody retains at least one histidine substitution in its expressed human light chain variable domain. In one embodiment, the antibody comprises a light chain which comprises a human light chain variable domain derived from a single rearranged human light chain variable region gene sequence, wherein the single rearranged light chain variable region gene sequence comprises a substitution of at least one non-histidine codon with a histidine codon, and wherein the antibody retains at least one histidine substitution in its expressed light chain variable domain. In one embodiment, the antibody comprises a light chain derived from a human Vκ1-39Jκ5 or Vκ3-20Jκ1 rearrangement, wherein the human Vκ1-39Jκ5 or Vκ3-20Jκ1 gene sequence comprises a substitution of at least one non-histidine codon with a histidine codon, and wherein the antibody retains at least one histidine substitution in its expressed light chain variable domain. In some embodiments, the antibody retains all or substantially all histidine substitutions in its expressed light chain variable domain. In one embodiment, the substitution is of three non-histidine codons with three histidine codons in the nucleotide sequence encoding CDR3 of the light chain variable region gene sequence, and the antibody retains all three histidine substitutions in its expressed light chain variable domain. In one embodiment, the substitution is of four non-histidine codons with four histidine codons in the nucleotide sequence encoding CDR3 of the light chain variable region gene sequence, and the antibody retains three or four histidine substitutions in its expressed light chain variable domain.

In one embodiment, the light chain of the antibody further comprises a non-human light chain constant region amino acid sequence, e.g., endogenous light chain constant region amino acid sequence. In addition, the antibody, e.g., antigen-specific antibody, generated in a genetically modified non-human animal described herein also comprises a heavy chain which comprises a human heavy chain variable domain derived from a rearrangement of human heavy chain V, D, and J segments. Human heavy chain V, D, and J segments may be selected from a repertoire of human heavy chain segments present at the endogenous non-human heavy chain locus, e.g., at least one functional V, at least one functional D, and at least one functional J segment, e.g., up to a complete repertoire of functional human V, D, and J segments. Exemplary possible rearrangements of human heavy chain variable segments may be gleaned from a listing of functional human V, D, and J segments in IMGT database, and from U.S. Application Publication Nos. 2011/0195454, 2012/0021409, 2012/0192300, and 2013/0045492, incorporated herein by reference. Furthermore, in one embodiment, the heavy chain of the antibody comprises a non-human heavy chain constant region amino acid sequence, e.g., an endogenous non-human heavy chain constant region amino acid sequence. In one embodiment, the non-human heavy chain constant region comprises $C_H1$, hinge, $C_H2$, and $C_H3$ domains. In one embodiment, the antibody is an IgG, IgE, IgD, IgM, or IgA isotype.

Thus, in one embodiment, provided herein is a binding protein generated in the genetically modified non-human animals described herein, wherein the binding protein comprises a reverse chimeric light chain comprising (a) a light chain variable domain derived from a human Vκ1-39Jκ5 rearrangement comprising a substitution of at least one non-histidine codon with a histidine codon, wherein the light chain retains at least one histidine substitution in its expressed light chain variable domain and (b) a non-human, e.g., a mouse, light chain constant region amino acid sequence, wherein the light chain is associated with a reverse chimeric heavy chain comprising (a) a heavy chain variable domain derived from a rearrangement of human V, D, and J segments, wherein the V, D, and J segments are selected from a repertoire of human V, D, and J segments present in the animal, and (b) a non-human, e.g., mouse, heavy chain constant region amino acid sequence. In one embodiment, the repertoire of human V, D, and J segments comprises at least one functional V, at least one functional D, and at least one functional J segment, e.g., up to a complete repertoire of functional human V, D, and J segments. In one embodiment, the heavy and the light chain constant domains are endogenous heavy and light chain constant regions. In one embodiment, the heavy and light chain variable domains are somatically mutated domains. In one embodiment, the somatically mutated light chain domain retains at least one histidine substitution introduced into the germline sequence. In some embodiments, the somatically mutated light chain domain retains all or substantially all histidine substitutions introduced into the germline sequence. In one embodiment, the antigen-binding protein displays pH-dependent antigen binding properties.

In another embodiment, provided herein is a binding protein generated in the genetically modified non-human animals described herein, wherein the binding protein comprises a reverse chimeric light chain comprising (a) a light chain variable domain derived from a human Vκ3-20Jκ1 rearrangement comprising a substitution of at least one non-histidine codon with a histidine codon, wherein the light chain retains at least one histidine substitution in its expressed light chain variable domain and (b) a non-human, e.g., a mouse, light chain constant region amino acid sequence, wherein the light chain is associated with a reverse chimeric heavy chain comprising (a) a heavy chain variable domain derived from a rearrangement of human V, D, and J segments, wherein the V, D, and J segments are selected from a repertoire of human V, D, and J segments present in the animal, and (b) a non-human, e.g., mouse, heavy chain constant region amino acid sequence. In one embodiment, the repertoire of human V, D, and J segments comprises at least one functional V, at least one functional D, and at least one functional J segment, e.g., up to a complete repertoire of functional human V, D, and J segments. In one embodiment, the heavy and the light chain constant regions are endogenous heavy and light chain constant regions. In one embodiment, the heavy and light chain variable domains are somatically mutated domains. In one embodiment, the somatically mutated light chain domain retains at least one histidine substitution introduced into the germline sequence. In some embodiments, the somatically mutated light chain domain retains all or substantially all histidine substitutions introduced into the germline sequence. In one embodiment, the antigen-binding protein displays pH-dependent antigen binding properties.

In one embodiment, also provided herein is a B cell of the genetically modified animal described herein, that comprises in its germline a histidine-modified human light chain variable region sequence, e.g., a histidine-modified single rearranged human light chain variable region sequence, described herein, and expresses an antigen-binding protein described herein. In one embodiment, the antigen-binding protein, e.g., an antibody, expressed in the B cell retains at least one histidine residue introduced into the germline, and displays pH-dependent antigen-binding properties. In some embodiments, the antigen-binding protein, e.g., an antibody, expressed in the B cell retains all or substantially all histidine residues introduced into the germline, and displays pH-dependent antigen-binding properties.

In various embodiments, the genetically modified non-human animal described herein comprises a human light chain variable region gene sequence, e.g., a single rearranged human light chain variable region gene sequence (e.g., Vκ1-39Jκ5 or Vκ3-20Jκ1 sequence) that comprises a substitution of at least one non-histidine codon with a histidine codon (or an addition of a histidine codon into the germline sequence). These additions or substitutions result in a non-human animal that comprises a population of B cells enriched for antigen-binding proteins with pH dependent binding properties for their antigens. In one embodiment, antigen-binding proteins, e.g., antibodies, generated in the non-human animals described herein in response to antigen stimulation display pH dependent antigen binding while exhibiting high affinity for the antigen at neutral pH, e.g., pH between about 7.0 and about 8.0, e.g., pH between about 7.0 and about 7.4, e.g., between about 7.2 and about 7.4, e.g., physiological pH. In one embodiment, the affinity of the antigen-binding protein to its antigen, expressed as a dissociation constant ($K_D$) at a neutral pH is less than $10^{-6}$ M, e.g., less than $10^{-8}$ M, e.g., less than $10^{-9}$ M, e.g., less than $10^{-10}$ M, e.g., less than $10^{-11}$ M, e.g., less than $10^{-12}$ M.

In one embodiment, an antigen-binding protein, e.g., an antibody, generated in the genetically modified non-human animal described herein, exhibits reduced binding to its antigen in acidic pH (e.g., pH of 6.0 or lower, e.g., pH between about 5.0 and about 6.0, pH between about 5.75 and about 6.0, e.g., pH of endosomal or lysosomal compartments) as compared to neutral pH. In one embodiment, the antigen-binding protein, e.g., the antibody, generated in the genetically modified non-human animal described herein, exhibits no binding to the antigen in acidic pH, while retaining binding to the antigen at neutral pH. In one embodiment, an antigen-binding protein generated by the genetically modified non-human animal described herein, has a decrease in dissociative half-life ($t_{1/2}$) at an acidic pH as compared to the dissociative half-life ($t_{1/2}$) of the antigen-binding protein at a neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, an antigen-binding protein expressed by the genetically modified non-human animal described herein has a $t_{1/2}$ at an acidic pH and 37° C. of about 2 min or less. In one embodiment, an antigen-binding protein expressed by the genetically modified non-human animal described herein has a $t_{1/2}$ at an acidic pH and 37° C. of less than about 1 min. In one embodiment, an antigen-binding protein expressed by the genetically modified non-human animal described herein has a $t_{1/2}$ at an acidic pH and 25° C. of about 2 min or less. In one embodiment, an antigen-binding protein expressed by the genetically modified non-human animal described herein has a $t_{1/2}$ at an acidic pH and 25° C. of less than about 1 min.

Kinetic parameters, such as equilibrium dissociation constants ($K_D$) and dissociative half-lives ($t_{1/2}$) can be calculated from kinetic rate constant as: $K_D(M)=k_d/k_a$; and $t_{1/2}(min)=\ln 2/(60*k_d)$.

In one embodiment, the antigen-binding protein, e.g., an antibody, generated in the genetically modified non-human animals described herein, exhibits increased binding to FcRn molecule. As described above, FcRn is a receptor present inside the endosomal compartment that is capable of binding immunoglobulins at an acidic pH and recycling them back to the surface. Screening antibody molecules in the genetically modified non-human animals described herein presents a unique opportunity to select for antibodies with three beneficial parameters: high affinity for an antigen, pH-dependent antigen binding (with weaker antigen binding at acidic pH) and increased binding to FcRn.

In one embodiment, a genetically modified non-human animal described herein comprises a population of B cells in response to an antigen that produces and is enriched for antigen-binding proteins, e.g., antibodies, that, when reformatted into therapeutics, exhibit increased serum half life upon administration of a therapeutic dose to a subject over an equivalent B cell population produced in response to the same antigen in non-human animals that do not comprise histidine modification(s) in their human light chain variable region gene sequences. Thus, in one embodiment, an antigen-binding protein, e.g., an antibody, produced in response to an antigen of interest in a genetically modified non-human animal described herein, when reformatted into a therapeutic, exhibits increased serum half life upon administration of a therapeutic dose to a subject over a serum half life of an antigen-binding protein (when reformatted into a therapeutic and administered at the same therapeutic dose) that was produced in response to the same antigen in a non-human animal that does not comprise histidine modification(s) in its human light chain variable region gene sequence. In some embodiments, the increase in serum half life is about 2 fold, e.g., about 5 fold, e.g., about 10 fold, e.g., about 15 fold, e.g., about 20 fold, or greater.

In one aspect, a pluripotent, induced pluripotent, or totipotent cell derived from a non-human as described herein is provided. In a specific embodiment, the cell is an embryonic stem (ES) cell.

In one aspect, a tissue derived from a non-human animal as described herein is provided. In one embodiment, the tissue is derived from spleen, lymph node or bone marrow of a non-human animal as described herein.

In one aspect, a nucleus derived from a non-human animal as described herein is provided. In one embodiment, the nucleus is from a diploid cell that is not a B cell.

In one aspect, a non-human cell is provided that is isolated from a non-human animal (e.g., a rodent, e.g., a mouse or a rat) as described herein. In one embodiment, the cell is an ES cell. In one embodiment, the cell is a lymphocyte. In one embodiment, the lymphocyte is a B cell. In one embodiment, the B cell expresses a chimeric heavy chain comprising a variable domain derived from a human gene segment; and a light chain derived from a rearranged human Vκ1-39/J sequence with a substitution of at least one non-histidine codon with histidine codon, rearranged human Vκ3-20/J sequence with a substitution of at least one non-histidine codon with histidine codon, or a combination thereof and further comprising a substitution of at least one amino acid encoded in the germline for a histidine; wherein the heavy chain variable domain is fused to a non-human or a human heavy chain constant region and the light chain variable domain is fused to a non-human or a human light chain constant region.

In one aspect, a hybridoma is provided, wherein the hybridoma is made with a B cell of a non-human animal as described herein. In a specific embodiment, the B cell is from a mouse as described herein that has been immunized with an immunogen comprising an epitope of interest, and the B cell expresses a binding protein that binds the epitope of interest, the binding protein has a somatically mutated human variable heavy chain domain and a mouse $C_H$, and has a human variable light chain domain derived from a rearranged human Vκ1-39Jκ5 with a substitution of at least one non-histidine codon with histidine codon or a rearranged human Vκ3-20Jκ1 with a substitution of at least one non-histidine codon with histidine codon and a mouse $C_L$, wherein the human light chain domain comprises a substitution of at least one amino acid encoded in the germline with a histidine.

Also provided is a cell expressing an antigen-binding protein generated in the non-human animals described herein. In one embodiment, the cell is selected from CHO, COS, 293, HeLa, and a retinal cell expressing a viral nucleic acid sequence (e.g., a PERC.6™ cell).

In one aspect, a non-human embryo is provided, wherein the embryo comprises a donor ES cell that is derived from a non-human animal as described herein.

The non-human animals described herein are useful to generate B cells that express antibodies having histidines in a CDR3. An animal that places histidines in a CDR3 is useful for making antibodies in general, and in particular useful for developing antibodies that bind a target with sufficient affinity at or around a neutral pH, but that either do not bind or that bind weaker to the same target at an acidic pH.

The non-human animal is useful to generate variable regions of antibodies that can be used to make, e.g., human therapeutic binding proteins that bind their targets by human immunoglobulin variable domains that comprise the histidines in a CDR3. The altered binding at a lower pH will in some circumstances allow faster turnover because the therapeutic will bind a target on a cell's surface, be internalized in an endosome, and more readily or more rapidly dissociate from the target in the endosome, so that the therapeutic can be recycled to bind yet another molecule of target (e.g., on another cell or the same cell). In some circumstances, this will result in the ability to dose the therapeutic at a lower dose, or dose the therapeutic less frequently. This is particularly useful where it is not desirable to dose frequently, or to administer above a certain dosage, for safety or toxicity reasons. As a result, the serum half life of the antibody therapeutic when administered to a subject will be increased.

The non-human animal, e.g., rodent, e.g., mouse or rat, is useful in a method for increasing the number of B cells in an animal that exhibit an antibody variable region having a CDR3 with one or more histidines in it. The non-human animal is useful for generating antibody sequences that will exhibit pH-dependent antigen binding. The non-human animal is useful for generating a greater number of antibody sequences, resulting from a single immunization, wherein the antibodies will exhibit a pH-dependent antigen binding.

Antigen-Binding Proteins and Methods of Generating the Same

In one aspect, also provided herein are methods for generating human antigen-binding proteins, e.g., antibodies, which exhibit pH-dependent antigen binding, from the genetically modified non-human animals described herein with standard methods used in the art.

Several techniques for producing antibodies have been described. For example, in various embodiments chimeric antibodies are produced in mice as described herein. Antibodies can be isolated directly from B cells of an immunized mouse (e.g., see U.S. 2007/0280945A1) and/or the B cells of the immunized mouse can be used to make hybridomas (Kohler and Milstein, 1975, *Nature* 256:495-497). DNA encoding the antibodies (human heavy and/or light chains) from non-human animals as described herein is readily isolated and sequenced using conventional techniques. Hybridoma and/or B cells derived from non-human animals as described herein serve as a preferred source of such DNA. Once isolated, the DNA may be placed into expression vectors, which are then transfected into host cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the non-human sequences. Thus, once nucleic acid sequences of antibodies with desired characteristics, e.g., affinity, epitope, pH-dependent antigen binding, etc., are determined, the non-human constant region gene sequences are replaced with a desired human constant region sequences to generate a fully human antibody containing a non-IgM isotype, for example, IgG1, IgG2, IgG3 or IgG4.

Thus, in one embodiment provided herein is a method of generating an antibody that exhibits pH-dependent antigen binding properties comprising generating a non-human animal (e.g., a mouse) as described herein, immunizing a mouse with an antigen of interest, allowing a non-human animal to mount an immune response to the antigen, and selecting in the non-human animal an antigen-specific antibody that exhibits pH dependent antigen binding properties, e.g., weaker binding to the antigen at an acidic than at neutral pH.

Also provided herein are methods of making multi-specific antigen binding proteins, e.g., bispecific antigen-binding proteins. These are molecules capable of binding more than one epitope with high affinity. Advantages of the invention include the ability to select suitably high binding (e.g., affinity matured) heavy chain immunoglobulin chains each of which will associate with a single light chain. In addition, advantages of the invention include the ability to generate a multi-specific, e.g., a bispecific, antigen-binding protein that exhibits pH-dependent antigen binding.

Because of the dual nature of bispecific antibodies (i.e., may be specific for different epitopes of one polypeptide or may contain antigen-binding domains specific for more than one target polypeptide, see, e.g., Tutt et al., 1991, *J. Immunol.* 147:60-69; Kufer et al., 2004, *Trends Biotechnol.* 22:238-244), they offer many useful advantages for therapeutic application. For example, the bispecific antibodies can be used for redirected cytotoxicity (e.g., to kill tumor cells), as a vaccine adjuvant, for delivering thrombolytic agents to clots, for converting enzyme activated prodrugs at a target site (e.g., a tumor), for treating infectious diseases, targeting immune complexes to cell surface receptors, or for delivering immunotoxins to tumor cells.

The bispecific antibodies described herein can also be used in several therapeutic and non-therapeutic and/or diagnostic assay methods, such as, enzyme immunoassays, two-site immunoassays, in vitro or in vivo immunodiagnosis of various diseases (e.g., cancer), competitive binding assays, direct and indirect sandwich assays, and immunoprecipitation assays. Other uses for the bispecific antibodies will be apparent to those skilled in the art.

Several techniques for making bispecific antibody fragments from recombinant cell culture have been reported. However, synthesis and expression of bispecific binding proteins has been problematic, in part due to issues associated with identifying a suitable light chain that can associate and express with two different heavy chains, and in part due to isolation issues. In various embodiments, compositions and methods described herein provide the advantage of full length bispecific antibodies that do not require special modification(s) to maintain traditional immunoglobulin structure by increasing stability/interaction of the components. In various embodiments, such modification(s) has proven cumbersome and served as an obstacle to development of bispecific antibody technology and their potential use in treating for human disease. Thus, in various embodiments, through providing a natural immunoglobulin structure (i.e., full length) having the added property of multiple specificities, full length bispecific antibodies maintain their critical effector functions that previous bispecific fragments lacked, and further provide therapeutics that demonstrate the important pharmacokinetic parameter of a longer half-life.

Methods and compositions described herein allow for a genetically modified mouse to select, through otherwise natural processes, a suitable light chain that can associate and express with more than one heavy chain, including heavy chains that are somatically mutated (e.g., affinity matured), wherein the light chain further confers upon the antigen-binding protein its pH-dependent antigen binding property. Human heavy and light chain variable region sequences from suitable B cells of immunized mice as described herein that express affinity matured antibodies having reverse chimeric heavy chains (i.e., human variable and mouse constant) can be identified and cloned in frame in an expression vector with a suitable human constant region gene sequence (e.g., a human IgG1). Two such constructs can be prepared, wherein each construct encodes a human heavy chain variable domain that binds a different epitope. One of the human light chain variable regions (e.g., human Vκ1-39Jκ5 or human Vκ3-20Jκ1), comprising a substitution of at least one non-histidine codon with a histidine codon, can be fused in frame to a suitable human light chain constant region gene (e.g., a human κ constant gene). These three fully human heavy and light constructs can be placed in a suitable cell for expression. The cell will express two major species: a homodimeric heavy chain with the identical light chain, and a heterodimeric heavy chain with the identical light chain. To allow for a facile separation of these major species, one of the heavy chains is modified to omit a Protein A-binding determinant, resulting in a differential affinity of a homodimeric binding protein from a heterodimeric binding protein. Compositions and methods that address this issue are described in U.S. Ser. No. 12/832,838, filed 25 Jun. 2010, entitled "Readily Isolated Bispecific Antibodies with Native Immunoglobulin Format," published as US 201010331527A1, hereby incorporated by reference. Once the specie comprising heterodimeric heavy chain with an identical light chain is selected, this bi-specific antigen binding protein can be screened to confirm the retention of its pH-dependent antigen binding property.

In one aspect, an epitope-binding protein as described herein is provided, wherein human light chain and heavy chain variable region sequences are derived from animals described herein that have been immunized with an antigen comprising an epitope of interest.

In one embodiment, an epitope-binding protein is provided that comprises a first and a second polypeptide, the first polypeptide comprising, from N-terminal to C-terminal, a first epitope-binding region that selectively binds a first epitope, followed by a constant region that comprises a first $C_H3$ region of a human IgG selected from IgG1, IgG2, IgG4, and a combination thereof; and, a second polypeptide comprising, from N-terminal to C-terminal, a second epitope-binding region that selectively binds a second epitope, followed by a constant region that comprises a second $C_H3$ region of a human IgG selected from IgG1, IgG2, IgG4, and a combination thereof, wherein the second $C_H3$ region comprises a modification that reduces or eliminates binding of the second $C_H3$ domain to protein A. Various such modifications are described in, e.g., U.S. Application Publication Nos. 2010/0331527 and 2011/0195454, incorporated herein by reference.

One method for making an epitope-binding protein that binds more than one epitope and exhibits pH-dependent epitope binding property is to immunize a first mouse in accordance with the invention with an antigen that comprises a first epitope of interest, wherein the mouse comprises (1) an endogenous immunoglobulin light chain variable region locus that does not contain an endogenous mouse light chain variable region gene sequence that is capable of rearranging and forming a light chain, wherein at the endogenous mouse immunoglobulin light chain variable region locus is a single rearranged human light chain variable region operably linked to the mouse endogenous light chain constant region gene, and the rearranged human light chain variable region is selected from a human Vκ1-39Jκ5 and a human Vκ3-20Jκ1 comprising a substitution of at least one non-histidine codon with a histidine condon, and (2) the endogenous mouse $V_H$ gene segments have been replaced in whole or in part with human $V_H$ gene segments, such that immunoglobulin heavy chains made by the mouse are solely or substantially heavy chains that comprise human variable domains and mouse constant domains. When immunized, such a mouse will make a reverse chimeric antibody, comprising only one of two human light chain variable domains (e.g., one of human Vκ1-39Jκ5 or human Vκ3-20Jκ1, e.g., comprising a substitution of at least one amino acid with a histidine). Commonly, at least some of the substituted histidine residues introduced into the germline sequence will be retained in the reverse chimeric antibody. Once a B cell is identified that encodes a heavy chain variable domain that binds the epitope of interest and expresses an antibody that exhibits pH-dependent antigen binding properties, the nucleotide sequence of the heavy chain variable region (and, optionally, the light chain variable region) can be retrieved (e.g., by PCR) and cloned into an expression construct in frame with a suitable human immunoglobulin heavy chain constant region sequence. This process can be repeated to identify a second heavy chain variable domain that binds a second epitope, and a second heavy chain variable region gene sequence can be retrieved and cloned into an expression vector in frame to a second suitable human immunoglobulin heavy chain constant region sequence. The first and the second immunoglobulin constant domains encoded by the constant region gene sequence can be the same or different isotype, and one of the immunoglobulin constant domains (but not the other) can be modified as described herein or in US 2010/0331527A1, and epitope-binding protein can be expressed in a suitable cell and isolated based on its differential affinity for Protein A as compared to a homodimeric epitope-binding protein, e.g., as described in US 2010/0331527A1.

Thus, in various embodiments, following isolation of the DNA and selection of the first and second nucleic acid sequences that encode the first and second human heavy chain variable domains having the desired specificities/affinities, and a third nucleic acid sequence that encodes a human light chain domain (a germline rearranged sequence or a light chain sequence isolated from a non-human animal as described herein) and comprises a substitution of at least one non-histidine codon with a histidine codon, the three nucleic acids sequences encoding the molecules are expressed to form the bispecific antibody using recombinant techniques which are widely available in the art. Often, the expression system of choice will involve a mammalian cell expression vector and host so that the bispecific antibody is appropriately glycosylated (e.g., in the case of bispecific antibodies comprising antibody domains which are glycosylated). However, the molecules can also be produced in the prokaryotic expression systems. Normally, the host cell will be transformed with DNA encoding both the first human heavy chain variable domain, the second human heavy chain variable domain, the human light chain domain on a single vector or independent vectors. However, it is possible to express the first human heavy chain variable domain, second human heavy chain variable domain, and human light chain domain (the bispecific antibody components) in independent expression systems and couple the expressed polypeptides in vitro. In various embodiments, the human light chain domain is derived from a germline sequence but for the substitution of at least one non-histidine codon with a histidine codon, e.g., in a CDR codon. In various embodiments, the human light chain domain comprises no more than one, no more than two, no more than three, no more than four, or no more than five somatic hypermutations within the light chain variable sequence of the light chain domain. In some embodiments, the somatic hypermutations do not alter the presence of at least one histidine residue introduced into the germline sequence of the light chain variable region.

In various embodiments, the nucleic acid(s) (e.g., cDNA or genomic DNA) encoding the two heavy chains and single human light chain with a substitution of at least one non-histidine with a histidine is inserted into a replicable vector for further cloning (amplification of the DNA) and/or for expression. Many vectors are available, and generally include, but are not limited to, one or more of the following: a signal sequence, an origin of replication, one or more marker genes, an enhancer element, a promoter, and a transcription termination sequence. Each component may be selected individually or based on a host cell choice or other criteria determined experimentally. Several examples of each component are known in the art.

Expression and cloning vectors usually contain a promoter that is recognized by the host organism and is operably linked to the nucleic acid sequences that encode each or all the components of the bispecific antibody. A large number of promoters recognized by a variety of potential host cells are well known. These promoters are operably linked to bispecific antibody-encoding DNA by removing the promoter from the source DNA by restriction enzyme digestion and inserting the isolated promoter sequence into the vector.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the bispecific antibody components. Suitable expression vectors for various embodiments include those that provide for the transient expression in mammalian cells of DNA encoding the bispecific antibody. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of bispecific antibodies having desired binding specificities/affinities or the desired gel migration characteristics relative to the parental antibodies having homodimers of the first or second human heavy chain variable domains.

In various embodiments, once the DNA encoding the components of the bispecific antibody are assembled into the desired vector(s) as described above, they are introduced into a suitable host cell for expression and recovery. Transfecting host cells can be accomplished using standard techniques known in the art appropriate to the host cell selected (e.g., electroporation, nuclear microinjection, bacterial protoplast fusion with intact cells, or polycations, e.g., polybrene, polyornithine, etc.).

A host cell is chosen, in various embodiments, that best suits the expression vector containing the components and allows for the most efficient and favorable production of the bispecific antibody species. Exemplary host cells for expression include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In various embodiments, the cell is a human, monkey, ape, hamster, rat, or mouse cell. In various embodiments, the cell is eukaryotic cell selected from CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In various embodiments, the cell comprises one or more viral genes, e.g. a retinal cell that expresses a viral gene (e.g., a PER.C6™ cell).

Mammalian host cells used to produce the bispecific antibody may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. Media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™), trace elements (defined as inorganic compounds usually present at final concentrations in the micromolar range), and glucose or an equivalent energy source. Any other supplements may also be included at appropriate concentrations as known to those skilled in the art. The culture conditions, such as temperature, pH, and the like, are, in various embodiments, those previously used with the host cell selected for expression, and will be apparent to those skilled in the art.

The bispecific antibody may be recovered from the culture medium as a secreted polypeptide, although it also may be recovered from host cell lysate when directly produced without a secretory signal. If the bispecific antibody is membrane-bound, it can be released from the membrane using a suitable detergent solution (e.g., Triton-X 100).

Following isolation, a bispecific antibody comprising a two human heavy chains and a single human light chain derived from a rearranged human light chain variable region gene sequence selected from Vκ1-39Jκ5 and Vκ3-20Jκ1 sequences that comprise a substitution of at least one non-histidine codon with a histidine codon, is screened for its ability to exhibit pH dependent binding to one, preferably both of its antigens. The ability of bispecific antibodies to bind its antigens differently at neutral and acidic pH's (e.g., their ability to demonstrate decreased $t_{1/2}$ at acidic pH compared to neutral pH) can be determined by a variety of techniques available in the art and described in the following examples, e.g., BIACORE™ assay.

Additional Methods for Generating Antigen-Binding Proteins with pH-Dependent Antigen Binding Various methods of generating antigen-binding proteins with pH-dependent antigen binding properties in genetically modified non-human animals described herein are provided.

Also provided are methods of generating antigen binding proteins with pH-dependent antigen binding properties in vitro. Such methods may involve generating various components of the antigen-binding proteins in vivo in genetically modified non-human animals, and then modifying them and reassembling them in vitro outside an organism as protein complexes expressed in mammalian cell culture.

In one embodiment, the method of generating antigen-binding proteins with pH-dependent antigen binding properties utilizes an antigen-binding protein sequence, e.g., an antibody sequence, that is generated in a mouse comprising a limited repertoire of light chain variable region V and J segments, e.g., human light chain variable region V and J segments, "universal light chain" or "common light chain" mouse ("ULC" mouse), such as the mouse described in U.S. Application Publication Nos. 2011/0195454, 2012/0021409, 2012/0192300 and 2013/0045492, all incorporated herein by reference. In one embodiment, the method of generating antigen-binding proteins with pH-dependent antigen binding properties utilizes an antigen binding protein sequence that is generated in a mouse comprising a single rearranged human light chain variable region gene sequence. In one embodiment, the method utilizes an antigen binding protein generated in a mouse comprising a single rearranged human light chain variable region gene sequence selected from human Vκ1-39Jκ5 and human Vκ3-20Jκ1.

In one embodiment, the method for generating an antigen-binding protein, e.g., an antibody, with pH dependent antigen binding properties comprises selecting a first antibody that binds to an antigen of interest (e.g., binds to an antigen of interest with a desired affinity), modifying an immunoglobulin light chain nucleotide sequence of the first antibody to comprise a substitution of at least one non-histidine codon with a histidine codon, expressing an immunoglobulin heavy chain of the first antibody and the modified immunoglobulin light chain in a cell, and selecting a second antibody expressed in the cell that retains binding to the antigen of interest (e.g., retains desired affinity for the antigen of interest) at neutral pH and displays reduced binding to the antigen of interest at an acidic pH.

In one embodiment, the method for generating an antigen-binding protein, e.g., an antibody, with pH dependent antigen binding properties comprises selecting an immunoglobulin heavy chain from an antibody (e.g., obtained from a non-human animal, e.g., a mouse, e.g., a ULC mouse) that comprises an immunoglobulin light chain having a single rearranged human immunoglobulin light chain variable region sequence wherein the antibody binds to an antigen of interest (e.g., binds to an antigen of interest with a desired affinity); modifying the nucleic acid sequence of the immunoglobulin light chain such that the single rearranged human immunoglobulin light chain variable region sequence comprises a substitution of at least one non-histidine codon with a histidine codon; expressing the selected immunoglobulin heavy chain and the immunoglobulin light chain comprising the substitution of at least one amino acid with a histidine in its variable domain; and selecting an antibody that retains binding to the antigen of interest at a neutral pH (e.g., retains desired affinity to the antigen of interest) while displaying reduced binding to the antigen of interest at an acidic pH. In various embodiments, the immunoglobulin heavy chain is derived from a rearrangement of human heavy chain variable gene segments (human V, D, and J segments).

In one embodiment, the method for generating an antigen-binding protein, e.g., an antibody, with pH-dependent antigen binding properties comprises (1) immunizing a non-human animal, e.g., a mouse, comprising a single rearranged human light chain variable region gene sequence and a repertoire of unrearranged human heavy chain variable gene segments (V, D, and J segments) with an antigen of interest and allowing a mouse to mount an immune response to said antigen, (2) selecting in the non-human animal, e.g., in the mouse, an antibody that binds to the antigen of interest with a desired affinity, (3) isolating from the non-human animal, e.g., from the mouse, a nucleotide sequence of an immunoglobulin heavy chain of the antibody that binds to the antigen of interest with a desired affinity, (4) determining the nucleotide sequence of said heavy chain, (5) modifying a nucleotide sequence of an immunoglobulin light chain containing the single rearranged human immunoglobulin light chain variable region to comprise a substitution of at least one non-histidine codon with a histidine codon, (6) expressing the immunoglobulin heavy chain of the antibody that binds to the antigen of interest with desired affinity and the immunoglobulin light chain comprising the histidine modification in a cell, and (7) determining whether the antibody expressed in the cell retains binding to the antigen at a neutral pH while displaying reduced binding at an acidic pH. In one embodiment, the antibody expressed in the cell exhibits desired affinity to the antigen at neutral pH. In various embodiments, the immunoglobulin heavy chain is derived from a rearrangement of human heavy chain variable gene segments (human V, D, and J segments).

In one embodiment, the mouse comprising a single rearranged human light chain variable region gene sequence is a universal light chain or common light chain "ULC" mouse described in, e.g., U.S. Application Publication Nos. 2011/0195454, 2012/0021409, 2012/0192300 and 2013/0045492. In one embodiment, the single rearranged human light chain variable region gene sequence is selected from human Vκ1-39Jκ5 and human Vκ3-20Jκ1 sequence.

In one embodiment, the antigen of interest is selected from a soluble antigen, a cell surface antigen (e.g., a tumor antigen) and a cell surface receptor. In a specific embodiment, the cell surface receptor is an immunoglobulin receptor. In a specific embodiment, the immunoglobulin receptor is an Fc receptor.

In one embodiment, the desired affinity of an antibody for an antigen expressed as a dissociation constant ($K_D$) at a neutral pH is less than $10^{-6}$ M, e.g., less than $10^{-8}$ M, e.g., less than $10^{-9}$ M, e.g., less than $10^{-10}$ M, e.g., less than $10^{-11}$ M, e.g., less than $10^{-12}$ M.

As explained above, the ULC mice, in one embodiment, comprise a single rearranged human immunoglobulin light chain variable gene sequence, and express antibodies in response to the antigen where the affinity of antibodies to the antigen is primarily mediated through the heavy chains of their antibodies. These mice comprise a repertoire of human heavy chain variable (V, D, and J) segments, that rearrange to encode a human heavy chain variable domain of an antibody that also comprises the light chain derived from the single rearranged human light chain variable sequence. In one embodiment, upon antigen exposure, these mice utilize the diverse repertoire of human heavy chain variable (V, D, and J) segments to generate an antibody with affinity to and specificity for the antigen. Thus, upon exposure to the antigen, the nucleotide sequence of an immunoglobulin heavy chain of the antibody generated in the ULC mice may be isolated and utilized to generate a desired binding protein also comprising an immunoglobulin light chain derived from the single rearranged human immunoglobulin light chain variable region sequence (e.g., the single rearranged human immunoglobulin light chain variable region sequence with a substitution of at least one non-histidine codon with a histidine codon).

In one embodiment of the ULC mice, 90-100% of unrearranged non-human $V_H$ gene segments are replaced with at least one unrearranged human $V_H$ gene segment. In a specific embodiment, all or substantially all (e.g., 90-100%) of the endogenous non-human $V_H$ gene segments are replaced with at least one unrearranged human $V_H$ gene segment. In one embodiment, the replacement is with at least 19, at least 39, or at least 80 or 81 unrearranged human $V_H$ gene segments. In one embodiment, the replacement is with at least 12 functional unrearranged human $V_H$ gene segments, at least 25 functional unrearranged human $V_H$ gene segments, or at least 43 functional unrearranged human $V_H$ gene segments. In one embodiment, the non-human animal comprises a replacement of all non-human $D_H$ and $J_H$ segments with at least one unrearranged human $D_H$ segment and at least one unrearranged human $J_H$ segment. In one embodiment, the non-human animal comprises a replacement of all non-human $D_H$ and $J_H$ segments with all unrearranged human $D_H$ segments and all unrearranged human $J_H$ segments. Thus, the ULC mouse utilizes a diverse repertoire of human variable region gene segments (V, D, and J segments) to generate an antibody in response to the antigen of interest.

Once the heavy chain of the antibody that binds to the antigen of interest with the desired affinity is determined, the nucleotide sequence of the heavy chain is isolated and sequenced. The sequence is cloned into a vector for expression in suitable host cells, e.g., eukaryotic cells, e.g., CHO cells. In one embodiment, the sequence of a human heavy chain constant region is cloned downstream of the human heavy chain variable region sequence isolated from the mouse (e.g., from the ULC mouse).

In one embodiment, the method of generating an antigen-binding protein with pH-dependent antigen-binding properties comprises modifying a nucleotide sequence of the immunoglobulin light chain, particularly the sequence of the single rearranged human immunoglobulin light chain variable region, to comprise a substitution of at least one non-histidine codon with a histidine codon. Various techniques for modifying a nucleotide sequence are known in the art, e.g., site directed mutagenesis. In addition, a nucleotide sequence comprising the desired histidine substitution may be synthesized de novo.

In one embodiment, the substitution of at least one non-histidine codon with a histidine codon comprises a substitution resulting in expression of one, two, three, four, or more histidine residues. In one embodiment, the substitution(s) results in expression of three or four histidine residues. In one embodiment, the substitution(s) is in the immunoglobulin light chain variable region. In one embodiment, the substitution(s) is in the CDR codon, e.g., CDR1, CDR3, and/or CDR3 codon. In one embodiment, the substitution(s) is in the CDR3 codon.

In one embodiment, wherein the immunoglobulin light chain nucleic acid sequence comprises Vκ1-39Jκ5 gene sequence, and the substitution(s) is in the CDR3 codon, the substitution results in expression of a histidine at position selected from 105, 106, 108, 111, and combinations thereof. In one embodiment, the substitutions result in expression of histidines at positions 105, 106, 108, and 111. In one embodiment, the substitutions result in expression of histidines at positions 105 and 106. In one embodiment, the substitutions result in expression of histidines at positions 105 and 108. In one embodiment, the substitutions result in expression of histidines at positions 105 and 111. In one embodiment, the substitutions result in expression of histidines at positions 106 and 108. In one embodiment, the substitutions result in expression of histidines at positions 106 and 111. In one embodiment, the substitutions result in expression of histidines at positions 108 and 111. In one embodiment, the substitutions result in expression of histidines at positions 105, 106, and 108. In one embodiment, the substitutions result in expression of histidines at positions 105, 106, and 111. In one embodiment, the substitutions result in expression of histidines at positions 105, 108, and 111. In one embodiment, the substitutions result in expression of histidines at positions 106, 108, and 111. Amino acid and nucleic acid sequences of Vκ1-39Jκ5 CDR3 regions comprising various histidine substitutions are depicted in FIG. 2 and included in the sequence listing.

In one embodiment, wherein the immunoglobulin light chain nucleic acid sequence comprises Vκ3-20Jκ1 gene sequence, and the substitution(s) is in the CDR3 codon, the substitution results in expression of a histidine at position selected from 105, 106, 107, 109, and combinations thereof. In one embodiment, the substitutions result in expression of histidines at positions 105, 106, 107, and 109. In one embodiment, the substitutions result in expression of histidines at positions 105 and 106. In one embodiment, the substitutions result in expression of histidines at positions 105 and 107. In one embodiment, the substitutions result in expression of histidines at positions 105 and 109. In one embodiment, the substitutions result in expression of histidines at positions 106 and 107. In one embodiment, the substitutions result in expression of histidines at positions 106 and 109. In one embodiment, the substitutions result in expression of histidines at positions 107 and 109. In one embodiment, the substitutions result in expression of histidines at positions 105, 106, and 107. In one embodiment, the substitutions result in expression of histidines at positions 105, 106, and 109. In one embodiment, the substitutions result in expression of histidines at positions 105, 107, and 109. In one embodiment, the substitutions result in expression of histidines at positions 106, 107, and 109. Selected amino acid and nucleic acid sequences of Vκ3-20Jκ1 CDR3 regions comprising various histidine substitutions are depicted in FIG. 12 and included in the sequence listing.

Once the sequence of immunoglobulin light chain, e.g., human immunoglobulin light chain variable domain, is modified to include histidine residues at desired positions, the nucleotide sequence of the light chain is cloned into a vector for expression in suitable host cells, e.g., eukaryotic cells, e.g., CHO cells. In one embodiment, the sequence of a human light chain constant region is cloned downstream of the modified nucleotide sequence of human variable region.

In one embodiment, vectors comprising nucleotide sequence encoding modified human immunoglobulin light chain and selected human immunoglobulin heavy chain are co-expressed in a suitable host cell, e.g., eukaryotic host cell, e.g., CHO cell, to generate an antigen-binding protein. Various host cells that can be used for expression are known in the art and are mentioned throughout this specification.

An antigen-binding protein, e.g., an antibody, generated in the host cell may be secreted into cell supernatant, which is screened for proper expression and affinity for the original antigen at neutral pH. The antigen-binding protein may also be recovered from cell lysate, or, if membrane bound, released from the membrane using a suitable detergent (e.g., Triton-X). The antigen-binding protein with desired characteristics may be purified.

In one embodiment, the antigen-binding protein comprising histidine modification(s) retains the affinity to the antigen that is comparable to the affinity to the antigen of the same (original) antigen-binding protein that does not comprise histidine modification(s). In one embodiment, the affinity of the histidine-modified antigen-binding protein for the antigen of interest expressed as a dissociation constant ($K_D$) at a neutral pH is less than $10^{-6}$ M, e.g., less than $10^{-8}$ M, e.g., less than $10^{-9}$ M, e.g., less than $10^{-19}$ M, e.g., less than $10^{-11}$ M, e.g., less than $10^{-12}$ M.

In one embodiment, the antigen-binding protein, e.g., an antibody, comprising histidine modifications described herein exhibits pH dependent antigen binding properties. In one embodiment, the antigen-binding protein comprising histidine modifications possesses enhanced pH dependent properties over an equivalent antigen-binding protein without the histidine modifications (antigen-binding protein of the same amino acid sequence but for the histidine modifications). In one embodiment, the antigen-binding protein described herein retains binding to the antigen at neutral pH (e.g., retains desired affinity for the antigen at neutral pH) while displaying reduced binding at an acidic pH. In one embodiment, the antigen-binding protein, e.g., the antibody, described herein, exhibits no binding to the antigen in acidic pH, while retaining binding to the antigen at neutral pH. In one embodiment, an antigen-binding protein described herein, has a decrease in dissociative half-life ($t_{1/2}$) at an acidic pH as compared to the dissociative half-life ($t_{1/2}$) of the antigen-binding protein at a neutral pH of at least about 2-fold, at least about 3-fold, at least about 4-fold, at least about 5-fold, at least about 10-fold, at least about 15-fold, at least about 20-fold, at least about 25-fold, or at least about 30-fold. In one embodiment, an antigen-binding protein described herein has a $t_{1/2}$ at an acidic pH and 37° C. of about 2 min or less. In one embodiment, an antigen-binding protein described herein has a $t_{1/2}$ at an acidic pH and 37° C. of less than about 1 min. In one embodiment, an antigen-binding protein described herein has a $t_{1/2}$ at an acidic pH and 25° C. of about 2 min or less. In one embodiment, an antigen-binding protein described herein has a $t_{1/2}$ at an acidic pH and 25° C. of less than about 1 min.

In one embodiment, the antigen-binding protein e.g., the antibody, comprising histidine modifications described herein, exhibits increased serum half life upon administration of a therapeutic dose to a subject as compared to a serum half life upon administration of an equivalent therapeutic dose of antigen-binding protein that does not comprise histidine modifications (e.g., the original antigen-binding protein that does not comprise histidine modifications). In some embodiments, the increase in serum half life upon administration of a dose of the antigen-binding protein comprising histidine modifications described herein over a serum half life upon administration of the same dose of the antigen-binding protein not comprising histidine modifications is about 2 fold, e.g., about 5 fold, e.g., about 10 fold, e.g., about 15 fold, e.g., about 20 fold, or greater. In one embodiment, serum half-life is at least about 1 day, e.g., at least about 2 days, e.g., at least about 7 days, e.g., at least about 14 days, e.g., at least about 30 days, e.g., at least about 60 days.

In addition to the in vitro methods for generating antigen-binding proteins with pH-dependent antigen binding properties described above, also provided herein are antigen-binding proteins, e.g., antibodies, generated by said method. In addition, said method may be utilized to generate multi-specific, e.g., bispecific, antigen-binding proteins, by selecting two different human immunoglobulin heavy chains that bind to a common (universal) light chain in a mouse, determining nucleotide sequences of the heavy chains, modifying universal light chain to comprise histidine substitutions as described above, and co-expressing two human heavy chains with a single histidine-modified universal light chain in a host cell. Various steps for generating an antigen-binding protein described above may be applicable to the method of generating a bispecific antigen-binding protein. Bispecific antigen binding protein, confirmed to possess desired affinity for the antigen(s) and pH-dependent antigen binding properties may be purified. Thus, bispecific antibodies comprising two human heavy chains and a single human light chain comprising a human light chain variable domain sequence encoded by a human variable region gene, e.g., Vκ1-39Jκ5 or Vκ3-20Jκ1 variable region, gene comprising a substitution of at least one non-histidine codon with a histidine codon, is provided.

Also provided are constructs utilized in making an antigen-binding protein comprising human immunoglobulin heavy chain and human immunoglobulin light chain comprising histidine substitutions. Host cells expressing antigen-binding proteins, e.g., antibodies, described herein, are also provided.

EXAMPLES

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1

Identification of Histidine Residues in Antigen-Specific Human Light Chains

Generation of a common light chain mouse (e.g., Vκ1-39 or Vκ3-20 common light chain mouse) and antigen-specific antibodies in those mice is described in U.S. patent application Ser. Nos. 13/022,759, 13/093,156, and 13/412,936 (Publication Nos. 2011/0195454, 2012/0021409, and 2012/0192300, respectively), incorporated by reference herein in their entireties. Briefly, rearranged human germline light chain targeting vector was made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6): 652-659) to modify mouse genomic Bacterial Artificial Chromosome (BAC) clones, and genomic constructs were engineered to contain a single rearranged human germline light chain region and inserted into an endogenous κ light chain locus that was previously modified to delete the endogenous κ variable and joining gene segments. Targeted BAC DNA was then used to electroporate mouse ES cells to create modified ES cells for generating chimeric mice that express a rearranged human germline Vκ1-39Jκ5 or Vκ3-20Jκ1 region. Targeted ES cells were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1): 91-99). VELOCIMICE® independently bearing an engineered human germline Vκ1-39Jκ6 or Vκ3-20Jκ1 light chain region were identified by genotyping using a modification of allele assay (Valenzuela et al., supra) that detects the presence of the unique rearranged human germline light chain region.

Mice bearing an engineered human germline light chain locus (ULC mice) were bred with mice that contain a replacement of the endogenous mouse heavy chain variable gene locus with the human heavy chain variable gene locus (see U.S. Pat. No. 6,596,541; the VELOCIMMUNE® mouse, Regeneron Pharmaceuticals, Inc.).

VELOCIMMUNE® mouse containing a single rearranged human germline light chain region is challenged with an antigen of interest and antibodies comprising a universal light chain (e.g., Vκ1-39Jκ5) are isolated and sequenced. Amino acid sequences of selected light chains (A-K, corresponding to SEQ ID NOs: 82-92, respectively) from antigen-specific human antibodies generated in a common Vκ1-39Jκ5 light chain mouse were aligned. Histidine mutations in the CDRs of human Vκ1-39-derived light chains for a selected number of antigen-specific human antibodies were identified (FIG. 1). The partial amino acid sequence of germline Vκ1-39Jκ5 variable domain is shown above the alignments and set forth in SEQ ID NO:1, the complete variable domain amino acid sequence is set forth in SEQ ID NO:80.

Example 2

Engineering and Characterization of Histidine-Substituted Human Universal Light Chain Antibodies Example 2.1

Engineering of Histidine Residues into a Germline Human Rearranged Light Chain

Histidine residues were engineered into a rearranged human Vκ1-39Jκ5 light chain using site directed mutagenesis primers specifically designed to introduce engineered histidine residues at Q105, Q106, Y108, and P111 positions of the human Vκ1-39Jκ5 light chain. Site directed mutagenesis was performed using molecular techniques known in the art (e.g., QuikChange II XL Site Directed Mutagenesis Kit, Agilent Technologies). Locations of the engineered residues in the CDR3 are shown in FIG. 2, the nucleic acid sequences of histidine-substituted CDR3's depicted in FIG. 2 are set forth in SEQ ID NOs: 4, 6, 8, 10, 12, 14, 16, 18, 20, 22, 24, 26, 28, 30, and 32 (corresponding amino acid sequences are set forth in SEQ ID NOs: 5, 7, 9, 11, 13, 15, 17, 19, 21, 23, 25, 27, 29, 31, and 33). The nucleic acid and amino acid sequences of germline rearranged Vκ1-39Jκ5 CDR3 are set forth in SEQ ID NOs: 2 and 3, respectively.

Example 2.2

Construction and Expression of Histidine Engineered Light Chains

Human Vκ1-39-derived light chains containing germline engineered histidine residues made according to Example 2 were constructed and paired with various human heavy chains (labeled 1-5), specific for a human cell surface receptor, to analyze expression in CHO cells. The five human heavy chains specific for a human cell surface receptor that were paired with histidine-substituted Vκ1-39-derived light chains were obtained from mice that have a single rearranged human light chain (a human Vκ1-39/Jκ5 rearranged light chain; see US2011/0195454A1).

Enzyme-Linked Immunosorbent Assay (ELISA):

Antibody secretion from CHO cells was detected using an Fc ELISA, for light chains with indicated histidine modifications with five different heavy chains. The light and heavy chain sequences (but for the modifications) were generated in mice that have a single rearranged human light chain (e.g., a human Vκ1-39/Jκ5 rearranged light chain; see US2011/0195454A1). Capture antibody was goat anti-human IgG and detection antibody was goat anti-human (Fc gamma-specific)-HRP. The results are shown in FIG. 3. ULC+heavy: specific heavy chain and unmodified human Vκ1-39-derived light chain. As shown in FIG. 3, expression was detected in about all mutants.

Protein Immunoblot.

Figure 4:
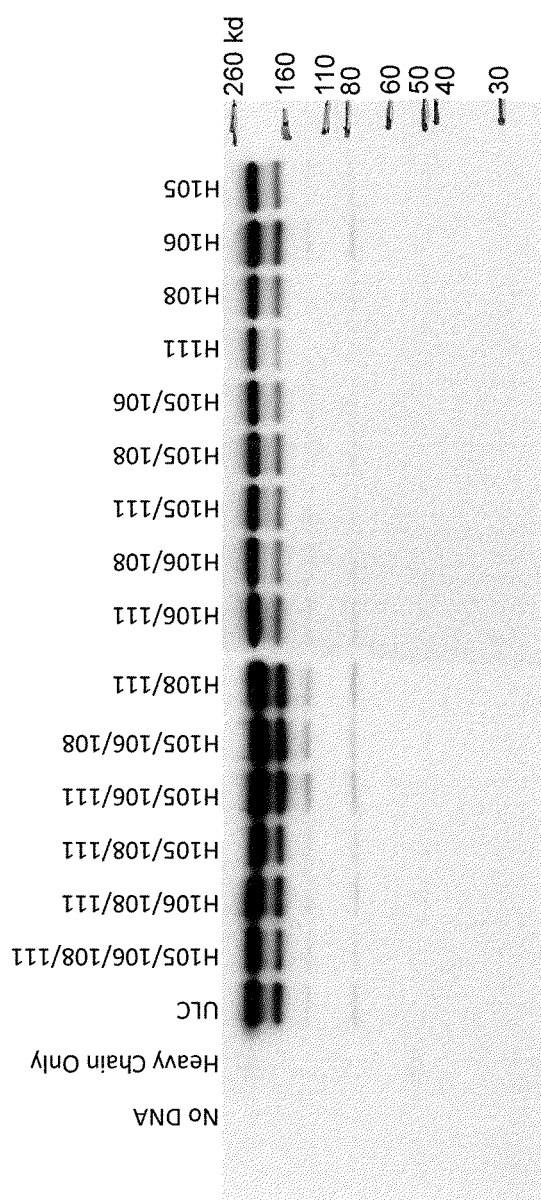
FIG. 4 is a western blot showing expression of selected antigen-specific human antibodies containing histidine engineered light chains in CHO cell supernatants.

Expression in supernatants of CHO cells of paired antigen-specific heavy chains with histidine engineered light chains was further analyzed by western blot. Samples were run on a 4-12% tris-glycine gel. Results using a selected heavy chain (heavy chain 3) are shown in FIG. 4. ULC refers to a rearranged human Vκ1-39-derived light chain (as described above).

Example 2.3

Determination of Binding Affinity of Histidine Engineered Light Chains

Equilibrium dissociation constants ($K_D$), dissociative half-lives ($t_{1/2}$), and other kinetic parameters for selected antibody supernatants were determined by SPR (Surface Plasmon Resonance) using a BIACORE™ T200 instrument (GE Healthcare). Kinetics were measured at pH 7.4 and at pH 5.75. Results are shown in FIGS. 5A-5E.

Numerical values for the kinetic binding properties (e.g., $k_a$, $k_d$, $K_D$, $t_{1/2}$, etc.) of antibodies binding to immunogen at neutral pH (pH 7.4) and at acidic pH (pH 5.75) were obtained using a real-time surface plasmon resonance biosensor (Biacore T200.) A Biacore CM5 sensor chip was derivatized with a mouse anti-human Fc antibody to capture antibodies from the supernatant. A single concentration (50 nM) of immunogen was then injected over the antibody-captured surface at a flow rate of 30 μl/min. Antibody-antigen association was monitored for 2.5 minutes and then the dissociation of antigen from the captured antibody was monitored for 8 minutes. Kinetic association (ka) and dissociation (kd) rate constants were determined by processing and fitting the data to a 1:1 binding with a mass transport model using Biacore T200 Evaluation software version 1.0. Equilibrium dissociation constants ($K_D$) and dissociative half-lives ($t_{1/2}$) were calculated from the kinetic rate constants as: $K_D$ (M)=$k_d/k_a$; and $t_{1/2}$ (min)=(ln 2/(60*$k_d$).

As shown in FIG. 5, in a binding assay of antibody to a cell surface receptor, two out of five antibodies with histidine-modified common light chains (histidine modified CDR3's of Vκ1-39/Jκ5 light chains) that were paired with the antigen-specific human heavy chains, exhibited binding to the antigen (e.g., to a cell surface receptor) with different affinities at pH 7.4 and pH 5.75. Antibodies with histidine modifications that retain binding at pH 7.4, but that exhibit a low binding or no detectable binding at pH 5.75, are desirable. Antibodies with histidine modification that exhibit reduced $t_{1/2}$ at pH 5.75 as compared to pH 7.4 are desirable.

Antigen binding data for three antibodies comprising histidine-modified common light chains and three antigen-specific heavy chains (labeled 2, 3, and 6) at different pHs is summarized further in FIG. 6. These antibodies exhibited significant drop in antigen binding at pH 5.75 in comparison to pH 7.4, as demonstrated, e.g., by reduction in $t_{1/2}$ or no binding detected at pH 5.75.

Example 3

Engineering and Characterization of Genetically Modified Mouse Comprising a Histidine-Substituted Vκ1-39Jκ5 Universal Light Chain Example 3.1

Constructing of Targeting Vector for Engineering Histidine Residues in a Rearranged Human Light Chain Variable Region A genetically modified mouse containing a rearranged human light chain gene having histidine residues engineered into a CDR region of the human light chain is made using targeting vectors made by standard molecular cloning techniques known in the art.

Briefly, various rearranged human germline light chain targeting vectors are made using VELOCIGENE® technology (see, e.g., U.S. Pat. No. 6,586,251 and Valenzuela et al., (2003) High-throughput engineering of the mouse genome coupled with high-resolution expression analysis, Nature Biotech. 21(6):652-659) to modify mouse genomic Bacterial Artificial Chromosome (BAC) DNA to contain a single rearranged human germline light chain region and inserted into an endogenous κ light chain locus that was previously modified to delete the endogenous κ variable and joining gene segments. The rearranged human germline light chain region is modified at one or more nucleotide positions within the sequence of the light chain to encode histidine residues that are not normally present at the respective locations of the germline sequence. The targeting vectors are electroporated into mouse embryonic stem (ES) cells and confirmed using a quantitative PCR assay (e.g., TAQMAN™).

Figure 8A:
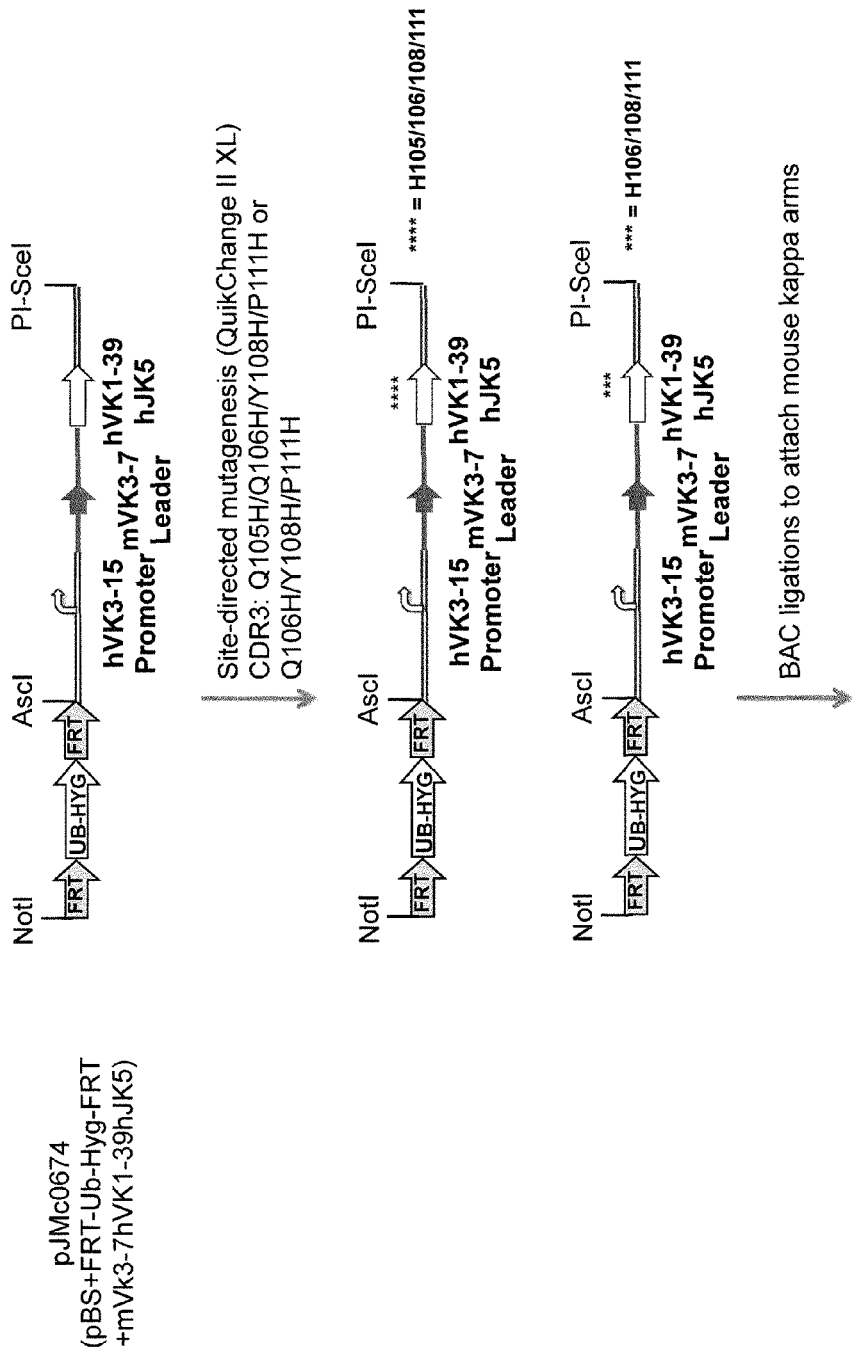
FIGS. 8A-8B show a general strategy for construction of targeting vectors for engineering of histidine residues into a rearranged human light chain variable region sequence derived from Vκ1-39/Jκ5 variable region for making a genetically modified mouse that expresses antibodies containing the modified human light chain.
Figure 8B:
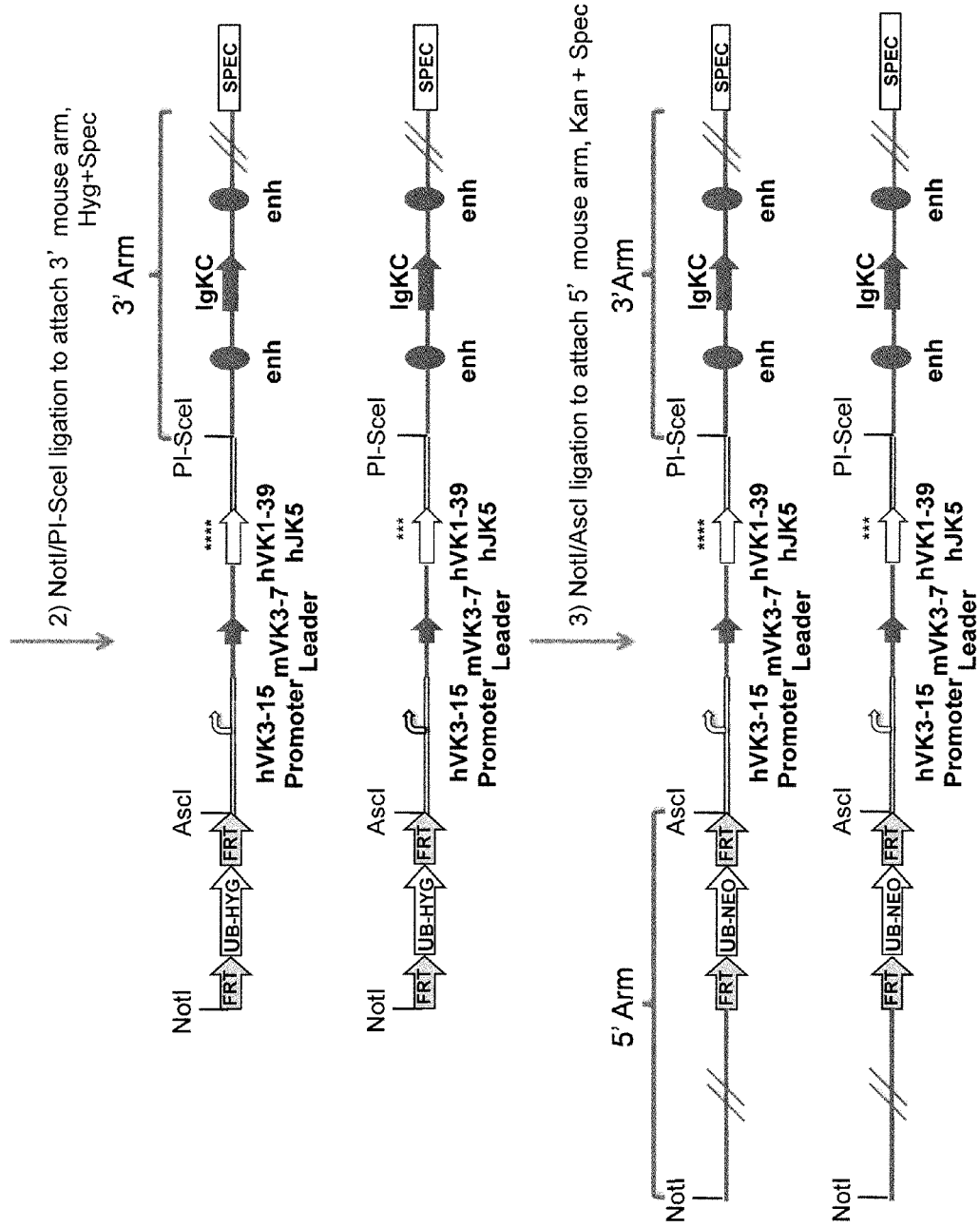

Specifically, a strategy for constructing these targeting vectors is shown in FIGS. 8A-8F. A plasmid used for generating a targeting vector for common (universal) light chain mouse ("ULC mouse," described in, e.g., US2011/0195454A1), containing pBS+FRT-Ub-Hyg-FRT+mouse Vκ3-7 leader+human Vκ1-39Jκ5 was modified by site directed mutagenesis (QuickChange II XL Kit) to replace Q105, Q106, Y108 and P111 or Q106, Y108 and P111 with histidine residues in the CDR3 region using site-directed mutagenesis primers shown in FIG. 7 (See FIG. 8A for this engineering step). Resultant vectors (H105/106/108/111 and H106/108/111) were modified further and ligated into a vector comprising mouse Igκ constant region, mouse enhancers, a mouse 3' homology arm and a SPEC cassette (FIG. 8B). Further modification involved ligation into a vector carrying 5' mouse arm and comprising Frt-Ub-NEO-Frt cassette (FIG. 8B). Resultant targeting vectors were electroporated into ES cells comprising deletion of the mouse Igκ variable locus (comprising κ variable and joining gene segments) (FIGS. 8C-8F).

Positive ES cell clones were confirmed by using a modification of allele assay (Valenzuela et al.) using probes specific for the engineered Vκ1-39Jκ5 light chain region inserted into the endogenous κ light chain locus. Primers and probes used in the assay are shown in Table 1 below and set forth in the Sequence Listing; the locations of the probes are depicted in FIGS. 8C-8F.

TABLE 1

Primers and Probes Used for ES Cell Screening

| Probe Name | Assay | Probe Sequence | 5' Primer | 3' Primer |
|---|---|---|---|---|
| Neo | GOA | TGGGCACAACAGACAATCGGCTG (SEQ ID NO: 38) | GGTGGAGAGGCTATTCGGC (SEQ ID NO: 39) | GAACACGGCGGCATCAG (SEQ ID NO: 40) |
| ULC-m1 | GOA | CCATTATGATGCTCCATGCCTCTCTGTTC (SEQ ID NO: 41) | AGGTGAGGGTACAGATAAGTGTTATGAG (SEQ ID NO: 42) | TGACAAATGCCCTAATTATAGTGATCA (SEQ ID NO: 43) |
| 1633h2 (Vκ1-39Jκ5-specific) | GOA | ATCAGCAGAAACCAGGGAAAGCCCCT (SEQ ID NO: 44) | GGGCAAGTCAGAGCATTAGCA (SEQ ID NO: 45) | TGCAAACTGGATGCAGCATAG (SEQ ID NO: 46) |
| mIgKd2 | Retention | GGCCACATTCCATGGGTTC (SEQ ID NO: 47) | GCAAACAAAAACCACTGGCC (SEQ ID NO: 48) | CTGTTCCTCTAAAACTGGACTCCACAGTAAATGGAAA (SEQ ID NO: 49) |
| mIgKp15 | Retention | GGGCACTGGATACGATGTATGG (SEQ ID NO: 50) | CACAGCTTGTGCAGCCTCC (SEQ ID NO: 51) | AGAAGAAGCCTGTACTACAGCATCCGTTTTACAGTCA (SEQ ID NO: 52) |

Figure 8C:
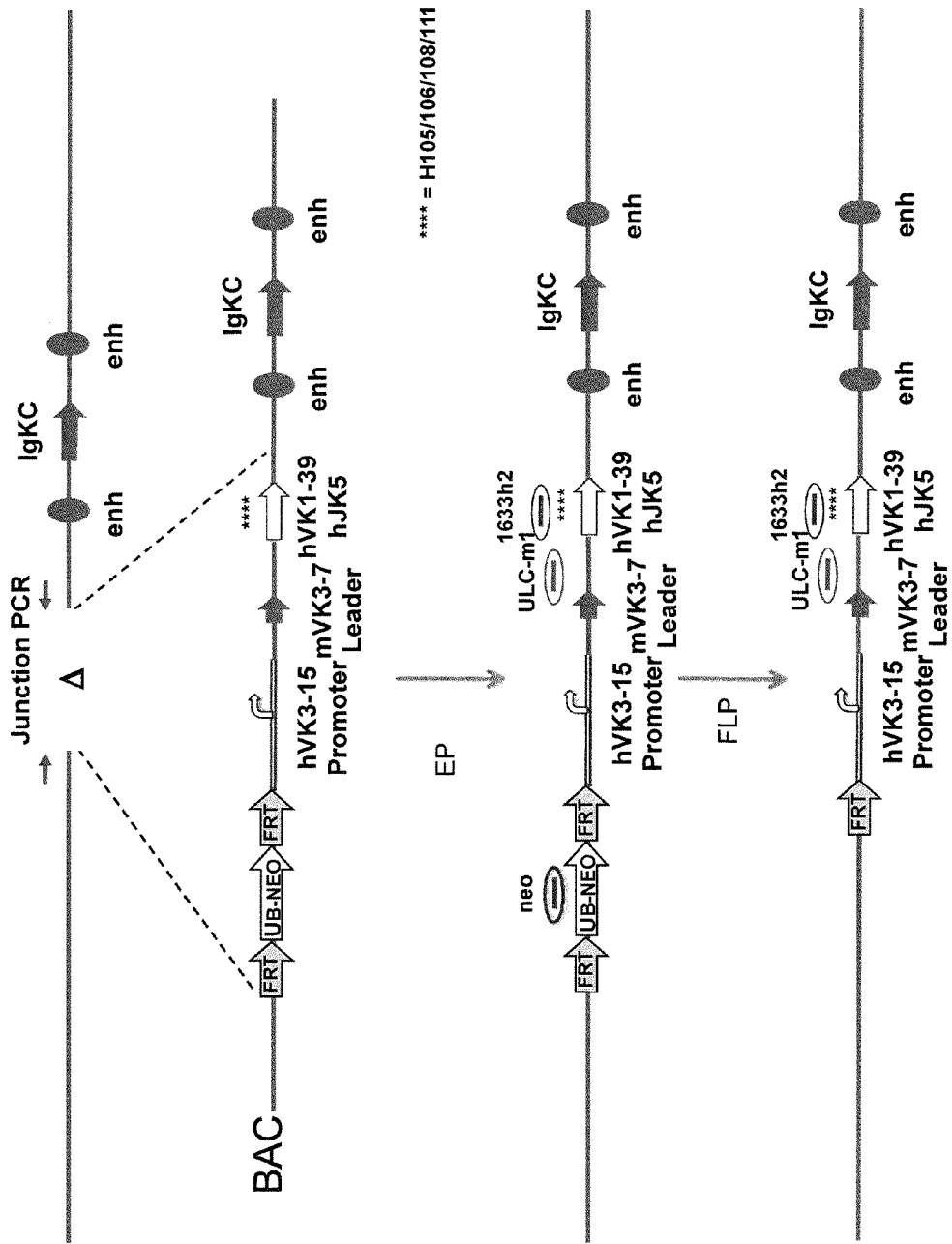
Figure 8D:
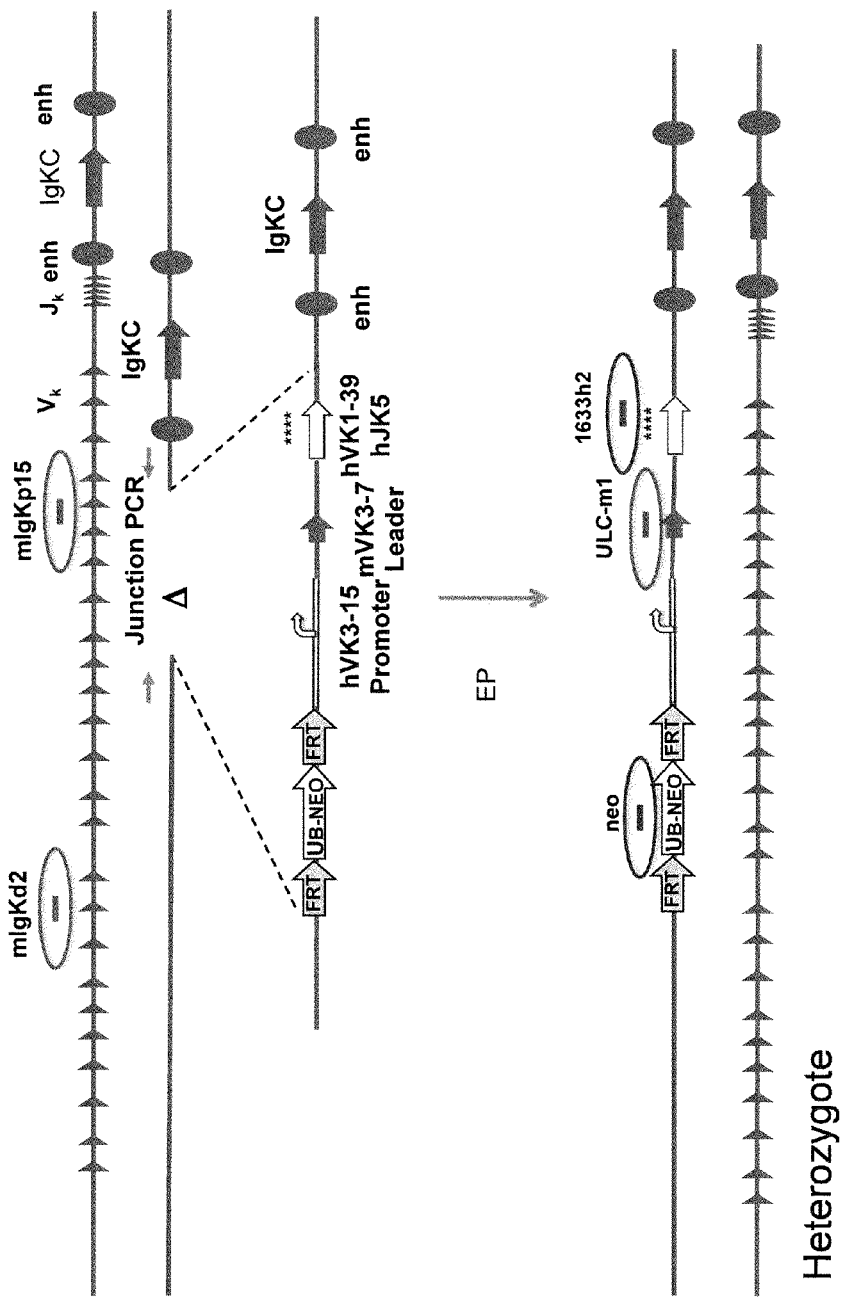
Figure 8E:
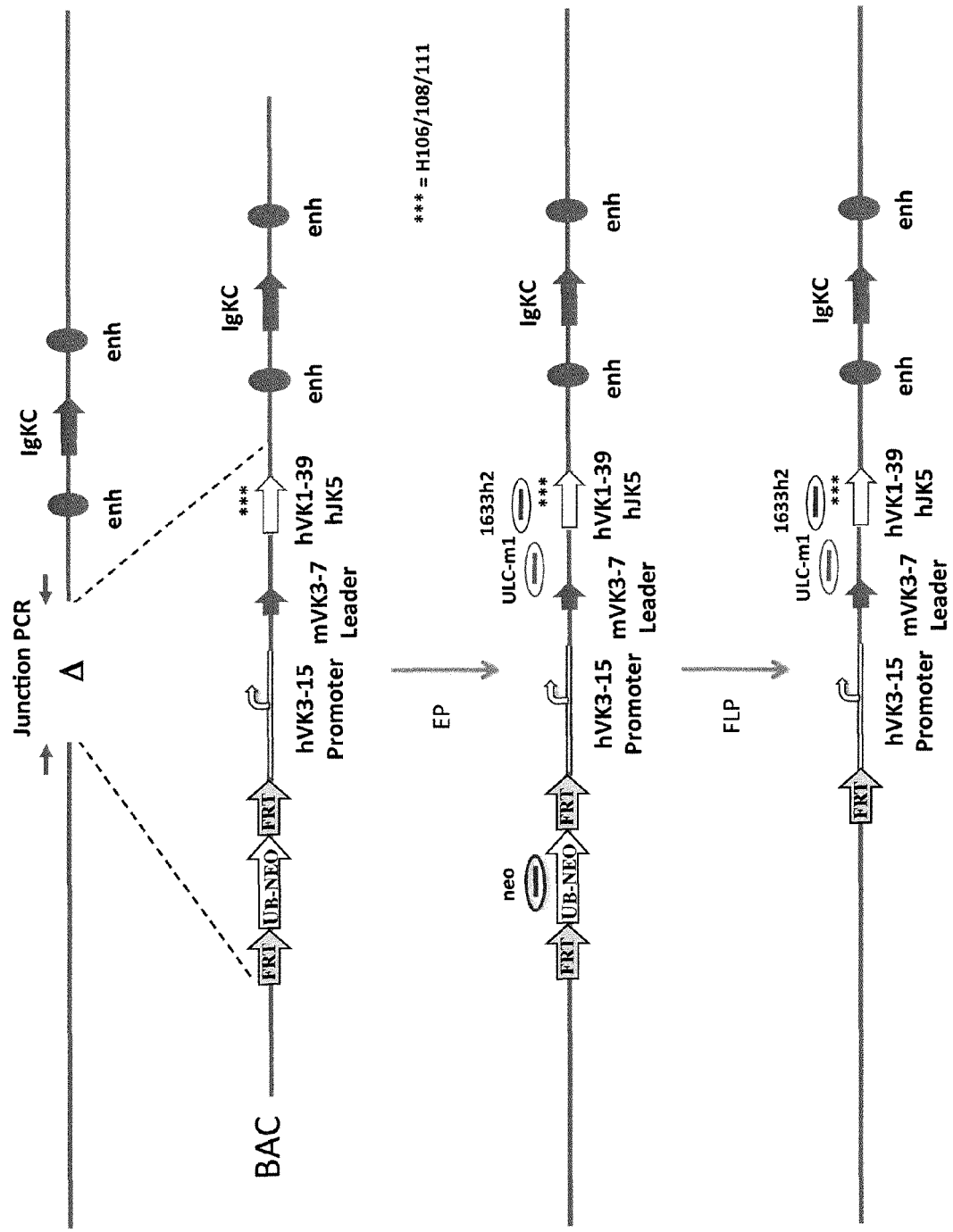
FIGS. 8E-8F show introduction of the targeting vector for ULC-H106/108/111 substitutions into ES cells and generation of heterozygous mice from the same. The diagrams are not presented to scale. Unless indicated otherwise, filled shapes and solid lines represent mouse sequence, empty shapes and double lines represent human sequence.
Figure 8F:
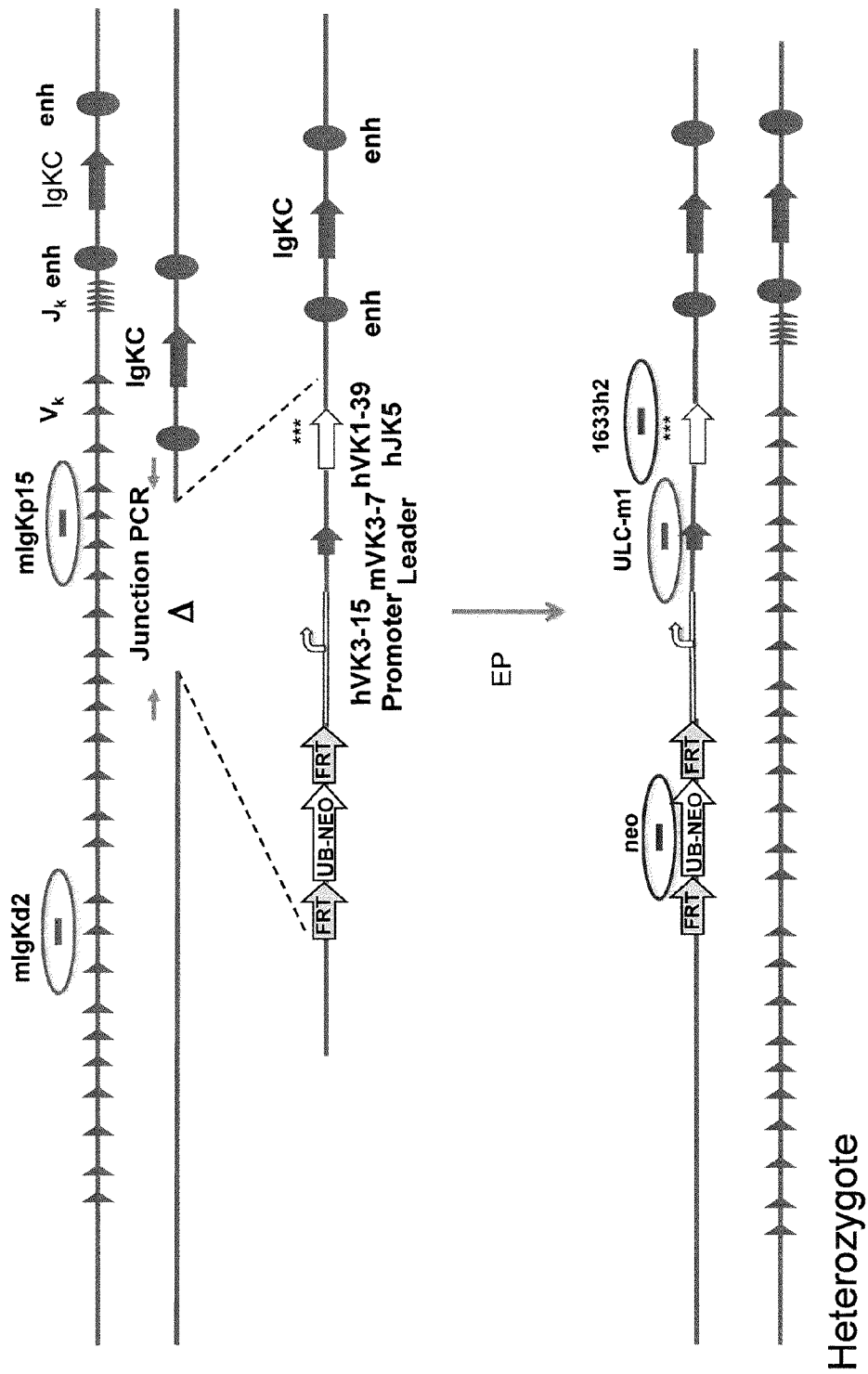

The NEO selection cassette introduced by the targeting constructs was deleted by transfecting ES cells with a plasmid that expresses FLP (FIGS. 8C and 8E). Optionally, the neomycin cassette may be removed by breeding to mice that express FLP recombinase (e.g., U.S. Pat. No. 6,774,279). Optionally, the neomycin cassette is retained in the mice.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99. VELOCIMICE® independently bearing an engineered human light chain gene that contains histidine residues mutated into one or more positions along the sequence were made from the targeted ES cells described above.

Pups were genotyped and pups heterozygous for the engineered histidine-modified human light chain were selected for characterizing expression of the light chain and binding capabilities of the expressed antibodies. Primers and probes for genotyping of mice specifically comprising a universal light chain gene with either three (H106/108/111; "1930") or four (H105/105/108/111; "1927") histidine modifications are listed in Table 2 below and set forth in the Sequence Listing. Mice containing histidine modification in their universal light chains are referred herein as "HULC" mice (histidine universal light chain mice).

Example 3.2

Analysis of Immune Response to Antigen in Mice with Histidine-Substituted Universal Light Chains Cell surface receptor ("Antigen A") was used as the immunogen to immunize mice that were either heterozygous for expression of a pre-arranged human kappa light chain utilizing Vk1-39 and Jk5 that has 4 histidine substitutions in CDR3 (hereinafter "HULC 1927") or heterozygous for expression of a pre-arranged human kappa light chain utilizing Vk1-39 and Jk5 that has 3 histidine substitutions in CDR3 (hereinafter "HULC1930"), or homozygous WT mice. Pre-immune serum was collected from the mice prior to the initiation of immunization. The immunogen was administered at 2.35 µg of protein for the initial priming immunization mixed with 10 µg of CpG oligonucleotide as an adjuvant (Invivogen) in a volume of 25 µl via footpad (f.p.). Subsequently, mice were boosted via the same route with 2.35 µg of Antigen A along with 10 µg of CpG and 25 µg of Adju-Phos (Brenntag) as adjuvants on days 3, 6, 11, 13, 17, 20 for a total of 6 boosts. The mice were bled on days 15 and 22 after the $4^{th}$ and $6^{th}$ boost, respectively. Their antiserum was assayed for antibody titers to Antigen A.

Antibody serum titers against immunogen were determined by a standard ELISA. To perform the ELISA, 96-well microtiter plates (Thermo Scientific) were coated at 2 µg/ml with Antigen A in phosphate-buffered saline (PBS, Irvine

TABLE 2

Primers and Probes Used for Genotyping

| Probe Name | Assay | Probe Sequence | 5' Primer | 3' Primer |
|---|---|---|---|---|
| 1927jxn3 | GOA 1927 (4 His) mouse-specific | ACCATAGTCACAGTACCCA (SEQ ID NO: 53) | AGCAGTCTGCAACCTGAAGATTT (SEQ ID NO: 54) | CCCTTGGCCGAAGGTGAT (SEQ ID NO: 55) |
| 1930jxn3 | GOA 1930 (3 His) mouse-specific | ATAGTCACAGTACCCATCC (SEQ ID NO: 56) | AGTCTGCAACCTGAAGATTTTGC (SEQ ID NO: 57) | CCCTTGGCCGAAGGTGAT (SEQ ID NO: 58) |

Scientific) overnight at 4° C. The next day, plates were washed with phosphate-buffered saline containing 0.05% Tween 20 (PBS-T, Sigma-Aldrich) four times using a plate washer (Molecular Devices). Plates were then blocked with 250 μl of 0.5% bovine serum albumin (BSA, Sigma-Aldrich) in PBS and incubated for 1 hour at room temperature. The plates were then washed four times with PBS-T. Sera from immunized mice and pre-immune sera were serially diluted three-fold in 0.5% BSA-PBS starting at 1:300 or 1:1000, added to the blocked plates in duplicate, and then incubated for 1 hour at room temperature. The last two wells were left blank to be used as a secondary antibody control (background control). The plates were again washed four times with PBS-T in a plate washer. Goat anti-mouse IgG-Fc-Horse Radish Peroxidase (HRP) conjugated secondary antibody (Jackson Immunoresearch) was then added to the plates at 1:5000/1:10,000 dilution and incubated for 1 hour at room temperature. Plates were then washed eight times with PBS-T and developed using $TMB/H_2O_2$ as substrate. The substrate was incubated for 20 min and the reaction was stopped with 2 N sulfuric acid ($H_2SO_4$, VWR, cat# BDH3500-1) or 1 N phosphoric acid (JT Baker, Cat#7664-38-2). Plates were read on a spectrophotometer (Victor, Perkin Elmer) at 450 nm. Antibody titers were computed using Graphpad PRISM software.

Figure 9:
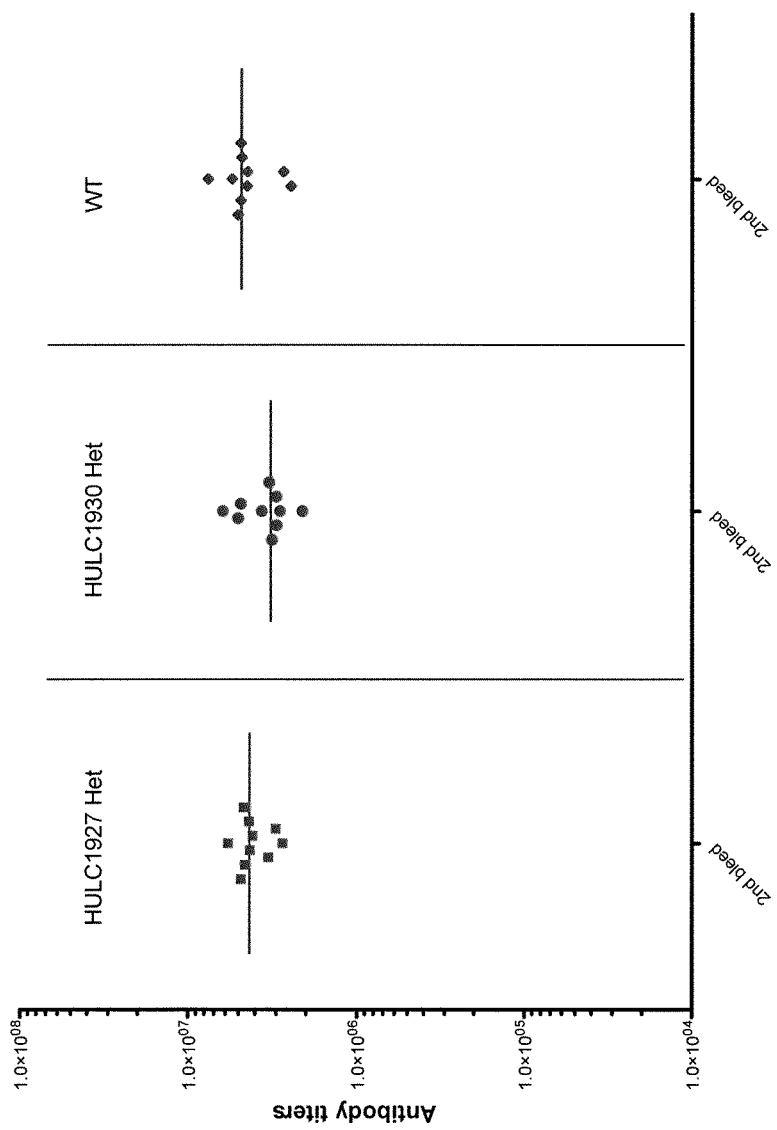
FIG. 9 shows antiserum titers against immunogen from mice heterozygous for histidine universal light chain (HULC) (with 4 His substitutions—HULC 1927 mice; with 3 His substitutions—HULC 1930 mice) and wild type animals in a second bleed.

The immune response induced in mice to the injected immunogen is represented as antibody titers, which is defined as the reciprocal of the highest serum dilution at which antigen binding absorbance is two-fold higher over background. Therefore, the higher the number, the greater the humoral immune response to the immunogen. Antibody titers induced to the immunogen were very high in both strains of HULC mice and in the WT mice, with no significant differences observed among the strains (FIG. 9).

Example 3.3

Generation of pH-Sensitive Monoclonal Antibodies

When a desired immune response to the immunogen was achieved in both strains of HULC mice and in the WT mice, splenocytes from each mouse strain were harvested and fused with mouse myeloma cells to generate hybridoma cells, which were allowed to grow in 96-well plates. After 10 days of growth, supernatants from each hybridoma cell-containing well were screened via immunogen-specific ELISA to identify positive antigen binding samples. For the ELISA, 96 well micro-titer plates were coated with 1 ug/mL of an anti-myc polyclonal antibody (Novus Biologicals, #NB600-34) overnight at 4° C. to immobilize the myc-tagged antigen, followed by blocking with a solution of 0.5% (w/v) BSA in PBS. The plates were washed, the antigen solutions were added to the plates at a concentration of 1 μg/mL and allowed to bind to the coated plate for 1 hour at room temperature. Subsequently, supernatants from hybridoma cells were added to the wells at 1:50 dilution and allowed to bind for 1 hour at room temperature. The plate bound antibodies were detected using an anti-mouse IgG polyclonal antibody conjugated with HRP (Jackson Immunoresearch, #115-035-164). TMB substrates were added to the plates (BD Biosciences, #51-2606KC/51-2607KC) and colorimetric signals were developed according to manufacturer recommended protocol. The absorbance was recorded at 450 nm on a Victor Wallac plate reader. Antigen positive samples defined as having an OD equal to or greater than 0.5 (with the baseline having OD of about 0.1) were subject to affinity screening using a real-time surface plasmon resonance biosensor (Biacore 4000).

Figure 10:
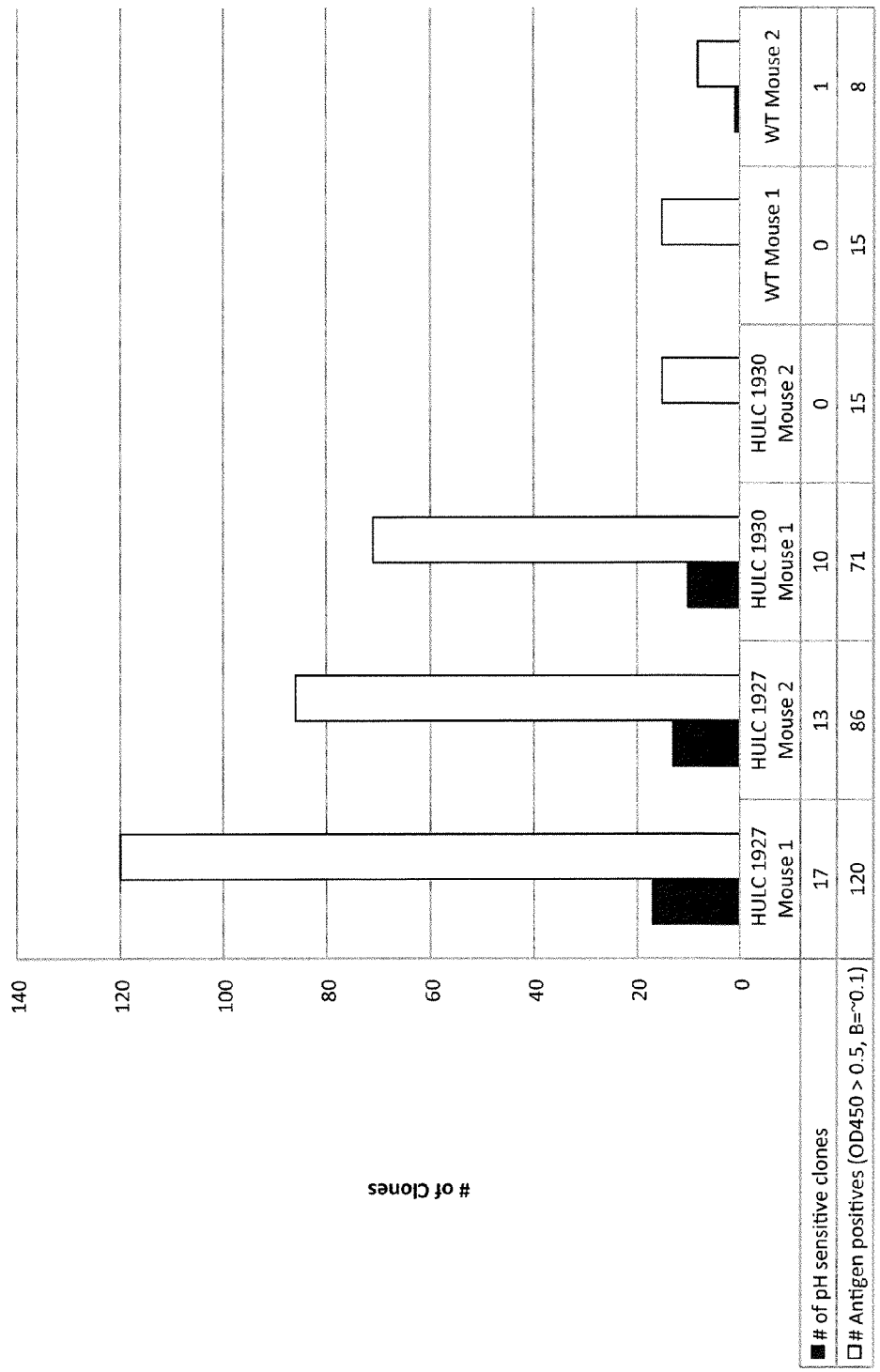
FIG. 10 is a comparison of the number of total antigen positive clones and the number of antigen positive clones displaying pH sensitive antigen binding obtained from hybridoma fusions from heterozygous HULC (1927 vs 1930) and WT mice. Figure includes data for two mice for each mouse type ("mouse 1" and "mouse 2").

Kinetic binding parameters (e.g., $k_a$, $k_d$, $K_D$, $t_{1/2}$, etc.) for antibody binding to the immunogen at neutral pH (pH 7.4) and at acidic pH (pH 6.0) were recorded. A Biacore CM4 sensor chip was derivatized with a polyclonal goat anti-mouse Fc antibody to capture antibodies from the supernatant. A single concentration (100 nM) of immunogen was then injected over the antibody-captured surface at a flow rate of 30 μl/min. Antibody-antigen association was monitored for 1.5 minutes and then the dissociation of antigen from the captured antibody was monitored for 2.5 minutes. Kinetic association ($k_a$) and dissociation ($k_d$) rate constants were determined by processing and fitting the data to a 1:1 binding with a mass transport model using Biacore 4000 Evaluation software version 1.0. Equilibrium dissociation constants ($K_D$) and dissociative half-lives ($t_{1/2}$) were calculated from the kinetic rate constants as: $K_D$ (M)=$k_d/k_a$; and $t_{1/2}$ (min)=ln 2/(60*$k_d$). A set of samples that displayed decreased binding at pH 6.0 as compared to that at pH 7.4 (pH sensitive) as well as a set of control samples that displayed no significant rate changes between the pH 7.4 and pH 6.0 (pH insensitive controls) were selected to be produced clonally. FIG. 10 depicts comparison of the number of total antigen positives and the number of antigen positives displaying pH-sensitive antigen binding from HULC and WT mice.

Among the antigen positives, 18 and 7 clones isolated from two heterozygous HULC1927 mice and two HULC1930 respectively, and 1 clone from the WT mouse, were made monoclonal. Supernatants of the monoclonal hybridomas were subject to neutral and low pH antigen dissociation rate (off-rate) analysis and cell pellets were used for light chain variable domain DNA sequencing.

Example 3.4

Sequencing and Somatic Hypermutations in CDR3 Region of Vκ1-39Jκ5-based Histidine Universal Light Chain Mice Cell pellets from monoclonal hybridomas from HULC and WT mice were used for light chain variable domain DNA sequencing. From the 26 clones made monoclonal (see Example 3.3 above) and subjected to sequencing, 15 were confirmed as using either a HULC or WT mouse light chain (MM and NN, see Table 4). 14 clones were derived from HULC heterozygous mice (1927 or 1930 mice) and 1 was derived from a WT mouse (OO, see Table 4).

From the 14 antigen positive samples derived from HULC heterozygous mice, 12 of the monoclonal antibodies utilized their corresponding HULC light chain, while 2 utilized a WT mouse light chain. All but one of the HULC utilizing antibodies retained all of the introduced histidine mutations as shown in Table 3 (italicized antibody). Sequencing of clone AA produced 2 different HULC sequences, which is reflected by two entries in Table 3.

TABLE 3

Number of conserved histidine insertions and somatic hypermutations in light chain sequences from clones utilizing the HULC light chain

| | | Light Chain Sequences from mice utilizing HULC | | |
|---|---|---|---|---|
| Clone Name | Mouse Strain | # Conserved His Mutations in CDR3 | # Somatic Hypermutations in Framework | # Somatic Hypermutations in CDRs |
| AA (Sequence 1) | 1927 | 4 | 3 | 0 |
| AA (Sequence 2) | 1927 | 4 | 1 | 1 |

TABLE 3-continued

Number of conserved histidine insertions and somatic hypermutations in light chain sequences from clones utilizing the HULC light chain

| | | Light Chain Sequences from mice utilizing HULC | | |
|---|---|---|---|---|
| Clone Name | Mouse Strain | # Conserved His Mutations in CDR3 | # Somatic Hypermutations in Framework | # Somatic Hypermutations in CDRs |
| BB | 1927 | 4 | 3 | 3 |
| CC | 1927 | 4 | 0 | 0 |
| DD | 1927 | 3 | 1 | 1 |
| EE | 1927 | 4 | 2 | 2 |
| FF | 1927 | 4 | 0 | 1 |
| GG | 1927 | 4 | 1 | 1 |
| HH | 1927 | 4 | 2 | 0 |
| II | 1930 | 3 | 1 | 1 |
| JJ | 1930 | 3 | 4 | 5 |
| KK | 1930 | 3 | 1 | 2 |
| LL | 1930 | 3 | 1 | 0 |

Example 3.5 pH-Dependent Binding of Monoclonal Antibodies Generated in Vκ1-39Jκ5-Based Histidine Universal Light Chain Mice In order to further assess the pH-dependent binding characteristics of the monoclonal antibodies isolated from HULC and WT mice, binding experiments were carried out in which the antibody/antigen association phase was observed at neutral pH and the antibody/antigen dissociation phase was observed at either neutral or acidic pHs.

Figure 11A:
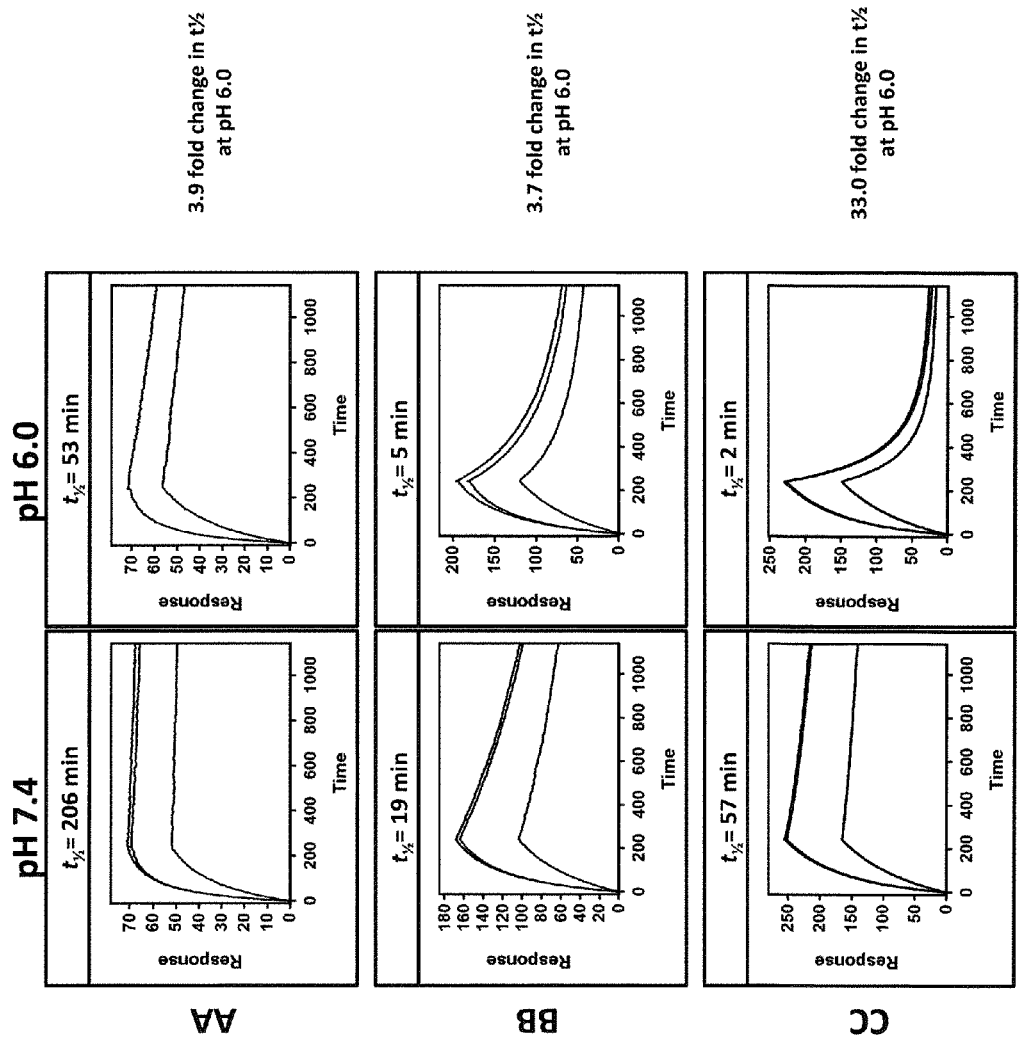
FIGS. 11A-11C show sensorgrams from surface plasmon resonance binding experiments in which monoclonal antibodies (AA, BB, CC, DD, HH, GG, NN, and OO) from either heterozygous HULC or WT mice were allowed to associate with the immunogen at neutral pH (pH 7.4) followed by a shift to a buffer with pH of either 7.4 or 6.0 for the dissociation phase. The individual lines in each graph represent the binding responses at different concentrations of the respective antibodies. All experiments were carried out at 25° C. Dissociative half-life values (t½) are noted above the respective sensorgrams, and fold change in t½ is included to the right of each sensorgram. Antibodies AA, BB, CC, DD, HH, and GG were from heterozygous HULC 1927 mice using His-substituted light chain, NN is from heterozygous HULC 1927 mouse using WT light chain, and OO is from a WT mouse (See Table 4 for clarification).
Figure 11B:
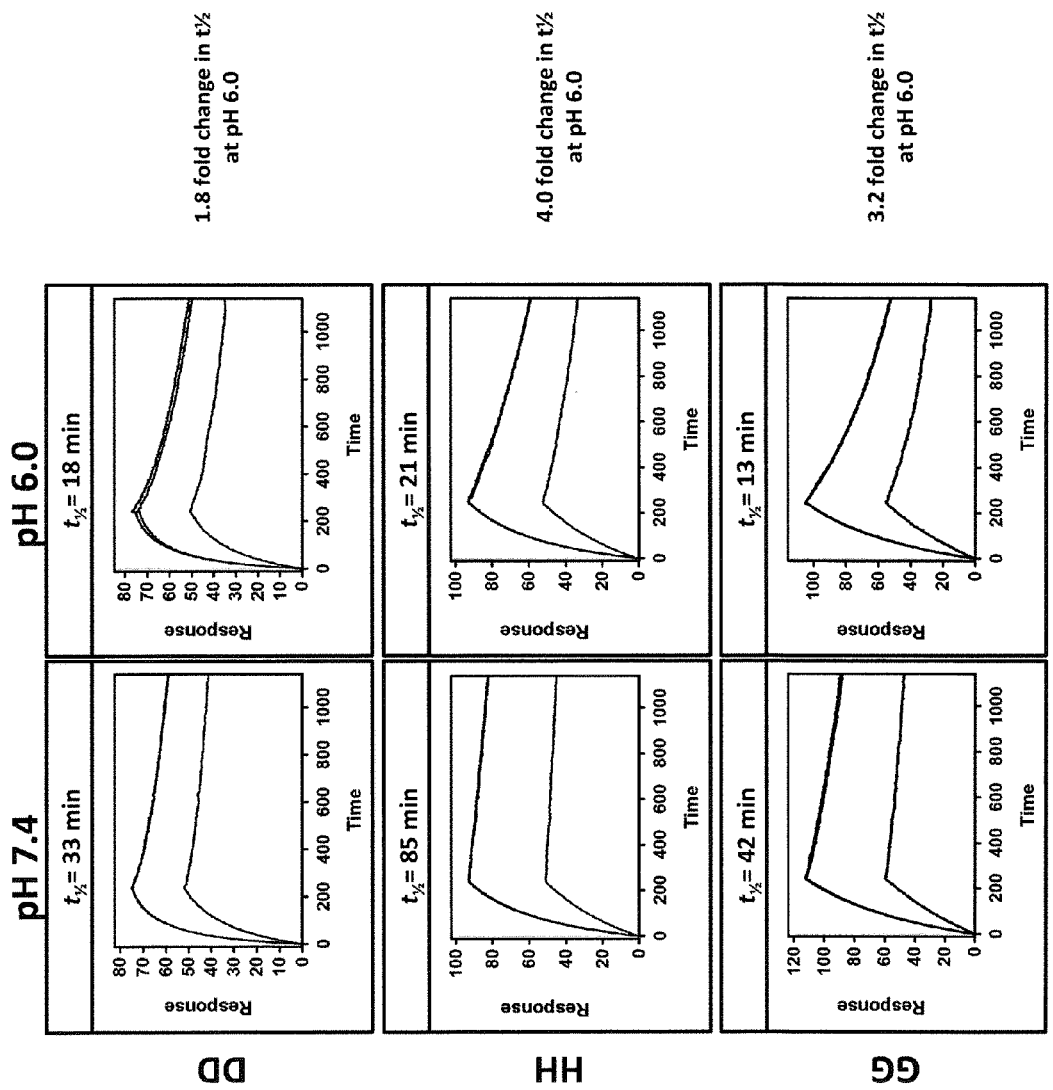
Figure 11C:
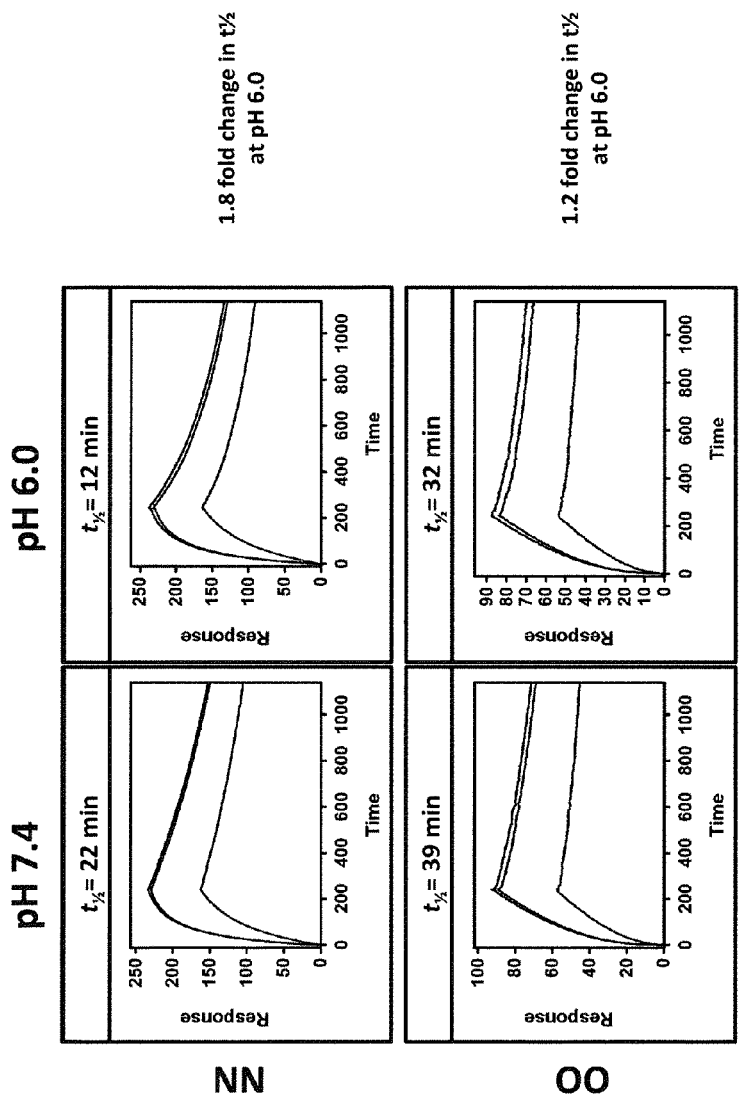

A Biacore CM4 sensor chip was derivatized with a polyclonal rabbit anti-mouse Fc antibody. Monoclonal antibody supernatants were captured onto the anti-mouse Fc sensor surface. Two concentrations, 50 nM (in duplicate) and 16.7 nM, of the immunogen were injected over the monoclonal antibody captured surface at a flow rate of 30 μl/min. Antibody-antigen association was monitored at pH 7.4 for 4 minutes and then the dissociation of antigen from the captured monoclonal antibody was monitored for 15 minutes at either pH 7.4 or 6.0. Dissociation ($k_d$) rate constants were determined by processing and fitting the data using Scrubber version 2.0 curve fitting software and are shown in Table 4. Dissociative half-lives ($t_{1/2}$) were calculated from the dissociation rate constants as: $t_{1/2}$ (min)=(ln $2/k_d$)/60, and are shown in Table 4. Sensorgrams depicting the association/dissociation characteristics of several antibodies listed in Table 4 under the various pH conditions are shown graphically in FIG. 11. The individual lines in each graph represent the binding responses at different concentrations of the respective antibodies. All experiments were carried out at 25° C. Dissociative half-life values ($t_{1/2}$) are noted above the respective sensorgrams. Response is measured in RU.

TABLE 4

Dissociation ($k_d$) rate constants and dissociative half-lives ($t_{1/2}$) of monoclonal HULC or WT antibodies binding to their immunogen at neutral and low pH.

| | | pH 7.4 Association/pH 7.4 Dissociation | | | | pH 7.4 Association/pH 6.0 Dissociation | | | | pH 6.0/ pH 7.4 ratio | |
|---|---|---|---|---|---|---|---|---|---|---|---|
| Clone Name | Light chain used | neutral mAb capture | 50 nM immunogen bound (RU) | $k_d$ (1/s) | $t_{1/2}$ (min) | low mab capture | 50 nM immunogen bound (RU) | $k_d$ (1/s) | $t_{1/2}$ (min) | $k_d$ | $t_{1/2}$ |
| AA | HULC (1927) | 129 | 70 | 5.60E−05 | 206 | 122 | 73 | 2.18E−04 | 53 | 3.9 | 0.3 |
| BB | HULC (1927) | 350 | 165 | 6.00E−04 | 19 | 378 | 185 | 2.20E−03 | 5 | 3.7 | 0.3 |
| CC | HULC (1927) | 611 | 251 | 2.03E−04 | 57 | 545 | 226 | 6.68E−03 | 2 | 33.0 | 0.03 |
| DD | HULC (1927) | 182 | 75 | 3.55E−04 | 33 | 168 | 74 | 6.44E−04 | 18 | 1.8 | 0.6 |
| HH | HULC (1927) | 268 | 92 | 1.36E−04 | 85 | 251 | 91 | 5.39E−04 | 21 | 4.0 | 0.3 |
| GG | HULC (1927) | 353 | 110 | 2.78E−04 | 42 | 328 | 102 | 8.97E−04 | 13 | 3.2 | 0.3 |
| FF | HULC (1927) | 334 | 202 | 4.79E−05 | 241 | 364 | 220 | 6.90E−05 | 167 | 1.4 | 0.7 |
| EE | HULC (1927) | 339 | 124 | 5.08E−04 | 23 | 299 | 120 | 4.66E−04 | 25 | 0.9 | 1.1 |
| II | HULC (1930) | 387 | 174 | 1.22E−04 | 95 | 334 | 147 | 2.14E−04 | 54 | 1.8 | 0.6 |
| JJ | HULC (1930) | 363 | 14 | 9.83E−04 | 12 | 333 | 12 | 5.30E−04 | 22 | 0.5 | 1.9 |
| KK | HULC (1930) | 490 | 303 | 7.41E−05 | 156 | 484 | 295 | 1.29E−04 | 90 | 1.7 | 0.6 |
| LL | HULC (1930) | 636 | 41 | 3.09E−04 | 37 | 597 | 36 | 5.77E−04 | 20 | 1.9 | 0.5 |
| MM* | WT (from 1927 mouse) | 245 | 6 | NA | NA | 203 | 6 | NA | NA | NA | NA |

TABLE 4-continued

Dissociation ($k_d$) rate constants and dissociative half-lives ($t_{1/2}$) of monoclonal
HULC or WT antibodies binding to their immunogen at neutral and low pH.

| | | | pH 7.4 Association/pH 7.4 Dissociation | | | | pH 7.4 Association/pH 6.0 Dissociation | | | pH 6.0/ pH 7.4 ratio | |
|---|---|---|---|---|---|---|---|---|---|---|---|
| Clone Name | Light chain used | neutral mAb capture | 50 nM immunogen bound (RU) | $k_d$ (1/s) | $t^{1/2}$ (min) | low mab capture | 50 nM immunogen bound (RU) | $k_d$ (1/s) | $t^{1/2}$ (min) | $k_d$ | $t^{1/2}$ |
| NN | WT (from 1927 mouse) | 394 | 231 | 5.26E−04 | 22 | 378 | 231 | 9.35E−04 | 12 | 1.8 | 0.6 |
| OO | WT | 413 | 89 | 2.94E−04 | 39 | 400 | 83 | 3.57E−04 | 32 | 1.2 | 0.8 |

*$k_d$ and $t_{1/2}$ values could not be determined due to low antigen binding signal Example 4

Engineering of Genetically Modified Mouse Comprising a Histidine-Substituted Vκ3-20Jκ1 Universal Light Chain A mouse comprising a common Vκ3-20Jκ1 light chain was generated as described in, e.g., U.S. patent application Ser. Nos. 13/022,759, 13/093,156, 13/412,936, and 13/488,628 (Publication Nos. 2011/0195454, 2012/0021409, 2012/0192300, and 2013/0045492, respectively), and in Example 1 above. The amino acid sequence of the germline universal Vκ3-20Jκ1 light chain variable domain is set forth in SEQ ID NO:59.

Histidine substitutions were introduced into the Vκ3-20Jκ1 universal light chain targeting vector and mice generated from the same using a similar strategy to the one described above in Example 3 for Vκ1-39Jκ5 histidine modified universal light chain mice (HULC 1927 and 1930).

Figure 14A:
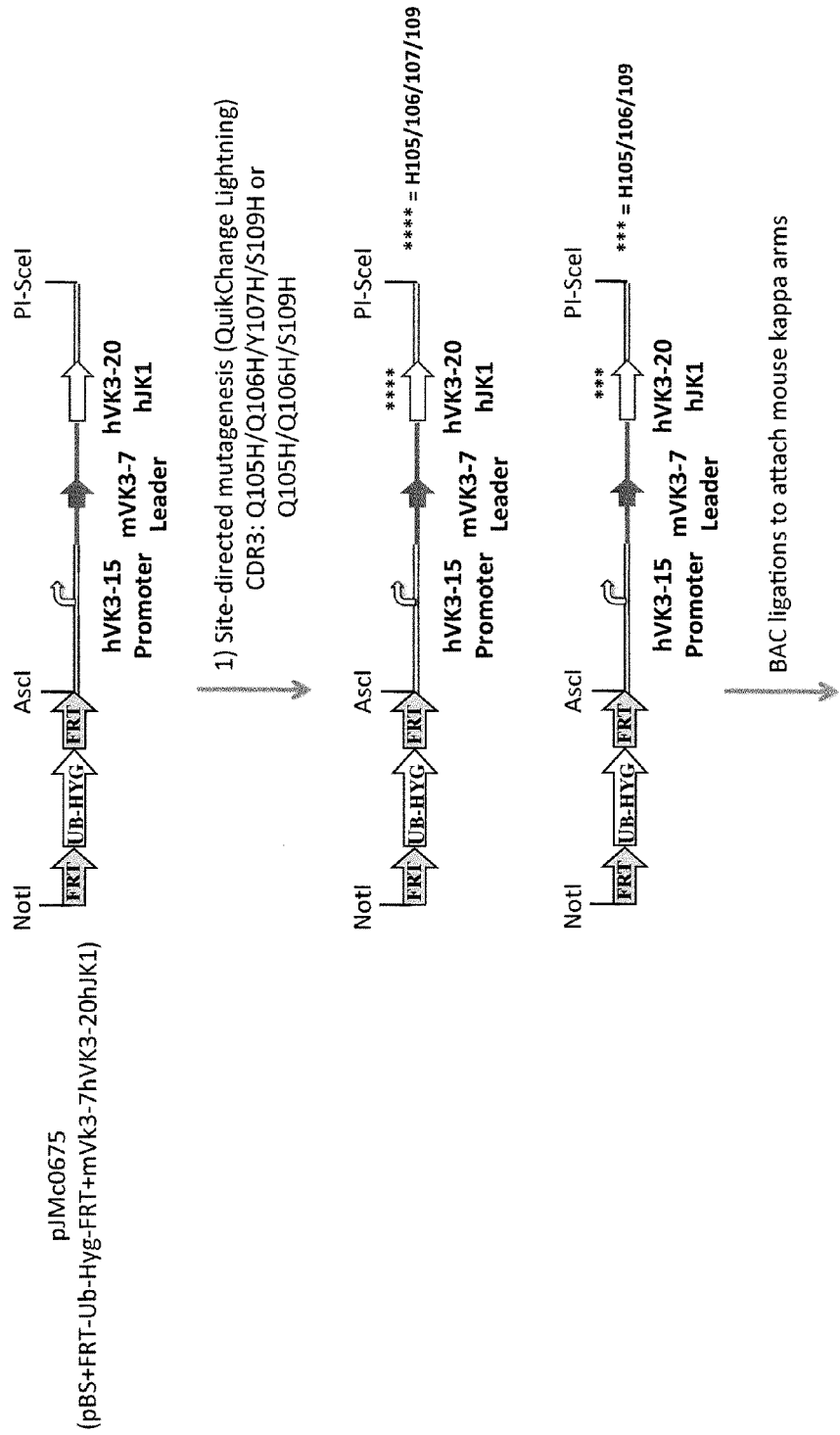
FIGS. 14A-14B show a general strategy for construction of targeting vectors for the engineering of histidine residues into a rearranged human light chain variable region sequence derived from Vκ3-20/Jκ1 light chain variable region for making a genetically modified mouse that expresses antibodies containing the modified human light chain.
Figure 14B:
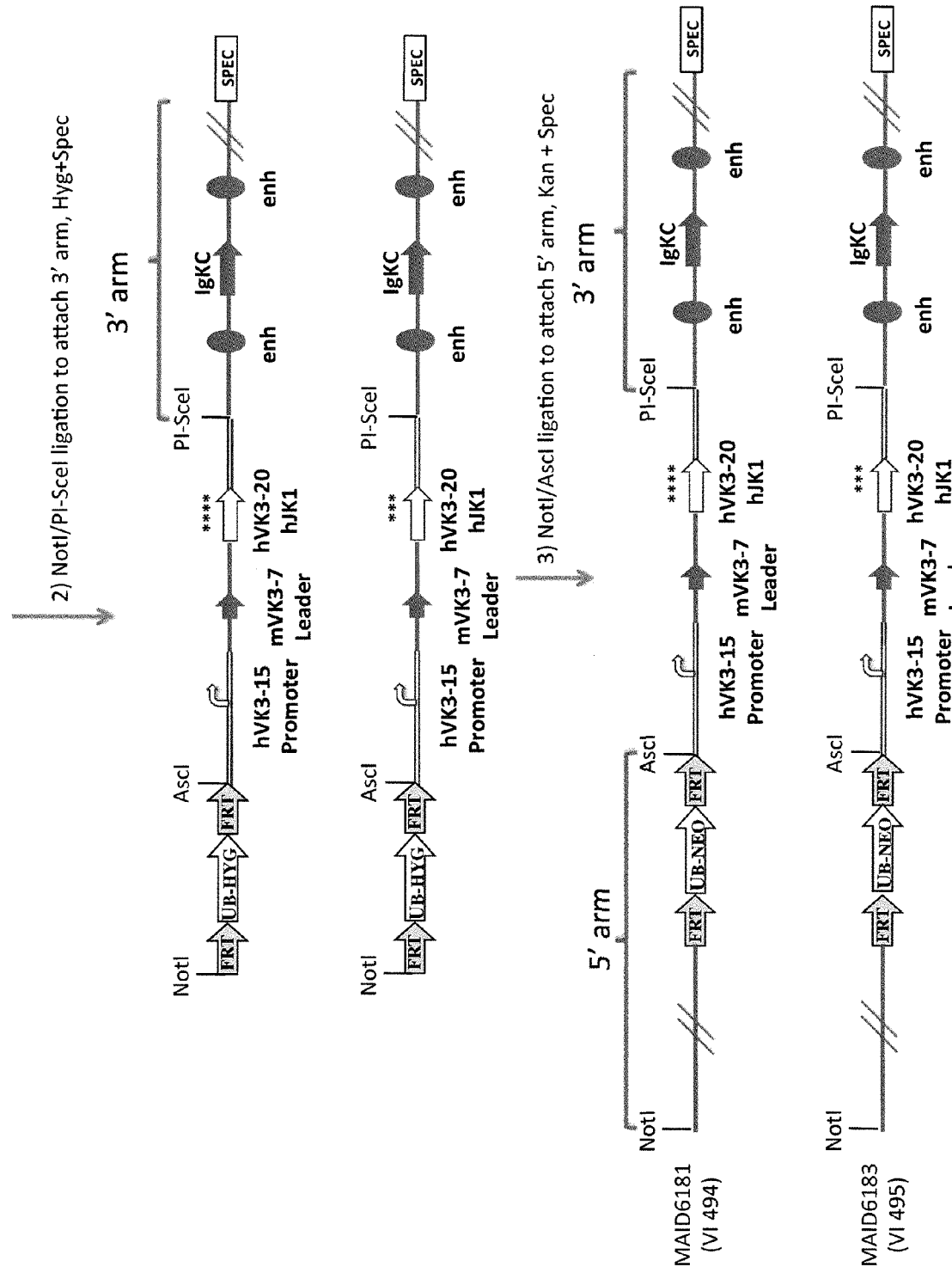
Figure 14C:
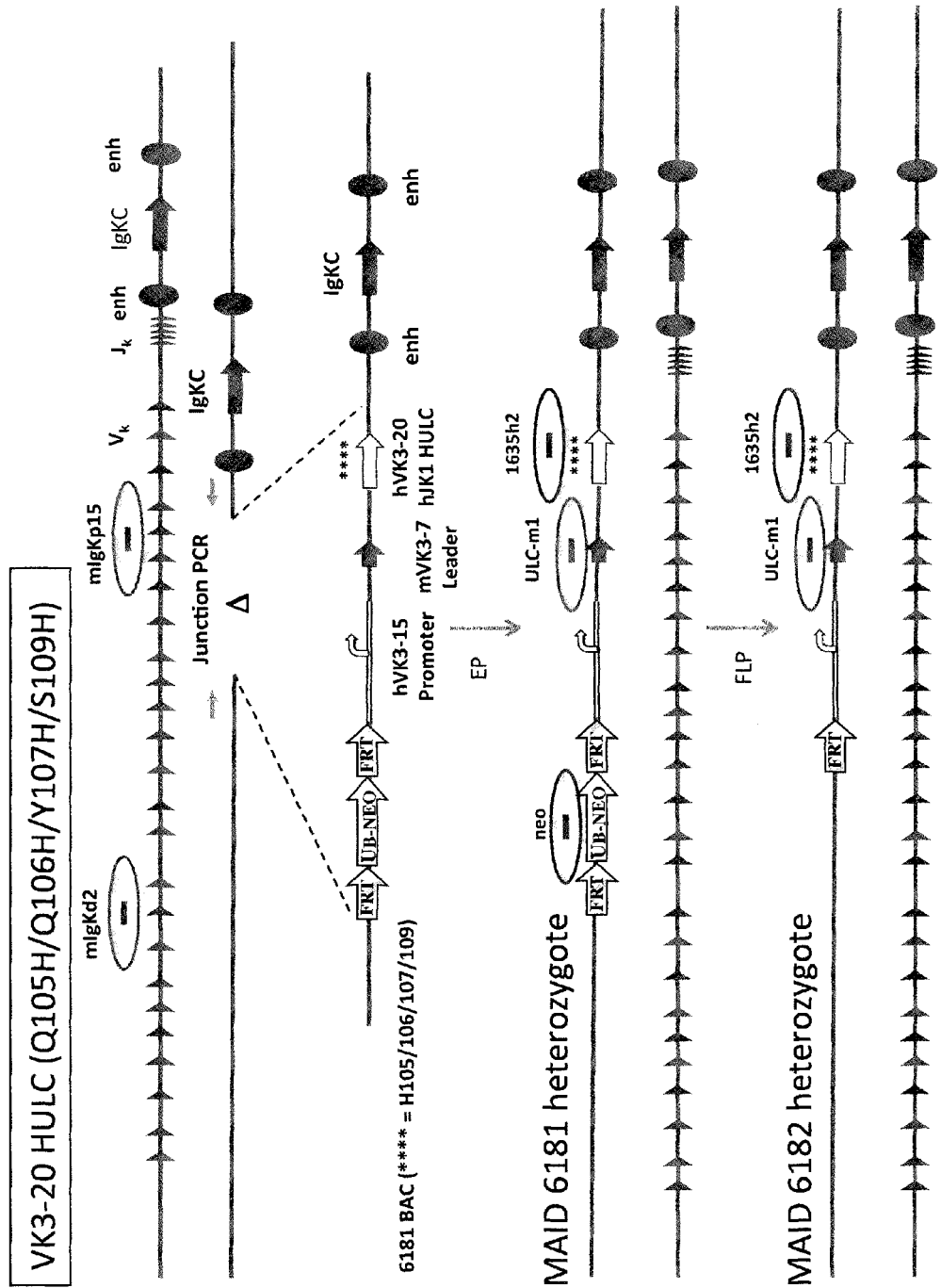
Figure 14D:
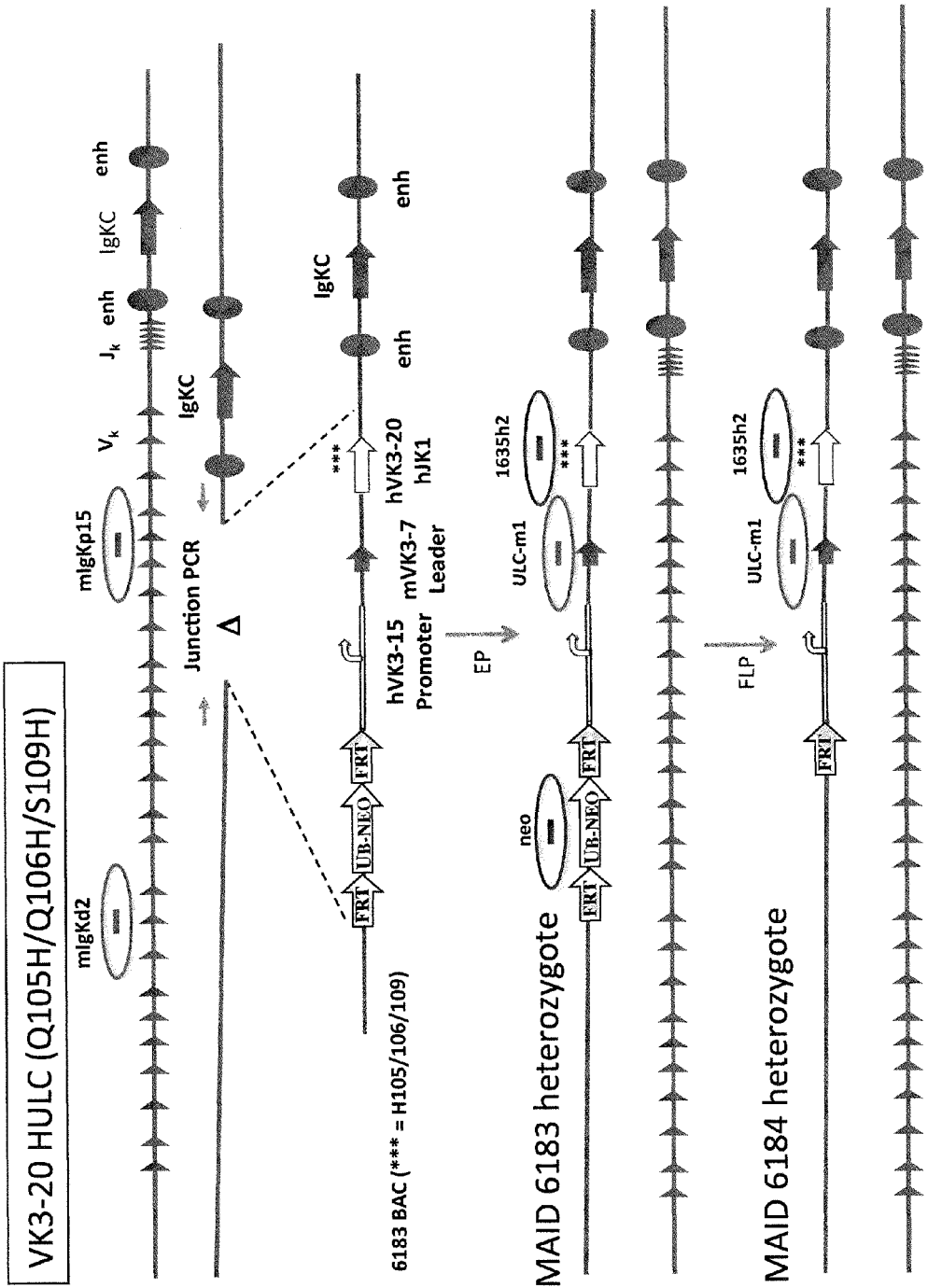
FIG. 14D shows introduction of the targeting vector for ULC-Q105H/Q106H/S109H substitutions into ES cells and generation of heterozygous mice from the same. The diagrams are not presented to scale. Unless indicated otherwise, filled shapes and solid lines represent mouse sequence, empty shapes and double lines represent human sequence.

Briefly, the strategy for generating a histidine-modified Vκ3-20Jκ1 universal light chain targeting vector is summarized in FIGS. 14A-14D. A plasmid used for generating a targeting vector for common (universal) light chain mouse ("ULC mouse," described in, e.g., US2011/0195454A1), containing pBS+FRT-Ub-Hyg-FRT+mouse Vκ3-7 leader+human Vκ3-20Jκ1 was modified by site directed mutagenesis (QuickChange Lightning Kit) to replace Q105, Q106, Y107 and S109 or Q105, Q106 and S109 (see alignment in FIG. 12) with histidine residues in the CDR3 region using site-directed mutagenesis primers shown in FIG. 13 (See FIG. 14A for this engineering step). Resultant vectors (H105/106/107/109 and H105/106/109) were modified further and ligated into a vector comprising mouse Igκ constant region, mouse enhancers, a mouse 3' homology arm and a SPEC cassette (FIG. 14B). Further modification involved ligation into a vector carrying 5' mouse arm and comprising Frt-UB-NEO-Frt cassette (FIG. 14B). Resultant targeting vectors were electroporated into ES cells comprising deletion of the mouse Igκ variable locus (comprising κ variable and joining gene segments) (FIGS. 14C-14D).

Positive ES cell clones were confirmed by using a modification of allele assay (Valenzuela et al.) using probes specific for the engineered Vκ3-20Jκ1 light chain region inserted into the endogenous κ light chain locus. Primers and probes used in the assay are shown in Table 5 below and set forth in the Sequence Listing; the locations of the probes are depicted in FIGS. 14C-14D.

TABLE 5

Primers and Probes Used for ES Cell Screening

| Probe Name | Assay | Probe Sequence | 5' Primer | 3' Primer |
|---|---|---|---|---|
| Neo | GOA | TGGGCACAACA GACAATCGGCTG (SEQ ID NO: 38) | GGTGGAGAGG CTATTCGGC (SEQ ID NO: 39) | GAACACGGCGG CATCAG (SEQ ID NO: 40) |
| ULC-m1 | GOA | CCATTATGATGCT CCATGCCTCTCT GTTC (SEQ ID NO: 41) | AGGTGAGGGT ACAGATAAGTG TTATGAG (SEQ ID NO: 42) | TGACAAATGCCC TAATTATAGTGAT CA (SEQ ID NO: 43) |
| 1635h2 (Vκ3-20Jκ1 specific) | GOA | AAAGAGCCACCC TCTCCTGCAGGG (SEQ ID NO: 65) | TCCAGGCACCC TGTCTTTG (SEQ ID NO: 66) | AAGTAGCTGCTG CTAACACTCTGAC T (SEQ ID NO: 67) |
| mIgKd2 | Retention | GGCCACATTCCA TGGGTTC (SEQ ID NO: 47) | GCAAACAAAAA CCACTGGCC (SEQ ID NO: 48) | CTGTTCCTCTAAA ACTGGACTCCAC AGTAAATGGAAA (SEQ ID NO: 49) |

TABLE 5-continued

Primers and Probes Used for ES Cell Screening

| Probe Name | Assay | Probe Sequence | 5' Primer | 3' Primer |
|---|---|---|---|---|
| mIgKp15 | Retention | GGGCACTGGATA CGATGTATGG (SEQ ID NO: 50) | CACAGCTTGTG CAGCCTCC (SEQ ID NO: 51) | AGAAGAAGCCTG TACTACAGCATCC GTTTTACAGTCA (SEQ ID NO: 52) |

The NEO selection cassette introduced by the targeting constructs is deleted by transfecting ES cells with a plasmid that expresses FLP (FIGS. 14C and 14D). Optionally, the neomycin cassette may be removed by breeding to mice that express FLP recombinase (e.g., U.S. Pat. No. 6,774,279). Optionally, the neomycin cassette is retained in the mice.

Targeted ES cells described above are used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® independently bearing an engineered human light chain gene that contains histidine residues mutated into one or more positions along the sequence are made from the targeted ES cells described above.

Pups are genotyped and pups heterozygous for the engineered histidine-modified human light chain are selected for characterizing expression of the light chain and binding capabilities of the expressed antibodies. Primers and probes for genotyping of mice specifically comprising a universal light chain gene with either three (H105/106/109; "6183") or four (H105/105/108/111; "6181") histidine modifications are listed in Table 6 below and set forth in the Sequence Listing. Mice containing histidine modification in their universal light chains are referred herein as "HULC" mice (histidine universal light chain mice).

Endogenous Igλ Knockout (KO). To optimize the usage of the engineered light chain locus, any one of the HULC animals described above (e.g., comprising Vκ1-39Jκ5 or Vκ3-20Jκ1 histidine-substituted universal light chain) may be bred to another mouse containing a deletion in the endogenous λ light chain locus. In this manner, the progeny obtained will express, as their only light chain, the rearranged histidine-substituted human germline light chain region as described in Examples 3 and 4 above. Breeding is performed by standard techniques recognized in the art and, alternatively, by a commercial breeder (e.g., The Jackson Laboratory). Mouse strains bearing an engineered histidine-substituted light chain locus and a deletion of the endogenous λ light chain locus are screened for presence of the unique light chain region and absence of endogenous mouse λ light chains.

Humanized Endogenous Heavy Chain Locus.

Mice bearing an engineered human germline light chain locus (HULC mice) are bred with mice that contain a replacement of the endogenous mouse heavy chain variable gene locus with the human heavy chain variable gene locus (see U.S. Pat. No. 6,596,541; the VELOCIMMUNE® mouse, Regeneron Pharmaceuticals, Inc.). The VELOCIMMUNE® mouse comprises a genome comprising human heavy chain variable regions operably linked to endogenous mouse constant region loci such that the mouse produces antibodies comprising a human heavy chain variable domain and a mouse heavy chain constant region in response to antigenic stimulation.

TABLE 6

Primers and Probes Used for Genotyping

| Probe Name | Assay | Probe Sequence | 5' Primer | 3' Primer |
|---|---|---|---|---|
| hVI494-1 | GOA 6181 (4 His) mouse-specific | CTGTCATCACCATG G (SEQ ID NO: 68) | GCAGACTGGAGC CTGAAGATTTT (SEQ ID NO: 69) | CCGAACGTCCAAGG TGAGTG (SEQ ID NO: 70) |
| hVI495-1 | GOA 6183 (3 His) mouse-specific | TACTGTCATCACTAT GG (SEQ ID NO: 71) | GCAGACTGGAGC CTGAAGATTT (SEQ ID NO: 72) | CCGAACGTCCAAGG TGAGTG (SEQ ID NO: 73) |

Mice are immunized with antigen of interest and tested for ability to generate antibodies with pH-dependent binding.

Example 5

Breeding of Mice Comprising a Histidine-Substituted Single Rearranged Human Universal Light Chain Mouse (HULC)

This Example describes several other genetically modified mouse strains that can be bred to any one of the HULC mice described herein to create multiple genetically modified mouse strains harboring multiple genetically modified immunoglobulin loci.

Mice bearing a replacement of the endogenous mouse heavy chain variable region locus with the human heavy chain variable region locus and a histidine-substituted single rearranged human light chain variable region at the endogenous κ light chain locus are obtained. Reverse chimeric antibodies containing somatically mutated heavy chains (human heavy chain variable domain and mouse $C_H$) with a histidine-substituted single human light chain (HULC, human light chain variable domain and mouse $C_L$) are obtained upon immunization with an antigen of interest. pH-dependent human antibodies generated in such mice are identified using antibody isolation and screening methods known in the art or described above. Variable light and heavy chain region nucleotide sequences of B cells expressing the antibodies, e.g., pH-sensitive antibodies, are identified, and fully human antibodies are made by fusion of the variable heavy and light chain region nucleotide sequences to human $C_H$ and $C_L$ nucleotide sequences, respectively, in a suitable expression system.

EQUIVALENTS

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A genetically modified non-human animal comprising in its germline an immunoglobulin light chain locus that comprises a single rearranged human immunoglobulin light chain variable region gene sequence comprising human Vκ and Jκ segment sequences, wherein the Vκ segment sequence is derived from a human Vκ1-39 or Vκ3-20 gene segment, and wherein the single rearranged human immunoglobulin light chain variable region gene sequence comprises a substitution of at least one non-histidine codon of the Vκ segment sequence with a histidine codon that is expressed at a position selected from the group consisting of 105, 106, 107, 108, 109, 111 and a combination thereof (according to IMGT numbering).

2. The animal of claim 1, wherein the single rearranged human immunoglobulin variable region sequence is operably linked to an immunoglobulin light chain constant region gene sequence.

3. The animal of claim 2, wherein the immunoglobulin light chain constant region gene sequence is a non-human immunoglobulin light chain constant region gene sequence.

4. The animal of claim 3, wherein the non-human immunoglobulin light chain constant region gene sequence is an endogenous non-human immunoglobulin light chain constant region gene sequence.

5. The animal of claim 1, further comprising in its germline an immunoglobulin heavy chain locus that comprises an unrearranged immunoglobulin heavy chain variable region gene sequence comprising human $V_H$, $D_H$, and $J_H$ segments operably linked to an immunoglobulin heavy chain constant region gene sequence.

6. The animal of claim 5, wherein the immunoglobulin heavy chain constant region gene sequence is a non-human immunoglobulin heavy chain constant region gene sequence.

7. The animal of claim 6, wherein the non-human heavy chain constant region gene sequence is an endogenous non-human immunoglobulin constant region gene sequence.

8. The animal of claim 1, wherein the animal lacks a functional unrearranged immunoglobulin κ light chain variable region.

9. The animal of claim 1, wherein the immunoglobulin light chain locus is at an endogenous non-human immunoglobulin light chain locus.

10. The animal of claim 5, wherein the immunoglobulin heavy chain locus is at an endogenous non-human immunoglobulin heavy chain locus.

11. The animal of claim 1, wherein the substitution of at least one non-histidine codon with a histidine codon is in the nucleotide sequence encoding a complementary determining region (CDR) 3.

12. The animal of claim 11, wherein the substitution is of one, two, three, or four CDR3 codon(s).

13. The animal of claim 1, wherein the single rearranged human immunoglobulin light chain variable region is derived from a rearranged Vκ1-39/Jκ5 or Vκ3-20/Jκ1 gene sequence.

14. The animal of claim 13, wherein the single rearranged human immunoglobulin light chain variable region is derived from a rearranged Vκ1-39/Jκ5 gene sequence, and wherein the Vκ1-39/Jκ5 gene sequence comprises a replacement of at least one non-histidine codon with a histidine codon designed to express a histidine at a position selected from the group consisting of 105, 106, 108, 111, and a combination thereof (according to IMGT numbering).

15. The animal of claim 13, wherein the single rearranged human immunoglobulin light chain variable region is derived from a rearranged Vκ3-20/Jκ1 gene sequence, and wherein the Vκ3-20/Jκ1 gene sequence comprises a replacement of at least one non-histidine codon with a histidine codon designed to express a histidine at position selected from the group consisting of 105, 106, 107, 109, and a combination thereof (according to IMGT numbering).

16. The animal of claim 1, wherein the animal comprises a population of B cells in response to an antigen of interest that is enriched for antibodies that exhibit a decrease in dissociative half-life ($t_{1/2}$) at an acidic pH as compared to neutral pH of at least about 2-fold, at least about 3-fold, at least about 4-fold, at least about 5-fold, at least about 10-fold, at least about 15-fold, at least about 20-fold, at least about 25-fold, or at least about 30-fold.

17. The animal of claim 16, wherein the decrease in dissociative half-life ($t_{1/2}$) at an acidic pH as compared to neutral pH is about 30 fold or more.

18. The animal of claim 1, wherein the animal is a rodent.

19. The rodent of claim 18, wherein the rodent is a rat or a mouse.

20. The rodent of claim 19, wherein the rodent is a mouse.

21. The animal of claim 1, wherein the animal expresses an antibody comprising a human immunoglobulin light chain variable domain with a substitution of at least one non-histidine residue with a histidine at an amino acid position encoded by the at least one codon substituted in the immunoglobulin light chain variable region gene sequence.

22. A genetically modified mouse comprising in its germline an immunoglobulin light chain locus that comprises a single rearranged human immunoglobulin light chain variable region gene sequence comprising human Vκ and Jκ segment sequences,
wherein the Vκ segment sequence is derived from a human Vκ1-39 or Vκ3-20 gene segment, and
wherein the single rearranged human immunoglobulin light chain variable region sequence comprises a substitution of at least one non-histidine codon of the Vκ segment sequence with a histidine codon that is expressed at a position selected from the group consisting of 105, 106, 107, 108, 109, 111 and a combination thereof (according to IMGT numbering), and
wherein the mouse lacks a functional unrearranged immunoglobulin κ light chain variable region.

23. The mouse of claim 22, wherein the single rearranged immunoglobulin light chain variable region gene sequence is operably linked to an immunoglobulin light chain constant region gene sequence.

24. The mouse of claim 23, wherein the immunoglobulin light chain constant region gene sequence is selected from a rat or a mouse immunoglobulin light chain constant region gene sequence.

25. The mouse of claim 22, further comprising in its germline an immunoglobulin heavy chain locus that comprises an unrearranged immunoglobulin heavy chain variable region sequence comprising human $V_H$, $D_H$, and $J_H$ segments operably linked to an immunoglobulin heavy chain constant region gene sequence.

26. The mouse of claim 25, wherein the immunoglobulin heavy chain constant region gene sequence is a rat or a mouse heavy chain constant region gene sequence.

27. The mouse of claim 22, wherein the immunoglobulin light chain locus is at an endogenous mouse immunoglobulin light chain locus.

28. The mouse of claim 25, wherein the immunoglobulin heavy chain locus is at an endogenous mouse immunoglobulin heavy chain locus.

29. The mouse of claim 22, wherein the substitution of at least one non-histidine codon with a histidine codon is in the nucleotide sequence encoding a complementary determining region (CDR) 3.

30. The mouse of claim 29, wherein the substitution is of one, two, three, or four CDR3 codon(s).

31. The mouse of claim 22, wherein the single rearranged human immunoglobulin light chain variable region is derived from a rearranged Vκ1-39/Jκ5 or Vκ3-20/Jκ1 gene sequence.

32. The mouse of claim 31, wherein the single rearranged human immunoglobulin light chain variable region is derived from a rearranged Vκ1-39/Jκ5 gene sequence, and wherein the Vκ1-39/Jκ5 gene sequence comprises a replacement of at least one non-histidine codon with a histidine codon designed to express a histidine at a position selected from the group consisting of 105, 106, 108, 111, and a combination thereof (according to IMGT numbering).

33. The mouse of claim 32, wherein the Vκ1-39/Jκ5 gene sequence comprises a replacement of non-histidine codons designed to express histidines at positions 105, 106, 108, and 111 (according to IMGT numbering).

34. The mouse of claim 32, wherein the Vκ1-39/Jκ5 gene sequence comprises a replacement of non-histidine codons designed to express histidines at positions 106, 108 and 111 (according to IMGT numbering).

35. The mouse of claim 31, wherein the single rearranged human immunoglobulin light chain variable region is derived from a rearranged Vκ3-20/Jκ1 gene sequence, and wherein the Vκ3-20/Jκ1 gene sequence comprises replacement of at least one non-histidine codon with a histidine codon designed to express a histidine at a position selected from the group consisting of 105, 106, 107, 109, and a combination thereof (according to IMGT numbering).

36. The mouse of claim 35, wherein the Vκ3-20/Jκ1 gene sequence comprises a replacement of non-histidine codons designed to express histidines at positions 105, 106, 107, and 109 (according to IMGT numbering).

37. The mouse of claim 35, wherein the Vκ3-20/Jκ1 gene sequence comprises a replacement of non-histidine codons designed to express histidines at IGMT positions 105, 106 and 109 (according to IMGT numbering).

38. The mouse of claim 22, wherein the mouse expresses a population of antigen-specific antibodies in response to an antigen of interest wherein all antibodies comprise:
   immunoglobulin light chain variable domains derived from the same single rearranged human light chain variable region gene sequence which comprises a substitution of at least one non-histidine codon with a histidine codon, and
   immunoglobulin heavy chains comprising human heavy chain variable domains derived from a repertoire of human heavy chain V, D, and J segments.

39. A method of generating an antibody that exhibits pH-dependent binding to an antigen of interest comprising:
   generating a mouse of claim 22;
   immunizing the mouse with an antigen of interest; and
   selecting an antibody that binds to the antigen of interest with a desired affinity at a neutral pH while displaying reduced binding to the antigen of interest at an acidic pH.

40. The method of claim 39, wherein the antibody exhibits a dissociative half-life ($t_{1/2}$) at acidic pH and 37° C. of about 2 minutes or less.

41. A method of making a non-human animal that comprises a genetically modified immunoglobulin light chain locus in its germline, the method comprising:
   modifying a genome of a non-human animal to delete or render non-functional endogenous immunoglobulin light chain Vκ and Jκ segments in an immunoglobulin light chain locus, and
   placing in the genome a single rearranged human light chain variable region gene sequence comprising human Vκ and Jκ segment sequences,
   wherein the Vκ segment sequence is derived from a human Vκ1-39 or Vκ3-20 gene segment, and
   wherein the single rearranged human immunoglobulin light chain variable region gene sequence comprises a substitution of at least one non-histidine codon of the Vκ segment sequence with a histidine codon that is expressed at a position selected from the group consisting of 105, 106, 107, 108, 109, 111 and a combination thereof (according to IMGT numbering).

42. The method of claim 41, wherein the method results in a genetically modified non-human animal that comprises a population of B cells enriched for antibodies exhibiting pH-dependent binding to an antigen of interest.

43. The method of claim 41, wherein the animal is a rodent.

44. The method of claim 43, wherein the animal is a mouse or a rat.

* * * * *

SEQUENCE LISTING

```
<160> NUMBER OF SEQ ID NOS: 92

<210> SEQ ID NO 1
<211> LENGTH: 95
<212> TYPE: PRT
<213> ORGANISM: Artificial
<220> FEATURE:
<223> OTHER INFORMATION: Synthetic

<400> SEQUENCE: 1

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 2
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 2 cag cag agc tac agc acc ccc                                      21
Gln Gln Ser Tyr Ser Thr Pro
1               5

<210> SEQ ID NO 3
<211> LENGTH: 7
<212> TYPE: PRT
<213> ORGANISM: Artificial
<220> FEATURE:
<223> OTHER INFORMATION: Synthetic Construct

<400> SEQUENCE: 3

Gln Gln Ser Tyr Ser Thr Pro
1               5

<210> SEQ ID NO 4
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
```

```
<222> LOCATION: (1)..(21)

<400> SEQUENCE: 4 cac cat agc cac agc acc cac                                          21
His His Ser His Ser Thr His
1               5

<210> SEQ ID NO 5
<211> LENGTH: 7
<212> TYPE: PRT
<213> ORGANISM: Artificial
<220> FEATURE:
<223> OTHER INFORMATION: Synthetic Construct

<400> SEQUENCE: 5

His His Ser His Ser Thr His
1               5

<210> SEQ ID NO 6
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 6 cac cag agc tac agc acc ccc                                          21
His Gln Ser Tyr Ser Thr Pro
1               5

<210> SEQ ID NO 7
<211> LENGTH: 7
<212> TYPE: PRT
<213> ORGANISM: Artificial
<220> FEATURE:
<223> OTHER INFORMATION: Synthetic Construct

<400> SEQUENCE: 7

His Gln Ser Tyr Ser Thr Pro
1               5

<210> SEQ ID NO 8
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 8 cag cat agc tac agc acc ccc                                          21
Gln His Ser Tyr Ser Thr Pro
1               5

<210> SEQ ID NO 9
<211> LENGTH: 7
<212> TYPE: PRT
<213> ORGANISM: Artificial
<220> FEATURE:
<223> OTHER INFORMATION: Synthetic Construct

<400> SEQUENCE: 9
```

Gln His Ser Tyr Ser Thr Pro
1               5

<210> SEQ ID NO 10
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 10 cag cag agc cac agc acc ccc                                      21
Gln Gln Ser His Ser Thr Pro
1               5

<210> SEQ ID NO 11
<211> LENGTH: 7
<212> TYPE: PRT
<213> ORGANISM: Artificial
<220> FEATURE:
<223> OTHER INFORMATION: Synthetic Construct

<400> SEQUENCE: 11

Gln Gln Ser His Ser Thr Pro
1               5

<210> SEQ ID NO 12
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 12 cag cag agc tac agc acc cac                                      21
Gln Gln Ser Tyr Ser Thr His
1               5

<210> SEQ ID NO 13
<211> LENGTH: 7
<212> TYPE: PRT
<213> ORGANISM: Artificial
<220> FEATURE:
<223> OTHER INFORMATION: Synthetic Construct

<400> SEQUENCE: 13

Gln Gln Ser Tyr Ser Thr His
1               5

<210> SEQ ID NO 14
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 14 cac cat agc tac agc acc ccc                                      21
His His Ser Tyr Ser Thr Pro
1               5

```
<210> SEQ ID NO 15
<211> LENGTH: 7
<212> TYPE: PRT
<213> ORGANISM: Artificial
<220> FEATURE:
<223> OTHER INFORMATION: Synthetic Construct

<400> SEQUENCE: 15

His His Ser Tyr Ser Thr Pro
1               5

<210> SEQ ID NO 16
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 16 cac cag agc cac agc acc ccc                                        21
His Gln Ser His Ser Thr Pro
1               5

<210> SEQ ID NO 17
<211> LENGTH: 7
<212> TYPE: PRT
<213> ORGANISM: Artificial
<220> FEATURE:
<223> OTHER INFORMATION: Synthetic Construct

<400> SEQUENCE: 17

His Gln Ser His Ser Thr Pro
1               5

<210> SEQ ID NO 18
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 18 cac cag agc tac agc acc cac                                        21
His Gln Ser Tyr Ser Thr His
1               5

<210> SEQ ID NO 19
<211> LENGTH: 7
<212> TYPE: PRT
<213> ORGANISM: Artificial
<220> FEATURE:
<223> OTHER INFORMATION: Synthetic Construct

<400> SEQUENCE: 19

His Gln Ser Tyr Ser Thr His
1               5

<210> SEQ ID NO 20
<211> LENGTH: 21
<212> TYPE: DNA
<213> ORGANISM: Artificial
```

```
-continued

<220> FEATURE:
<223> OTHER INFORMATION: Synthetic
<220> FEATURE:
<221> NAME/KEY: CDS
<222> LOCATION: (1)..(21)

<400> SEQUENCE: 20 cag cat agc cac agc acc ccc                                          21
Gln His Ser His Ser Thr Pro
1               5

<210> SEQ ID NO 21
<211> LENGTH: 7
<212> TYPE: PRT
<213> ORGANISM: Artificial
<220> FEATURE:
<223> OTHER INFORMATION: Synthetic Construct

<400> SEQUENCE: 21

Gln His Ser His Ser Thr Pro
1               5

<210> SEQ ID NO 22
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 22 cag cat agc tac agc acc cac                                          21
Gln His Ser Tyr Ser Thr His
1               5

<210> SEQ ID NO 23
<211> LENGTH: 7
<212> TYPE: PRT
<213> ORGANISM: Artificial
<220> FEATURE:
<223> OTHER INFORMATION: Synthetic Construct

<400> SEQUENCE: 23

Gln His Ser Tyr Ser Thr His
1               5

<210> SEQ ID NO 24
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 24 cag cag agc cac agc acc cac                                          21
Gln Gln Ser His Ser Thr His
1               5

<210> SEQ ID NO 25
<211> LENGTH: 7
<212> TYPE: PRT
<213> ORGANISM: Artificial
<220> FEATURE:
<223> OTHER INFORMATION: Synthetic Construct
```

<400> SEQUENCE: 25

Gln Gln Ser His Ser Thr His
1               5

<210> SEQ ID NO 26
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 26 cac cat agc cac agc acc ccc                                          21
His His Ser His Ser Thr Pro
1               5

<210> SEQ ID NO 27
<211> LENGTH: 7
<212> TYPE: PRT
<213> ORGANISM: Artificial
<220> FEATURE:
<223> OTHER INFORMATION: Synthetic Construct

<400> SEQUENCE: 27

His His Ser His Ser Thr Pro
1               5

<210> SEQ ID NO 28
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 28 cac cat agc tac agc acc cac                                          21
His His Ser Tyr Ser Thr His
1               5

<210> SEQ ID NO 29
<211> LENGTH: 7
<212> TYPE: PRT
<213> ORGANISM: Artificial
<220> FEATURE:
<223> OTHER INFORMATION: Synthetic Construct

<400> SEQUENCE: 29

His His Ser Tyr Ser Thr His
1               5

<210> SEQ ID NO 30
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 30

```
cac cag agc cac agc acc cac                                            21
His Gln Ser His Ser Thr His
  1               5
```

<210> SEQ ID NO 31
<211> LENGTH: 7
<212> TYPE: PRT
<213> ORGANISM: Artificial
<220> FEATURE:
<223> OTHER INFORMATION: Synthetic Construct

<400> SEQUENCE: 31

```
His Gln Ser His Ser Thr His
  1               5
```

<210> SEQ ID NO 32
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 32

```
cag cat agc cac agc acc cac                                            21
Gln His Ser His Ser Thr His
  1               5
```

<210> SEQ ID NO 33
<211> LENGTH: 7
<212> TYPE: PRT
<213> ORGANISM: Artificial
<220> FEATURE:
<223> OTHER INFORMATION: Synthetic Construct

<400> SEQUENCE: 33

```
Gln His Ser His Ser Thr His
  1               5
```

<210> SEQ ID NO 34
<211> LENGTH: 45
<212> TYPE: DNA
<213> ORGANISM: Artificial
<220> FEATURE:
<223> OTHER INFORMATION: Synthetic

<400> SEQUENCE: 34
cttactactg tcaacatagt cacagtaccc atccgatcac cttcg            45

<210> SEQ ID NO 35
<211> LENGTH: 50
<212> TYPE: DNA
<213> ORGANISM: Artificial
<220> FEATURE:
<223> OTHER INFORMATION: Synthetic

<400> SEQUENCE: 35
caacttacta ctgtcaccat agtcacagta cccatccgat caccttcggc            50

<210> SEQ ID NO 36
<211> LENGTH: 45
<212> TYPE: DNA
<213> ORGANISM: Artificial
<220> FEATURE:
<223> OTHER INFORMATION: Synthetic

<400> SEQUENCE: 36
cgaaggtgat cggatgggta ctgtgactat gttgacagta gtaag        45

<210> SEQ ID NO 37
<211> LENGTH: 50
<212> TYPE: DNA
<213> ORGANISM: Artificial
<220> FEATURE:
<223> OTHER INFORMATION: Synthetic

<400> SEQUENCE: 37
gccgaaggtg atcggatggg tactgtgact atggtgacag tagtaagttg        50

<210> SEQ ID NO 38
<211> LENGTH: 23
<212> TYPE: DNA
<213> ORGANISM: Artificial
<220> FEATURE:
<223> OTHER INFORMATION: Synthetic

<400> SEQUENCE: 38
tgggcacaac agacaatcgg ctg        23

<210> SEQ ID NO 39
<211> LENGTH: 19
<212> TYPE: DNA
<213> ORGANISM: Artificial
<220> FEATURE:
<223> OTHER INFORMATION: Synthetic

<400> SEQUENCE: 39
ggtggagagg ctattcggc        19

<210> SEQ ID NO 40
<211> LENGTH: 17
<212> TYPE: DNA
<213> ORGANISM: Artificial
<220> FEATURE:
<223> OTHER INFORMATION: Synthetic

<400> SEQUENCE: 40
gaacacggcg gcatcag        17

<210> SEQ ID NO 41
<211> LENGTH: 29
<212> TYPE: DNA
<213> ORGANISM: Artificial
<220> FEATURE:
<223> OTHER INFORMATION: Synthetic

<400> SEQUENCE: 41
ccattatgat gctccatgcc tctctgttc        29

<210> SEQ ID NO 42
<211> LENGTH: 28
<212> TYPE: DNA
<213> ORGANISM: Artificial
<220> FEATURE:
<223> OTHER INFORMATION: Synthetic

<400> SEQUENCE: 42
aggtgagggt acagataagt gttatgag        28

<210> SEQ ID NO 43
<211> LENGTH: 27

```
<212> TYPE: DNA
<213> ORGANISM: Artificial
<220> FEATURE:
<223> OTHER INFORMATION: Synthetic

<400> SEQUENCE: 43
tgacaaatgc cctaattata gtgatca                                           27

<210> SEQ ID NO 44
<211> LENGTH: 26
<212> TYPE: DNA
<213> ORGANISM: Artificial
<220> FEATURE:
<223> OTHER INFORMATION: Synthetic

<400> SEQUENCE: 44
atcagcagaa accagggaaa gcccct                                            26

<210> SEQ ID NO 45
<211> LENGTH: 21
<212> TYPE: DNA
<213> ORGANISM: Artificial
<220> FEATURE:
<223> OTHER INFORMATION: Synthetic

<400> SEQUENCE: 45
gggcaagtca gagcattagc a                                                 21

<210> SEQ ID NO 46
<211> LENGTH: 21
<212> TYPE: DNA
<213> ORGANISM: Artificial
<220> FEATURE:
<223> OTHER INFORMATION: Synthetic

<400> SEQUENCE: 46
tgcaaactgg atgcagcata g                                                 21

<210> SEQ ID NO 47
<211> LENGTH: 19
<212> TYPE: DNA
<213> ORGANISM: Artificial
<220> FEATURE:
<223> OTHER INFORMATION: Synthetic

<400> SEQUENCE: 47
ggccacattc catgggttc                                                    19

<210> SEQ ID NO 48
<211> LENGTH: 20
<212> TYPE: DNA
<213> ORGANISM: Artificial
<220> FEATURE:
<223> OTHER INFORMATION: Synthetic

<400> SEQUENCE: 48
gcaaacaaaa accactggcc                                                   20

<210> SEQ ID NO 49
<211> LENGTH: 37
<212> TYPE: DNA
<213> ORGANISM: Artificial
<220> FEATURE:
<223> OTHER INFORMATION: Synthetic

<400> SEQUENCE: 49
```
ctgttcctct aaaactggac tccacagtaa atggaaa					37

<210> SEQ ID NO 50
<211> LENGTH: 22
<212> TYPE: DNA
<213> ORGANISM: Artificial
<220> FEATURE:
<223> OTHER INFORMATION: Synthetic

<400> SEQUENCE: 50
gggcactgga tacgatgtat gg					22

<210> SEQ ID NO 51
<211> LENGTH: 19
<212> TYPE: DNA
<213> ORGANISM: Artificial
<220> FEATURE:
<223> OTHER INFORMATION: Synthetic

<400> SEQUENCE: 51
cacagcttgt gcagcctcc					19

<210> SEQ ID NO 52
<211> LENGTH: 37
<212> TYPE: DNA
<213> ORGANISM: Artificial
<220> FEATURE:
<223> OTHER INFORMATION: Synthetic

<400> SEQUENCE: 52
agaagaagcc tgtactacag catccgtttt acagtca					37

<210> SEQ ID NO 53
<211> LENGTH: 19
<212> TYPE: DNA
<213> ORGANISM: Artificial
<220> FEATURE:
<223> OTHER INFORMATION: Synthetic

<400> SEQUENCE: 53
accatagtca cagtaccca					19

<210> SEQ ID NO 54
<211> LENGTH: 23
<212> TYPE: DNA
<213> ORGANISM: Artificial
<220> FEATURE:
<223> OTHER INFORMATION: Synthetic

<400> SEQUENCE: 54
agcagtctgc aacctgaaga ttt					23

<210> SEQ ID NO 55
<211> LENGTH: 18
<212> TYPE: DNA
<213> ORGANISM: Artificial
<220> FEATURE:
<223> OTHER INFORMATION: Synthetic

<400> SEQUENCE: 55
cccttggccg aaggtgat					18

<210> SEQ ID NO 56
<211> LENGTH: 19
<212> TYPE: DNA
<213> ORGANISM: Artificial

```
<220> FEATURE:
<223> OTHER INFORMATION: Synthetic

<400> SEQUENCE: 56
atagtcacag tacccatcc                                                   19

<210> SEQ ID NO 57
<211> LENGTH: 23
<212> TYPE: DNA
<213> ORGANISM: Artificial
<220> FEATURE:
<223> OTHER INFORMATION: Synthetic

<400> SEQUENCE: 57
agtctgcaac ctgaagattt tgc                                              23

<210> SEQ ID NO 58
<211> LENGTH: 18
<212> TYPE: DNA
<213> ORGANISM: Artificial
<220> FEATURE:
<223> OTHER INFORMATION: Synthetic

<400> SEQUENCE: 58
cccttggccg aaggtgat                                                    18

<210> SEQ ID NO 59
<211> LENGTH: 108
<212> TYPE: PRT
<213> ORGANISM: Artificial
<220> FEATURE:
<223> OTHER INFORMATION: Synthetic

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 60
<211> LENGTH: 54
<212> TYPE: DNA
<213> ORGANISM: Artificial
<220> FEATURE:
<223> OTHER INFORMATION: Synthetic

<400> SEQUENCE: 60
gattttgcag tgtattactg tcagcagtat ggtagctcac cttggacgtt cggc           54

<210> SEQ ID NO 61
<211> LENGTH: 54
<212> TYPE: DNA
<213> ORGANISM: Artificial
```

```
<220> FEATURE:
<223> OTHER INFORMATION: Synthetic

<400> SEQUENCE: 61
gattttgcag tgtattactg tcatcaccat ggtcactcac cttggacgtt cggc         54

<210> SEQ ID NO 62
<211> LENGTH: 54
<212> TYPE: DNA
<213> ORGANISM: Artificial
<220> FEATURE:
<223> OTHER INFORMATION: Synthetic

<400> SEQUENCE: 62
gccgaacgtc caaggtgagt gaccatggtg atgacagtaa tacactgcaa aatc         54

<210> SEQ ID NO 63
<211> LENGTH: 47
<212> TYPE: DNA
<213> ORGANISM: Artificial
<220> FEATURE:
<223> OTHER INFORMATION: Synthetic

<400> SEQUENCE: 63
gcagtgtatt actgtcatca ctatggtcac tcaccttgga cgttcgg                 47

<210> SEQ ID NO 64
<211> LENGTH: 47
<212> TYPE: DNA
<213> ORGANISM: Artificial
<220> FEATURE:
<223> OTHER INFORMATION: Synthetic

<400> SEQUENCE: 64
ccgaacgtcc aaggtgagtg accatagtga tgacagtaat acactgc                 47

<210> SEQ ID NO 65
<211> LENGTH: 24
<212> TYPE: DNA
<213> ORGANISM: Artificial
<220> FEATURE:
<223> OTHER INFORMATION: Synthetic

<400> SEQUENCE: 65
aaagagccac cctctcctgc aggg                                          24

<210> SEQ ID NO 66
<211> LENGTH: 19
<212> TYPE: DNA
<213> ORGANISM: Artificial
<220> FEATURE:
<223> OTHER INFORMATION: Synthetic

<400> SEQUENCE: 66
tccaggcacc ctgtctttg                                                19

<210> SEQ ID NO 67
<211> LENGTH: 26
<212> TYPE: DNA
<213> ORGANISM: Artificial
<220> FEATURE:
<223> OTHER INFORMATION: Synthetic

<400> SEQUENCE: 67
aagtagctgc tgctaacact ctgact                                        26
```

```
<210> SEQ ID NO 68
<211> LENGTH: 15
<212> TYPE: DNA
<213> ORGANISM: Artificial
<220> FEATURE:
<223> OTHER INFORMATION: Synthetic

<400> SEQUENCE: 68
ctgtcatcac catgg                                                        15

<210> SEQ ID NO 69
<211> LENGTH: 23
<212> TYPE: DNA
<213> ORGANISM: Artificial
<220> FEATURE:
<223> OTHER INFORMATION: Synthetic

<400> SEQUENCE: 69
gcagactgga gcctgaagat ttt                                               23

<210> SEQ ID NO 70
<211> LENGTH: 20
<212> TYPE: DNA
<213> ORGANISM: Artificial
<220> FEATURE:
<223> OTHER INFORMATION: Synthetic

<400> SEQUENCE: 70
ccgaacgtcc aaggtgagtg                                                   20

<210> SEQ ID NO 71
<211> LENGTH: 17
<212> TYPE: DNA
<213> ORGANISM: Artificial
<220> FEATURE:
<223> OTHER INFORMATION: Synthetic

<400> SEQUENCE: 71
tactgtcatc actatgg                                                      17

<210> SEQ ID NO 72
<211> LENGTH: 22
<212> TYPE: DNA
<213> ORGANISM: Artificial
<220> FEATURE:
<223> OTHER INFORMATION: Synthetic

<400> SEQUENCE: 72
gcagactgga gcctgaagat tt                                                22

<210> SEQ ID NO 73
<211> LENGTH: 20
<212> TYPE: DNA
<213> ORGANISM: Artificial
<220> FEATURE:
<223> OTHER INFORMATION: Synthetic

<400> SEQUENCE: 73
ccgaacgtcc aaggtgagtg                                                   20

<210> SEQ ID NO 74
<211> LENGTH: 21
<212> TYPE: DNA
<213> ORGANISM: Artificial
<220> FEATURE:
<223> OTHER INFORMATION: Synthetic
```

```
<220> FEATURE:
<221> NAME/KEY: CDS
<222> LOCATION: (1)..(21)

<400> SEQUENCE: 74 cag cag tat ggt agc tca cct                                    21
Gln Gln Tyr Gly Ser Ser Pro
1               5

<210> SEQ ID NO 75
<211> LENGTH: 7
<212> TYPE: PRT
<213> ORGANISM: Artificial
<220> FEATURE:
<223> OTHER INFORMATION: Synthetic Construct

<400> SEQUENCE: 75

Gln Gln Tyr Gly Ser Ser Pro
1               5

<210> SEQ ID NO 76
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 76 cat cac cat ggt cac tca cct                                    21
His His His Gly His Ser Pro
1               5

<210> SEQ ID NO 77
<211> LENGTH: 7
<212> TYPE: PRT
<213> ORGANISM: Artificial
<220> FEATURE:
<223> OTHER INFORMATION: Synthetic Construct

<400> SEQUENCE: 77

His His His Gly His Ser Pro
1               5

<210> SEQ ID NO 78
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 78 cat cac tat ggt cac tca cct                                    21
His His Tyr Gly His Ser Pro
1               5

<210> SEQ ID NO 79
<211> LENGTH: 7
<212> TYPE: PRT
<213> ORGANISM: Artificial
<220> FEATURE:
<223> OTHER INFORMATION: Synthetic Construct

<400> SEQUENCE: 79
```

His His Tyr Gly His Ser Pro
1               5

<210> SEQ ID NO 80
<211> LENGTH: 108
<212> TYPE: PRT
<213> ORGANISM: Artificial
<220> FEATURE:
<223> OTHER INFORMATION: Synthetic

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 81
<211> LENGTH: 50
<212> TYPE: DNA
<213> ORGANISM: Artificial
<220> FEATURE:
<223> OTHER INFORMATION: Synthetic

<400> SEQUENCE: 81
caacttacta ctgtcaacag agttacagta cccctccgat caccttcggc          50

<210> SEQ ID NO 82
<211> LENGTH: 108
<212> TYPE: PRT
<213> ORGANISM: Artificial
<220> FEATURE:
<223> OTHER INFORMATION: Synthetic

<400> SEQUENCE: 82

Asp Ile Gln Met Thr Gln Ser Pro Ser Ser Leu Ser Ala Ser Val Gly
1               5                   10                  15

Asp Arg Val Thr Phe Thr Cys Arg Thr Ser His Ser Ile Ser Ser Tyr
            20                  25                  30

Leu Asn Trp Tyr Gln Gln Lys Pro Gly Lys Ala Pro Lys Ile Leu Ile
        35                  40                  45

Tyr Ala Val Ser Ser Leu Tyr Thr Gly Val Pro Ser Arg Phe Ser Ala
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Thr Cys Gln Gln Ser Tyr Asn Ile Pro Phe
                85                  90                  95

Thr Phe Gly Pro Gly Thr Lys Val Asp Ile Lys Arg
            100                 105

<210> SEQ ID NO 83
<211> LENGTH: 103
<212> TYPE: PRT
<213> ORGANISM: Artificial
<220> FEATURE:
<223> OTHER INFORMATION: Synthetic

<400> SEQUENCE: 83

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Asn Phe
            20                  25                  30

Leu Asn Trp Tyr Gln Gln Lys Pro Gly Lys Ala Pro Lys Leu Leu Ile
        35                  40                  45

Tyr Gly Ala Tyr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln His Leu Thr Phe Gly Gly Gly
                85                  90                  95

Thr Lys Val Glu Ile Lys Arg
            100

<210> SEQ ID NO 84
<211> LENGTH: 109
<212> TYPE: PRT
<213> ORGANISM: Artificial
<220> FEATURE:
<223> OTHER INFORMATION: Synthetic

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser His Asn Ile Asn Asn Tyr
            20                  25                  30

Leu Asn Trp Tyr His Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Thr Leu His Pro
65                  70                  75                  80

Glu Asp Phe Gly Asn Tyr Tyr Cys Gln Gln Ser Tyr Ser Thr Ser Met
                85                  90                  95

Tyr Thr Phe Gly Gln Gly Thr Gln Leu Glu Ile Lys Arg
            100                 105

<210> SEQ ID NO 85
<211> LENGTH: 108
<212> TYPE: PRT
<213> ORGANISM: Artificial
<220> FEATURE:
<223> OTHER INFORMATION: Synthetic

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Ser Tyr Ser Ile Pro Ile
                85                  90                  95

Thr Phe Gly Gln Gly Thr Arg Leu Glu Ile Lys Arg
                100                 105

<210> SEQ ID NO 86
<211> LENGTH: 108
<212> TYPE: PRT
<213> ORGANISM: Artificial
<220> FEATURE:
<223> OTHER INFORMATION: Synthetic

<400> SEQUENCE: 86

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Thr Ile Ser Ser Asn
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Ser Tyr Ile Thr Pro Ile
                85                  90                  95

Thr Phe Gly Gln Gly Thr Arg Leu Glu Ile Lys Arg
                100                 105

<210> SEQ ID NO 87
<211> LENGTH: 108
<212> TYPE: PRT
<213> ORGANISM: Artificial
<220> FEATURE:
<223> OTHER INFORMATION: Synthetic

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu His Pro
65                  70                  75                  80

Glu Asp Phe Ala Thr Tyr Tyr Cys Gln Gln Ser His Ser Thr Pro Ile
                85                  90                  95

Thr Phe Gly Gln Gly Thr Arg Leu Glu Ile Lys Arg
                100                 105

<210> SEQ ID NO 88
<211> LENGTH: 108
<212> TYPE: PRT

<400> SEQUENCE: 88

Ala Ile Gln Leu Thr Gln Ser Pro Ser Leu Ser Ala Ser Val Gly
1               5                   10                  15

Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Asn Leu Leu Ile
                35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser His Ser Thr Pro Ile
                85                  90                  95

Thr Phe Gly Gln Gly Thr Arg Leu Glu Ile Lys Arg
            100                 105

<210> SEQ ID NO 89
<211> LENGTH: 109
<212> TYPE: PRT
<213> ORGANISM: Artificial
<220> FEATURE:
<223> OTHER INFORMATION: Synthetic

<400> SEQUENCE: 89

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Ser Tyr
            20                  25                  30

Leu His Trp Tyr Gln Gln Lys Pro Gly Lys Ala Pro Lys Leu Leu Ile
                35                  40                  45

Tyr Asp Ala Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Val Glu Ile Lys Arg
            100                 105

<210> SEQ ID NO 90
<211> LENGTH: 109
<212> TYPE: PRT
<213> ORGANISM: Artificial
<220> FEATURE:
<223> OTHER INFORMATION: Synthetic

<400> SEQUENCE: 90

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
    50                  55                  60

```
Ser Lys Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ile His Pro
                 85                  90                  95

Ile Thr Phe Gly Gln Gly Thr Lys Leu Glu Ile Lys Arg
                100                 105
```

<210> SEQ ID NO 91
<211> LENGTH: 108
<212> TYPE: PRT
<213> ORGANISM: Artificial
<220> FEATURE:
<223> OTHER INFORMATION: Synthetic

<400> SEQUENCE: 91

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser His Ser Ile Pro Pro
                 85                  90                  95

Ile Thr Phe Gly Gln Gly Thr Arg Leu Glu Ile Lys
                100                 105
```

<210> SEQ ID NO 92
<211> LENGTH: 109
<212> TYPE: PRT
<213> ORGANISM: Artificial
<220> FEATURE:
<223> OTHER INFORMATION: Synthetic

<400> SEQUENCE: 92

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Met
             35                  40                  45

Tyr Ala Ala Ser Ser Leu Gln Ser Gly Val Pro Ser Arg Phe Ser Gly
     50                  55                  60

Thr Gly Ser Gly Thr Asp Phe Thr Leu Thr Ile Ser Ser Leu Gln Arg
 65                  70                  75                  80

Glu Asp Phe Ala Thr Tyr Tyr Cys Gln Gln Ser His Ser Thr Pro Pro
                 85                  90                  95

Ile Thr Phe Gly Gln Gly Thr Lys Val Glu Ile Lys Arg
                100                 105
```